United States Patent
Bennani et al.

(10) Patent No.: US 7,601,749 B2
(45) Date of Patent: Oct. 13, 2009

(54) INDOLE ACETIC ACIDS EXHIBITING CRTH2 RECEPTOR ANTAGONISM AND USES THEREOF

(75) Inventors: Youssef L. Bennani, Shaker Heights, OH (US); Lawrence Nathan Tumey, New Windsor, NY (US); Elizabeth Ann Gleason, Rocky River, OH (US); Michael Joseph Robarge, Burton, OH (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 12/336,274

(22) Filed: Dec. 16, 2008

(65) Prior Publication Data

US 2009/0111867 A1 Apr. 30, 2009

Related U.S. Application Data

(62) Division of application No. 12/131,537, filed on Jun. 2, 2008, now Pat. No. 7,476,667, which is a division of application No. 11/230,917, filed on Sep. 21, 2005, now Pat. No. 7,405,215.

(60) Provisional application No. 60/611,316, filed on Sep. 21, 2004.

(51) Int. Cl.
C07D 417/04 (2006.01)
C07D 413/04 (2006.01)
C07D 403/04 (2006.01)
A61K 31/501 (2006.01)

(52) U.S. Cl. ....................... 514/414; 548/458
(58) Field of Classification Search ................ 548/458; 514/414
See application file for complete search history.

(56) References Cited

U.S. PATENT DOCUMENTS

| | | | |
|---|---|---|---|
| 5,612,360 | A | 3/1997 | Boyd et al. |
| 6,114,532 | A | 9/2000 | Ries et al. |
| 6,121,308 | A | 9/2000 | Hauel et al. |

FOREIGN PATENT DOCUMENTS

| | | |
|---|---|---|
| WO | WO 02/060438 A1 | 8/2002 |
| WO | WO 03/066046 A1 | 8/2003 |
| WO | WO 03/066047 A1 | 8/2003 |
| WO | WO 03/101961 A1 | 12/2003 |
| WO | WO 03/101981 A1 | 12/2003 |
| WO | WO 2004/007451 A1 | 1/2004 |

OTHER PUBLICATIONS

International Search Report for corresponding PCT Application No. PCT/US2005/034029 dated Apr. 27, 2007.
International Search Report for PCT Application No. PCT/US2005/034028 dated Mar. 23, 2006.
Office Action issued in parent U.S. Appl. No. 11/230,917, mailed on Nov. 9, 2007.
Office Action issued in parent U.S. Appl. No. 11/230,917, mailed on Jul. 20, 2007.

*Primary Examiner*—Kahsay T Habte
(74) *Attorney, Agent, or Firm*—Finnegan, Henderson, Farabow, Garrett & Dunner LLP

(57) ABSTRACT

The invention relates to indole acetic acid compounds which function as antagonists of the CRTH2 receptor. The invention also relates to the use of these compounds to inhibit the binding of prostaglandin $D_2$ and its metabolites or certain thromboxane metabolites to the CRTH2 receptor and to treat disorders responsive to such inhibition.

23 Claims, No Drawings

INDOLE ACETIC ACIDS EXHIBITING CRTH2 RECEPTOR ANTAGONISM AND USES THEREOF

This application is a divisional of, and claims priority to, U.S. patent application Ser. No. 12/131,537, filed Jun. 2, 2008 (now U.S. Pat. No. 7,476,667), which is a divisional of, and claims priority to, U.S. patent application Ser. No. 11/230,917, filed Sep. 21, 2005 (now U.S. Pat. No. 7,405,215), which claims the benefit of priority to U.S. patent application Ser. No. 60/611,316, filed Sep. 21, 2004, all of which are incorporated herein by reference in their entirety.

BACKGROUND OF THE INVENTION

1. Field of the Invention

This invention is in the field of medicinal chemistry. In particular, the invention relates to indole acetic acid compounds which function as antagonists of the CRTH2 receptor. The invention also relates to the use of these compounds to inhibit the binding of prostaglandin $D_2$ and its metabolites to the CRTH2 receptor and to treat disorders responsive to such inhibition.

2. Related Art

The Chemoattractant Receptor-homologous molecule expressed on T-Helper type 2 cells (CRTH2) receptor binds prostaglandin $D_2$ ($PGD_2$) and its metabolites. Efforts have been made to inhibit the binding of $PGD_2$ and other ligands to the CRTH2 receptor in order to treat disorders and diseases related to excess activation of CRTH2.

Elevated $PGD_2$ is thought to play a causative role in both asthma and atopic dermatitis. For example, $PGD_2$ is one of the major prostanoids released by mast cells in the asthmatic lung and this molecule is found at high levels in the bronchial fluid of asthmatics (Liu et al., *Am. Rev. Respir. Dis.* 142:126 (1990)). Evidence of a role of $PGD_2$ in asthma is provided by a recent publication examining the effects of overexpression of prostaglandin D synthase on induction of allergic asthma in transgenic mice (Fujitani, *J. Immunol.* 168:443 (2002)). After allergen challenge, these animals had increased $PGD_2$ in the lungs, and the number of Th2 cells and eosinophils were greatly elevated relative to non-transgenic animals. These results are consistent with $PGD_2$ being a primary chemotactic agent in the recruitment of inflammatory cells during allergic asthma.

$PGD_2$ can bind to two G-protein coupled receptors, DP (Boie et al., *J. Biol. Chem.* 270:18910 (1995)) and CRTH2 (Nagata et al., *J. Immunol.* 162:1278 (1999); Hirai et al., *J. Exp. Med.* 193:255 (2001)). The latter receptor might play a particularly important role in diseases such as asthma and atopic dermatitis that are characterized by Th2 cell involvement, since Th2 cell chemotaxis in response to $PGD_2$ appears to be mediated by CRTH2 (Hirai et al., above). Moreover, eosinophils, the major inflammatory cell type seen in asthmatic lungs, show a CRTH2-mediated chemotactic response to $PGD_2$ (Hirai et al.) and certain thromboxane metabolites (Bohm et al., *J. Biol. Chem.* 279:7663 (2004)).

WO 03/066046 discloses compounds of the following formula which are active at the CRTH2 receptor:

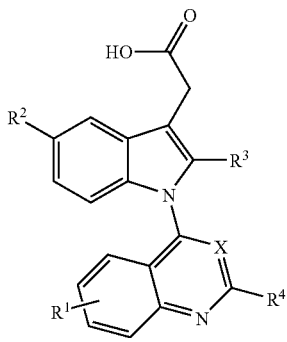

wherein:
$R^1$ is hydrogen, halogen, $C_{1-6}$ alkyl, $C_{1-6}$ alkoxy,
$R^2$ is hydrogen, halogen, $C_{1-6}$ alkyl, $C_{1-6}$ alkoxy;
$R^3$ is hydrogen, $C_{1-6}$ alkyl;
$R^4$ is hydrogen, $C_{1-6}$ alkyl, $C_{1-6}$ alkoxy, thio $C_{1-6}$ alkyl; and
X is N or CH.

WO 03/66047 discloses compounds of the following formula which are active at the CRTH2 receptor:

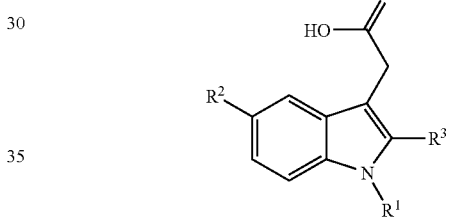

wherein:
$R^1$ is a 1,3-benzothiazole group optionally substituted by halogen, $C_{1-6}$ alkyl, $C_{1-6}$ alkoxy, or a group of Formula (A) or (B):

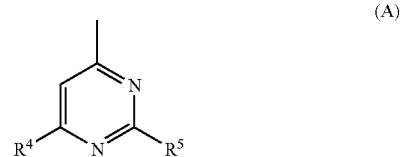

(A)

where $R^4$ and $R^5$ are independently halogen, $C_{1-6}$ alkyl, $C_{1-6}$ alkoxy, phenoxy optionally substituted by halogen, $C_{1-6}$ alkyl, $C_{1-6}$ alkoxy,

(B)

where one of X and Y is nitrogen and the other is nitrogen, oxygen, or sulfur and $R^6$ is phenyl optionally substituted by halogen, $C_{1-6}$ alkyl, $C_{1-6}$ alkoxy;

$R^2$ is hydrogen, halogen, $C_{1-6}$ alkyl, $C_{1-6}$ alkoxy; and $R^3$ is hydrogen, $C_{1-6}$ alkyl.

WO 03/101961 discloses compounds of the following formula which are active at the CRTH2 receptor:

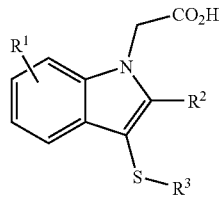

wherein:

$R^1$ is hydrogen, halogen, CN, nitro, $SO_2R^4$, OH, $OR^4$, $S(O)_x R^4$, $SO_2NR^5R^6$, $CONR^5R^6$, $NR^5R^6$, aryl (optionally substituted by chlorine or fluorine), $C_2$-$C_6$ alkenyl, $C_2$-$C_6$ alkynyl or $C_1$-$C_6$ alkyl, the latter three groups being optionally substituted by one or more substituents independently selected from halogen, $OR^8$ and $NR^5R^6$, $S(O)_x R^7$ where x is 0, 1, or 2;

$R^2$ is hydrogen, halogen, CN, $SO_2R^4$ or $CONR^5R^6$, $CH_2OH$, $CH_2OR^4$ or $C_1$-$C_7$ alkyl, the latter group being optionally substituted by one or more substituents independently selected from halogen atoms, $OR^8$ and $NR^5R^6$, $S(O)_x R^7$ where x is 0, 1, or 2;

$R^3$ is aryl or heteroaryl each of which is optionally substituted by one or more substituents independently selected from hydrogen, halogen, CN, nitro, OH, $SO_2R^4$, $OR^4$, $SR^4$, $SOR^4$, $SO_2NR^5R^6$, $CONR^5R^6$, $NR^5R^6$, $NHCOR^4$, $NHSO_2R^4$, $NHCO_2R^4$, $NR^7SO_2R^4$, $NR^7CO_2R^4$, $C_2$-$C_6$ alkenyl, $C_2$-$C_6$ alkynyl or $C_1$-$C_6$ alkyl, the latter three groups being optionally substituted by one or more substituents independently selected from halogen, $OR^8$ and $NR^5R^6$, $S(O)_x R^7$ where x is 0, 1, or 2;

$R^4$ represents aryl, heteroaryl, or $C_1$-$C_6$ alkyl all of which may be optionally substituted by one or more substituents independently selected from halogen atoms, aryl, heteroaryl, $OR^{10}$, OH, $NR^{11}R^{12}$, $S(O)_x R^{13}$ (where x=0, 1, or 2), $CONR^{14}R^{15}$, $NR^{14}COR^{15}$, $SO_2NR^{14}R^{15}$, $NR^{14}SO_2R^{15}$, CN, nitro;

$R^5$ and $R^6$ independently represent a hydrogen atom, a $C_1$-$C_6$ alkyl group, or an aryl, or a heteroaryl, the latter three of which may be optionally substituted by one or more substituents independently selected from halogen atoms, aryl, $OR^8$ and $NR^{14}R^{15}$, $CONR^{14}R^{15}$, $NR^{14}COR^{15}$, $SO_2NR^{14}R^{15}$, $NR^{14}SO_2R^{15}$, CN, nitro; or $R^5$ and $R^6$ together with the nitrogen atom to which they are attached can form a 3-8 membered saturated heterocyclic ring optionally containing one or more atoms selected from O, $S(O)_x$ where x=0, 1, or 2, $NR^{16}$, and itself optionally substituted by $C_1$-$C_3$ alkyl;

$R^7$ and $R^{13}$ independently represent a $C_1$-$C_6$ alkyl, an aryl or a heteroaryl group, all of which may be optionally substituted by halogen atoms;

$R^8$ represents a hydrogen atom, $C(O)R^9$, $C_1$-$C_6$ alkyl, an aryl or a heteroaryl group, all of which may be optionally substituted by halogen atoms;

each of $R^9$, $R^{10}$, $R^{11}$, $R^{12}$, $R^{14}$, $R^{15}$, independently represents a hydrogen atom, $C_1$-$C_6$ alkyl, an aryl or heteroaryl group (all of which may be optionally substituted by halogen atoms); and $R^{16}$ is hydrogen, $C_1$-$C_4$ alkyl, $COC_1$-$C_4$ alkyl, $COYC_1$-$C_4$ alkyl where Y is O or $NR^7$, provided that when $R^1$ is hydrogen and $R^2$ is methyl, then $R^3$ is not 2-nitrophenyl.

WO 03/101981 discloses compounds of the following formula which are active at the CRTH2 receptor:

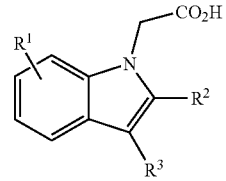

wherein:

$R^1$ is hydrogen, halogen, CN, nitro, $SO_2R^4$, OH, $OR^4$, $SR^4$, $SOR^4$, $SO_2NR^5R^6$, $CONR^5R^6$, $NR^5R^6$, $NR^9SO_2R^4$, $NR^9CO_2R^4$, $NR^9COR^4$, heteroaryl, aryl, $C_2$-$C_6$ alkenyl, $C_2$-$C_6$ alkynyl or $C_1$-$C_6$ alkyl, the latter five groups being optionally substituted by one or more substituents independently selected from halogen, $OR^8$ and $NR^5R^6$, $S(O)_x R^7$ where x is 0, 1, or 2;

$R^2$ is hydrogen, halogen, CN, $SO_2R^4$ or $CONR^5R^6$, $CH_2OH$, $CH_2OR^4$ or $C_1$-$C_7$ alkyl, the latter group being optionally substituted by one or more substituents independently selected from halogen atoms, $OR^8$ and $NR^5R^6$, $S(O)_x R^7$ where x is 0, 1, or 2;

$R^3$ is aryl or heteroaryl each of which is optionally substituted by one or more substituents independently selected from hydrogen, halo-en, CN, nitro, OH, $SO_2R^4$, $OR^4$, $SR^4$, $SOR^4$, $SO_2NR^5R^6$, $CONR^5R^6$, $NR^5R^6$, $NR^9SO_2R^4$, $NR^9CO_2R^4$, $NR^9CO_2H$, $NR^9COR^4$, $C_2$-$C_6$ alkenyl, $C_2$-$C_6$ alkynyl, $C_1$-$C_6$ alkyl, the latter three groups being optionally substituted by one or more substituents independently selected from halogen atoms, $OR^8$ and $NR^5R^6$, $S(O)_x R^7$ where x is 0, 1, or 2; with the proviso that $R^3$ cannot be phenyl or substituted phenyl;

$R^4$ represents aryl, heteroaryl, or $C_1$-$C_6$ alkyl all of which may be optionally substituted by one or more substituents independently selected from halogen atoms, aryl, heteroaryl, $OR^{10}$, and $NR^{11}R^{12}$, $S(O)_x R^{13}$ (where x=0, 1, or 2), $CONR^{14}R^{15}$, $NR^{14}COR^{15}$, $SO_2NR^{14}R^{15}$, $NR^{14}SO_2R^{15}$;

$R^5$ and $R^6$ independently represent a hydrogen atom, a $C_1$-$C_6$ alkyl group, or an aryl, or a heteroaryl, the latter three of which may be optionally substituted by one or more substituents independently selected from halogen atoms, aryl, $OR^8$ and $NR^{14}R^{15}$, $CONR^{14}R^{15}$, $NR^{14}COR^{15}$, $SO_2NR^{14}R^{15}$, $NR^{14}SO_2R^{15}$; or $R^5$ and $R^6$ together with the nitrogen atom to which they are attached can form a 3-8 membered saturated heterocyclic ring optionally containing one or more atoms selected from O, $S(O)_x$ where x=0, 1, or 2, $NR^{16}$, and itself optionally substituted by $C_1$-$C_3$ alkyl;

$R^7$ and $R^{13}$ independently represent a $C_1$-$C_6$ alkyl, an aryl or a heteroaryl group, all of which may be optionally substituted by halogen atoms;

$R^8$ represents a hydrogen atom, $C(O)R^9$, $C_1$-$C_6$ alkyl, an aryl or a heteroaryl group, all of which may be optionally substituted by halogen atoms or an aryl group;

each of $R^9$, $R^{10}$, $R^{11}$, $R^{12}$, $R^{14}$, $R^{15}$, independently represents a hydrogen atom, $C_1$-$C_6$ alkyl, an aryl or heteroaryl group (all of which may be optionally substituted by halogen atoms); and $R^{16}$ is hydrogen, $C_1$-$C_4$ alkyl, $COC_1$-$C_4$ alkyl, $COYC_1$-$C_4$ alkyl where Y is O or $NR^7$.

WO 2004/007451 discloses compounds of the following formula which are active at the CRTH2 receptor:

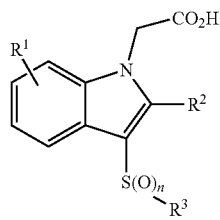

wherein:

n represents 1 or 2;

$R^1$ is one or more substituents independently selected from halogen, CN, nitro, $SO_2R^4$, $OR^4$, $SR^4$, $SOR^4$, $SO_2NR^5R^6$, $CONR^5R^6$, $NR^5R^6$, $NR^9SO_2R^4$, $NR^9CO_2R^4$, $NR^9COR^4$, aryl, heteroaryl, $C_2$-$C_6$ alkenyl, $C_2$-$C_6$ alkynyl or $C_1$-$C_6$ alkyl, the latter five groups being optionally substituted by one or more substituents independently selected from halogen, $OR^7$ and $NR^8R^9$, $S(O)_xR^7$ where x is 0, 1, or 2;

$R^2$ is hydrogen, halogen, CN, $SO_2R^4$ or $CONR^5R^6$, $COR^4$ or $C_1$-$C_7$ alkyl the latter group being optionally substituted by one or more substituents independently selected from halogen atoms, $OR^8$ and $NR^5R^6$, $S(O)_xR^7$ where x is 0, 1, or 2;

$R^3$ is aryl or a 5-7 membered heteroaryl ring containing one or more heteroatoms selected from N, S, and O, each of which is optionally substituted by one or more substituents independently selected from halogen, CN, nitro, $SO_2R^4$, OH, $OR^4$, $SR^4$, $SOR^4$, $SO_2NR^5R^6$, $CONR^5R^6$, $NR^5R^6$, $NR^9SO_2R^4$, $NR^9CO_2R^4$, $NR^9COR^4$, $C_2$-$C_6$ alkenyl, $C_2$-$C_6$ alkynyl $C_1$-$C_6$ alkyl, the latter three groups being optionally substituted by one or more substituents independently selected from halogen atoms, $OR^7$ and $NR^5R^6$, $S(O)_xR^7$ where x is 0, 1, or 2;

$R^4$ represents aryl, heteroaryl, or $C_1$-$C_6$ alkyl all of which may be optionally substituted by one or more substituents independently selected from halogen atoms, aryl, heteroaryl, $OR^{10}$, and $NR^{11}R^{12}$, $S(O)_xR^{13}$ (where x=0, 1, or 2), $CONR^{14}R^{15}$, $NR^{14}COR^{15}$, $SO_2NR^{14}R^{15}$, $NR^{14}SO_2R^{15}$, CN, nitro;

$R^5$ and $R^6$ independently represent a hydrogen atom, a $C_1$-$C_6$ alkyl group, an aryl, or a heteroaryl, the latter three of which may be optionally substituted by one or more substituents independently selected from halogen atoms, aryl, $OR^{13}$ and $NR^{14}R^{15}$, $CONR^{14}R^{15}$, $NR^{14}COR^{15}$, $SO_2NR^{14}R^{15}$, $NR^{14}SO_2R^{15}$, CN, nitro; or $R^5$ and $R^6$ together with the nitrogen atom to which they are attached can form a 3-8 membered saturated heterocyclic ring optionally containing one or more atoms selected from O, $S(O)_x$ where x=0, 1, or 2, $NR^{16}$, and the ring itself optionally substituted by $C_1$-$C_3$ alkyl;

$R^7$ and $R^{13}$ independently represent a $C_1$-$C_6$ alkyl, an aryl or a heteroaryl group, all of which may be optionally substituted by halogen atoms;

$R^8$ represents a hydrogen atom, $C(O)R^9$, $C_1$-$C_6$ alkyl (optionally substituted by halogen atoms, aryl or heteroaryl groups, both of which may also be optionally substituted by one or more fluorine atoms), an aryl or heteroaryl group, which may be optionally substituted by one or more halogen atoms;

each of $R^9$, $R^{10}$, $R^{11}$, $R^{12}$, $R^{14}$, $R^{15}$, independently represents a hydrogen atom, $C_1$-$C_6$ alkyl, an aryl or a heteroaryl group (all of which may be optionally substituted by halogen atoms); and $R^{16}$ is hydrogen, $C_1$-$C_4$ alkyl, $COC_1$-$C_4$ alkyl, $C(O)YC_1$-$C_4$ alkyl, Y is O or $NR^7$.

WO 02/060438 discloses compounds of the following formula that can be used as integrin antagonists:

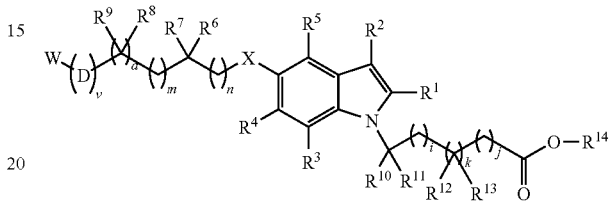

wherein $R^1$, $R^2$, $R^3$, $R^4$, and $R^5$ independently represent hydrogen, halogen, alkyl, aryl, aralkyl, heteroaryl, or heteroarylalkyl;

$R^6$, $R^7$, $R^8$, and $R^9$ independently represent hydrogen, alkyl, hydroxyalkyl, aminoalkyl, monoalkylaminoalkyl, dialkylaminoalkyl, carboxyalkyl, aryl, or aralkyl;

or $R^6$ and $R^7$ are taken together to form —$(CH_2)_p$—, where p is 2-8, while $R^8$ and $R^9$ are defined as above; or $R^8$ and $R^9$ are taken together to form —$(CH_2)_q$—, where q is 2-8, while $R^6$ and $R^7$ are defined as above; or $R^6$ and $R^8$ are taken together to form —$(CH_2)_r$—, while r is zero (a bond), 1, or 2, while $R^7$ and $R^9$ are defined as above;

X represents oxygen, sulfur, —$CH_2$—, —NH—, —(C=O)NH—, or —NH(C=O)—;

n is from 0 to 4;

m is from 0 to 4;

a is 0 or 1;

D represents oxygen;

V is 0 or 1;

$R^{10}$, $R^{11}$, $R^{12}$, and $R^{13}$ independently represent: hydrogen; hydroxy; alkyl; alkoxy; cycloalkyl; aryl, optionally substituted with one or more of halogen, hydroxy, cyano, alkyl, aryl, alkoxy, haloalkyl, arylalkyl, arylalkoxy, aryloxy, alkylsulfonyl, alkylsulfinyl, alkoxyarylalkyl, monoalkylamino, dialkylamino, aminoalkyl, monoalkylaminoalkyl, dialkylaminoalkyl, alkanoyl; monoalkylamino; dialkylamino; aminoalkyl; monoalkylaminoalkyl; dialkylaminoalkyl; alkanoyl; heteroaryl having 5-14 ring members, optionally substituted with one or more of halogen, hydroxy, cyano, alkyl, aryl, alkoxy, haloalkyl, arylalkyl, arylalkoxy, aryloxy, alkylsulfonyl, alkylsulfinyl, alkoxyarylalkyl, monoalkylamino, dialkylamino, aminoalkyl, monoalkylaminoalkyl, dialkylaminoalkyl, alkanoyl; or

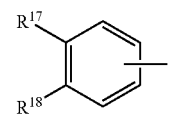

wherein $R^{17}$ and $R^{18}$ together form —$CH_2CH_2$—O—, —O—$CH_2CH_2$—, —O—$CH_2$—O—, or —O—$CH_2CH_2$—O—; or $R^{10}$ and $R^{12}$ are taken together to form —$(CH_2)_s$—, wherein s is 0 (a bond) or 1 to 4, while $R^{11}$ and $R^{13}$ are defined as above; or $R^{10}$ and $R^{12}$ are taken together to form a double bond when i is 0 and k is 1, while $R^{11}$ and $R^{13}$ are as defined above; or $R^{10}$ and $R^{11}$ are taken together to form —$(CH_2)_t$—, wherein t is 2 to 8, while $R^{12}$ and $R^{13}$ are defined as above, or $R^{12}$ and $R^{13}$ are taken together to form —$(CH_2)_u$— wherein u is 2 to 8, while $R^{10}$ and $R^{11}$ are defined as above;

i is from 0 to 4;
j is from 0 to 4;
k is 0 or 1;
$R^{14}$ is hydrogen or a functionality that acts as a prodrug;
W is

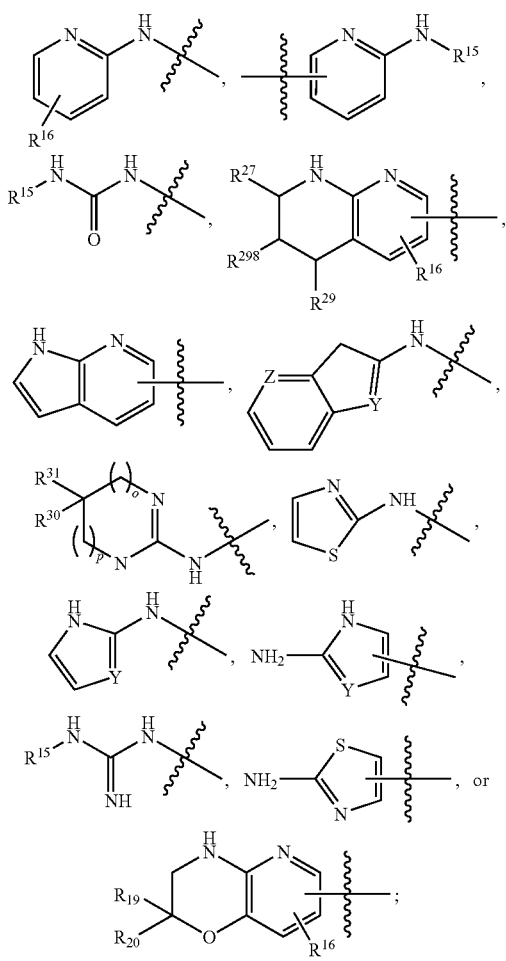

wherein Y is —N— or —CH—;
Z is —N— or —CH—;
$R^{15}$ is hydrogen, halogen, alkyl, aryl, or arylalkyl;
$R^{16}$ is hydrogen, alkyl, haloalkyl, or halogen;
$R^{19}$ and $R^{20}$ are independently hydrogen, halogen, or alkyl;
$R^{27}$, $R^{28}$, $R^{29}$, $R^{30}$, and $R^{31}$ are independently hydrogen, halogen, alkyl, alkoxy or aryl; and
o and p are independently 0, 1, or 2.

SUMMARY OF THE INVENTION

The present invention relates to indole acetic acid compounds that are useful for inhibiting binding of endogenous ligands to the CRTH2 receptor. In particular, the compounds of the present invention act as antagonists of the human CRTH2 receptor (hCRTH2). In one embodiment, the indole acetic acids are compounds of Formula I:

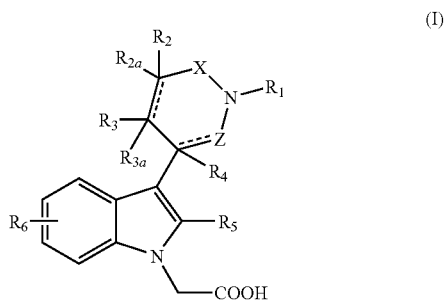

and pharmaceutically acceptable salts and prodrugs thereof, wherein:

the dotted lines are single or double bonds;
X is C=O, S=O, or $SO_2$;
Z is N or a covalent bond;
$R_1$ is selected from the group consisting of H or optionally substituted $C_{1-10}$ alkyl, $C_{2-10}$ alkenyl, $C_{2-10}$ alkynyl, $C_{1-10}$ alkylaryl, $C_{1-10}$ alkylheteroaryl, —$C_{1-10}$ alkyl-O—$C_{1-10}$ alkyl, —$C_{1-10}$ alkyl-O-aryl, —$C_{1-10}$ alkyl-O-heteroaryl, aryl, or heteroaryl;
$R_2$, $R_{2a}$, $R_3$ and $R_{3a}$ are independently selected from the group consisting of H, halogen, or $C_{1-10}$ alkyl, wherein $R_{2a}$ and $R_{3a}$ exist only when the carbons to which they are attached are saturated; or
$R_2$ and $R_3$ form an optionally substituted saturated, unsaturated, or aromatic 5- or 6-member ring; or
$R_2$ and $R_{2a}$ form an optionally substituted saturated 3-6 member ring;
$R_4$ is H, $C_{1-10}$ alkyl, $C_{2-10}$ alkenyl, $C_{2-10}$ alkynyl, or halogen, wherein $R_4$ exists only when the carbon to which it is attached is saturated;
$R_5$ is H, $C_{1-10}$ alkyl, perhaloalkyl (preferably $CF_3$), $C_{2-10}$ alkenyl, $C_{2-10}$ alkynyl, $C_{1-10}$ alkylaryl, $C_{1-10}$ alkylheteroaryl, aryl, or heteroaryl, wherein said aryl or heteroaryl can be optionally substituted with one or more substituents selected from $C_{1-10}$ alkyl, halogen, $C_{1-10}$ alkoxy, or CN;
$R_6$ is one or more H, halogen, $C_{1-10}$ alkyl, $C_{2-10}$ alkenyl, $C_{2-10}$ alkynyl, CN, $OR_7$, $SR_7$, aryl or heteroaryl groups; and
$R_7$ is H, $C_{1-10}$ alkyl, $C_{2-10}$ alkenyl, $C_{2-10}$ alkynyl, aryl, or heteroaryl.

The invention relates to compounds represented by Formula I, which are antagonists of CRTH2. The invention relates to the use of the compounds of the invention to inhibit binding of endogenous ligands, including $PGD_2$ and its metabolites and certain thromboxane metabolites (such as 11-dehydro-$TXB_2$ (Bohm et al., *J. Biol. Chem.* 279:7663 (2004)), to CRTH2. The compounds are useful for the treatment, amelioration, or prevention of disorders responsive to inhibition of binding to CRTH2, e.g., disorders characterized by elevated levels of $PGD_2$ or its metabolites or certain thromboxane metabolites. These disorders include, but are not limited to, respiratory tract disorders (e.g., asthma, chronic obstructive pulmonary disease, rhinitis), bone and joint disorders (e.g. arthritis, Sjogren's syndrome), skin and eye disorders (e.g., psoriasis, dermatitis, uveitis, conjunctivitis), gastrointestinal tract disorders (e.g., colitis, celiac disease, Crohn's disease), central and peripheral nervous system disorders (e.g., Alzheimer's disease, multiple sclerosis, migraine, stroke), disorders of other tissues and systemic disorders (e.g., atherosclerosis, AIDS, sepsis, ischemic/reperfusion injury, hepatitis) and allograft rejection.

The present invention provides methods of blocking/antagonizing the CRTH2 receptor on a cell, comprising contacting the cell with a compound of Formula I. The present invention also provides methods of treating, ameliorating, or preventing a disorder responsive to blocking/antagonizing the CRTH2 receptor in an animal, comprising administering to said animal a therapeutically effective amount of a compound of Formula I.

The present invention provides pharmaceutical compositions comprising a compound of Formula I in a therapeutically effective amount to inhibit binding to the CRTH2 receptor. The compositions may further comprise other therapeutic agents.

The invention further provides kits comprising a compound of Formula I and instructions for administering the compound to an animal. The kits may optionally contain other therapeutic agents.

The invention also provides methods of making compounds of Formula I.

DETAILED DESCRIPTION OF THE INVENTION

The present invention relates to compounds represented by Formula I, which are antagonists of the CRTH2 receptor and function as inhibitors of the binding of endogenous ligands to the CRTH2 receptor. By inhibiting the binding of endogenous ligands such as $PGD_2$ and its metabolites, these compounds at least partially inhibit the effects of the endogenous ligands in an animal. Therefore, the invention relates to methods of inhibiting the binding of endogenous ligands to the CRTH2 receptor on a cell, comprising contacting the cell with a compound of Formula I. The invention further relates to methods of treating, ameliorating, or preventing disorders in an animal that are responsive to inhibition of the CRTH2 receptor comprising administering to the animal a compound of Formula I. Such disorders include those characterized by elevated levels of $PGD_2$ or its metabolites or certain thromboxane metabolites.

The term "CRTH2 receptor," as used herein, refers to any known member of the CRTH2 receptor family, including, but not limited to, hCRTH2.

The term "elevated levels of $PGD_2$ or its metabolites or certain thromboxane metabolites," as used herein, refers to an elevated level (e.g., aberrant level) of these molecules in biological tissue or fluid as compared to similar corresponding non-pathological tissue or fluid containing basal levels of $PGD_2$ or its metabolites or thromboxanes and metabolites.

The term "other therapeutic agents," as used herein, refers to any therapeutic agent that has been used, is currently used, or is known to be useful for treating, ameliorating, or preventing a disorder encompassed by the present invention. For example, agents used to treat asthma and rhinitis include steroids, β2-receptor agonists and leukotriene receptor antagonists.

The term "prodrug," as used herein, refers to a pharmacologically inactive derivative of a parent "drug" molecule that requires biotransformation (e.g., either spontaneous or enzymatic) within the target physiological system to release or convert the prodrug into the active drug. Prodrugs are designed to overcome problems associated with stability, toxicity, lack of specificity, or limited bioavailability. Exemplary prodrugs comprise an active drug molecule itself and a chemical masking group (e.g., a group that reversibly suppresses the activity of the drug). Some preferred prodrugs are variations or derivatives of compounds that have groups cleavable under metabolic conditions. Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common prodrugs include acid derivatives such as esters prepared by reaction of parent acids with a suitable alcohol (e.g., a lower alkanol), amides prepared by reaction of the parent acid compound with an amine, or basic groups reacted to form an acylated base derivative (e.g., a lower alkylamide).

The term "pharmaceutically acceptable salt," as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of asthma, a therapeutically effective amount preferably refers to the amount of a therapeutic agent that increases peak air flow by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "prevent," "preventing," and "prevention," as used herein, refer to a decrease in the occurrence of pathological cells (e.g., $Th_2$ cells, eosinophils, etc.) or a pathological condition (e.g., constricted airways) in an animal. The prevention may be complete, e.g., the total absence of pathological cells or a pathological condition in an animal. The prevention may also be partial, such that the occurrence of pathological cells or a pathological condition in an animal is less than that which would have occurred without the present invention.

The compounds of the present invention are compounds having Formula I:

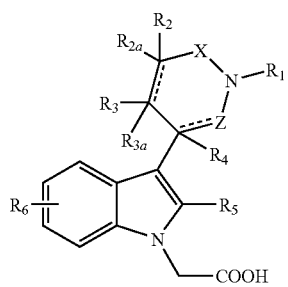

and pharmaceutically acceptable salts and prodrugs thereof, wherein:

the dotted lines are single or double bonds;

X is C=O, S=O, or $SO_2$;

Z is N or a covalent bond;

$R_1$ is selected from the group consisting of H or optionally substituted $C_{1-10}$ alkyl, $C_{2-10}$ alkenyl, $C_{2-10}$ alkynyl, $C_{1-10}$ alkylaryl, $C_{1-10}$ alkylheteroaryl, —$C_{1-10}$ alkyl-O—$C_{1-10}$ alkyl, —$C_{1-10}$ alkyl-O-aryl, —$C_{1-10}$ alkyl-O-heteroaryl, aryl, or heteroaryl;

$R_2$, $R_{2a}$, $R_3$ and $R_{3a}$ are independently selected from the group consisting of H, halogen, or $C_{1-10}$ alkyl, wherein $R_{2a}$ and $R_{3a}$ exist only when the carbons to which they are attached are saturated; or $R_2$ and $R_3$ form an optionally substituted saturated, unsaturated, or aromatic 5- or 6-member ring; or $R_2$ and $R_{2a}$ form an optionally substituted saturated 3-6 member ring;

$R_4$ is H, $C_{1-10}$ alkyl, $C_{2-10}$ alkenyl, $C_{2-10}$ alkynyl, or halogen, wherein $R_4$ exists only when the carbon to which it is attached is saturated;

$R_5$ is H, $C_{1-10}$ alkyl, perhaloalkyl (preferably $CF_3$), $C_{2-10}$ alkenyl, $C_{2-10}$ alkynyl, $C_{1-10}$ alkylaryl, $C_{1-10}$ alkylheteroaryl, aryl, or heteroaryl, wherein said aryl or heteroaryl can be optionally substituted with one or more substituents selected from $C_{1-10}$ alkyl, halogen, $C_{1-10}$ alkoxy, or CN;

$R_6$ is one or more H, halogen, $C_{1-10}$ alkyl, $C_{2-10}$ alkenyl, $C_{2-10}$ alkynyl, CN, $OR_7$, $SR_7$, aryl or heteroaryl groups; and $R_7$ is H, $C_{1-10}$ alkyl, $C_{2-10}$ alkenyl, $C_{2-10}$ alkynyl, aryl, or heteroaryl.

In particular embodiments, the compounds of the present invention are compounds having Formula II:

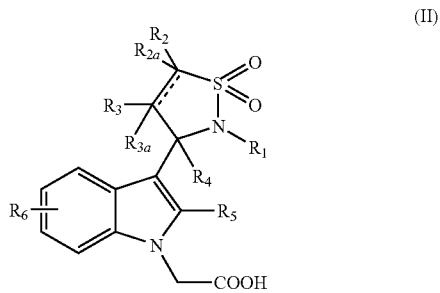

and pharmaceutically acceptable salts and prodrugs thereof, wherein $R_1$-$R_7$ are as defined above.

In particular embodiments, the compounds of the present invention are compounds having Formula III:

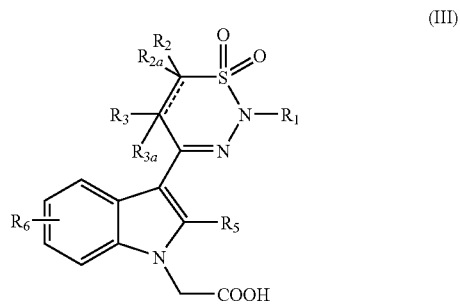

and pharmaceutically acceptable salts and prodrugs thereof, wherein $R_1$-$R_7$ are as defined above.

In particular embodiments, the compounds of the present invention are compounds having Formula IV:

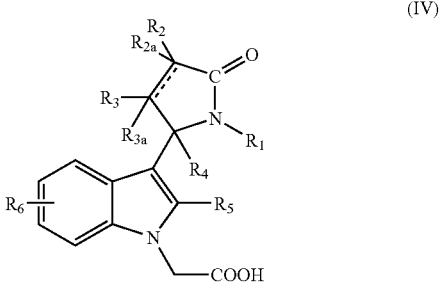

and pharmaceutically acceptable salts and prodrugs thereof, wherein $R_1$-$R_7$ are as defined above.

In particular embodiments, the compounds of the present invention are compounds having Formula V:

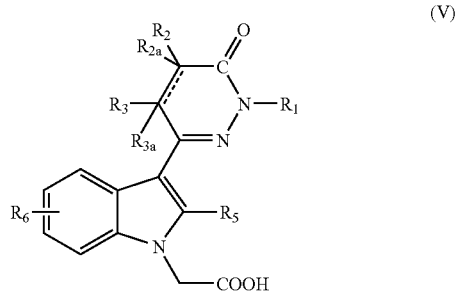

(V)

and pharmaceutically acceptable salts and prodrugs thereof, wherein $R_1$-$R_7$ are as defined above.

Useful alkyl groups include straight-chained or branched $C_{1-10}$ alkyl groups, especially methyl, ethyl, propyl, isopropyl, t-butyl, sec-butyl, 3-pentyl, adamantyl, norbornyl, and 3-hexyl groups, as well as $C_{1-10}$ cycloalkyl groups, e.g., cyclopropyl, cyclobutyl, cyclopentyl, and cyclohexyl. Lower alkyl groups are $C_{1-6}$ alkyl groups.

Useful alkenyl groups include straight-chained or branched $C_{2-10}$ alkyl groups, especially ethenyl, propenyl, isopropenyl, butenyl, isobutenyl, and hexenyl.

Useful alkynyl groups include straight-chained or branched $C_{2-10}$ alkynyl groups, especially ethynyl, propynyl, butynyl, isobutynyl, and hexynyl.

Useful acyloxyl groups are any $C_{1-6}$ acyl (alkanoyl) attached to an oxy (—O—) group, e.g., formyloxy, acetoxy, propionoyloxy, butanoyloxy, pentanoyloxy, hexanoyloxy and the like.

Useful aryl groups include $C_{6-14}$ aryl, especially phenyl, naphthyl, phenanthrenyl, anthracenyl, indenyl, azulenyl, biphenyl, biphenylenyl, and fluorenyl groups.

Useful heteroaryl groups include thiazolyl, oxazolyl, thienyl, benzo[b]thienyl, naphtho[2,3-b]thienyl, benzodioxinyl, benzothiazolyl, thianthrenyl, furyl, pyranyl, isobenzofuranyl, chromenyl, xanthenyl, phenoxanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, benzimidazolyl, 2-oxindolyl, and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide, pyrimidinyl N-oxide, and the like.

Optional substituents include one or more alkyl; halo; haloalkyl; haloalkoxy; cycloalkyl; hydroxy; cyano; aryl optionally substituted with one or more lower alkyl, halo, haloalkyl, alkoxy, haloalkoxy, aryl, aryloxy, heteroaryl or heteroaryloxy groups; aryloxy optionally substituted with one or more lower alkyl, haloalkyl, alkoxy, haloalkoxy, aryl, or heteroaryl groups; carbamoyl optionally substituted with one or more lower alkyl, halo, haloalkyl, alkoxy, haloalkoxy, aryl or heteroaryl groups; aralkyl, heteroaryl optionally substituted with one or more lower alkyl, halo, haloalkyl, haloalkoxy, alkoxy, aryl, aryloxy, heteroaryl or heteroaryloxy groups; heteroaryloxy optionally substituted with one or more lower alkyl, haloalkyl, alkoxy, haloalkoxy, and aryl groups; alkoxy; alkoxycarbonyl; alkylthio; arylthio; amino; acyloxy; arylacyloxy optionally substituted with one or more lower alkyl, haloalkyl, alkoxy, haloalkoxy, and aryl groups; diphenylphosphinyloxy optionally substituted with one or more lower alkyl, halo, haloalkyl, alkoxy, or haloalkoxy groups; heterocyclo optionally substituted with one or more lower alkyl, haloalkyl, alkoxy, haloalkoxy, and aryl groups; heterocycloalkoxy optionally substituted with one or more lower alkyl, haloalkyl, alkoxy, haloalkoxy, and aryl groups; partially unsaturated heterocycloalkyl optionally substituted with one or more lower alkyl, haloalkyl, alkoxy, haloalkoxy, and aryl groups; or partially unsaturated heterocycloalkyloxy optionally substituted with one or more lower alkyl, haloalkyl, alkoxy, haloalkoxy, and aryl groups.

Useful halo or halogen groups include fluorine, chlorine, bromine and iodine.

Useful arylalkyl groups or heteroarylalkyl groups include any of the above-mentioned $C_{1-10}$ alkyl groups substituted by any of the above-mentioned $C_{6-14}$ aryl groups or heteroaryl groups. Useful values include benzyl, phenethyl and naphthylmethyl.

Useful arylacyloxyl groups or heteroarylacyloxyl groups include any of the aryl groups or heteroaryl groups mentioned above substituted on any of the acyloxyl groups mentioned above, e.g. 2,6-dichlorobenzoyloxy, 2,6-difluorobenzoyloxy and 2,6-di-(trifluoromethyl)-benzoyloxy groups.

Useful alkoxyl groups include oxygen substituted by one of the $C_{1-10}$ alkyl groups mentioned above.

Useful arylalkoxyl groups or heteroarylalkoxyl groups include any of the aryl groups or heteroaryl groups mentioned above substituted on any of the alkoxyl groups mentioned above Useful heterocyclic groups include tetrahydrofuranyl, pyranyl, piperidinyl, piperizinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups.

Certain of the compounds of the present invention may exist as stereoisomers including optical isomers. The invention includes all stereoisomers and both the racemic mixtures of such stereoisomers as well as the individual enantiomers that may be separated according to methods that are well known to those of skill in the art.

The compounds of this invention may be prepared using methods known to those of skill in the art. In one embodiment, the compounds may be prepared by general synthetic scheme 1:

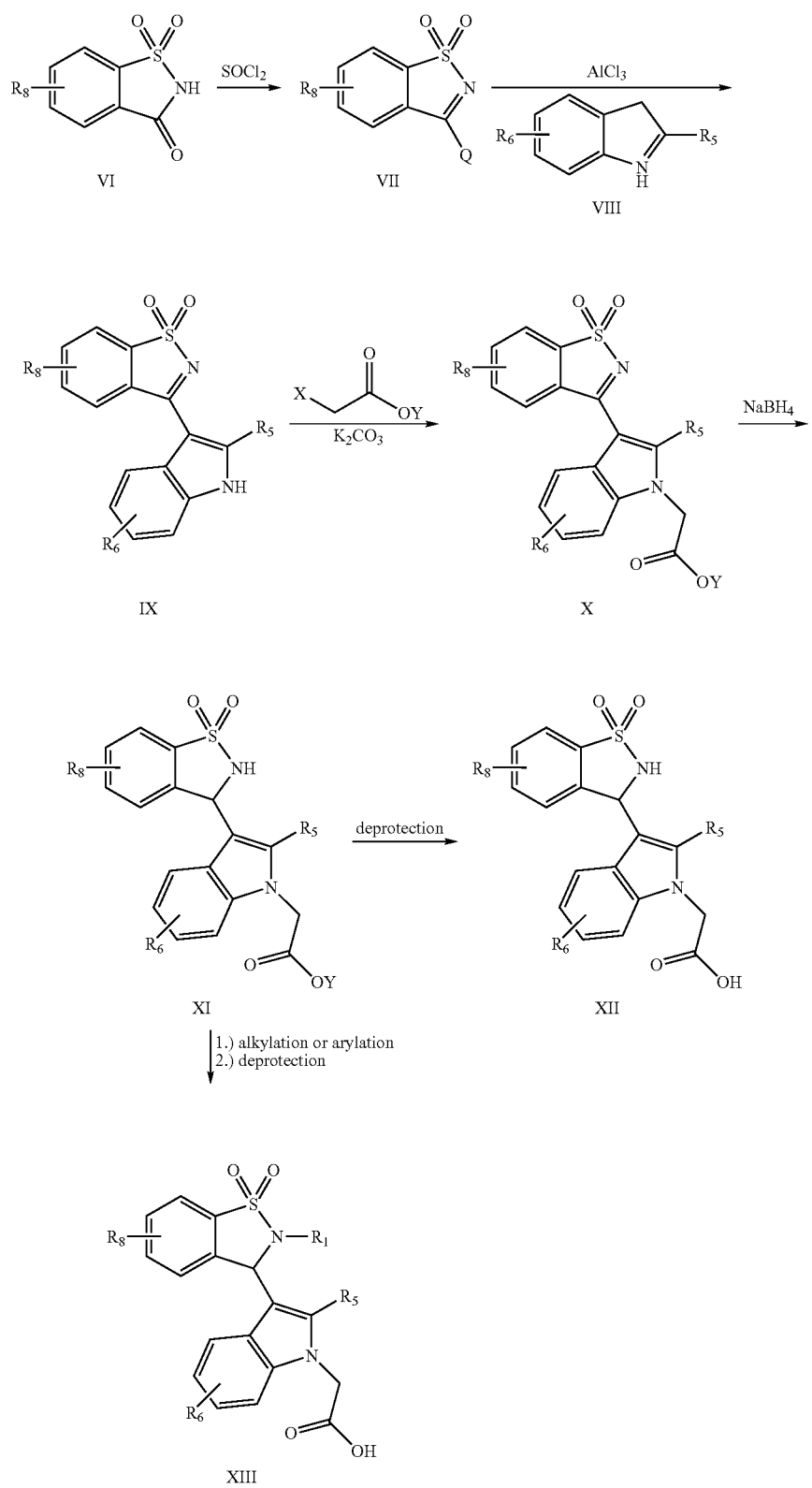

wherein R$_8$ is H, halo, C$_{1-10}$ alkoxy, cyano, C$_{1-10}$ alkyl, C$_{2-10}$ alkenyl, C$_{2-10}$ alkynyl, C$_{1-10}$ alkylaryl, C$_{1-10}$ alkylheteroaryl, —C$_{1-10}$ alkyl-O—C$_{1-10}$ alkyl, —C$_{1-10}$ alkyl-O-aryl, —C$_{1-10}$ alkyl-O-heteroaryl, aryl, or heteroaryl;

Q is a halogen;

X is a halogen; and

Y is a protecting group, such as alkyl (e.g., t-butyl).

Indole benzothiadiazines may be prepared by Scheme 2:

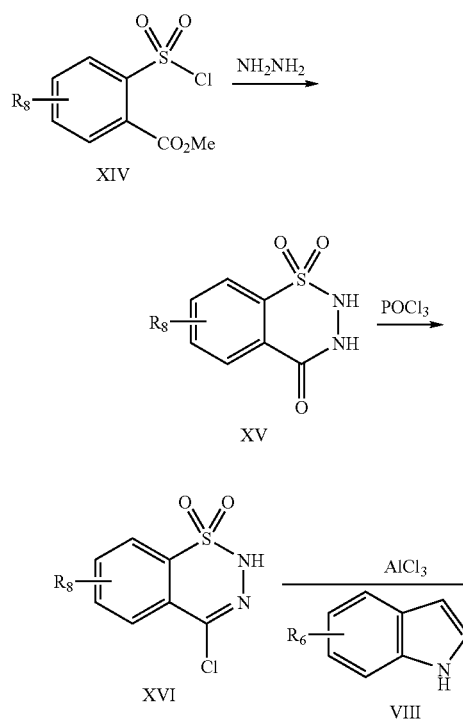

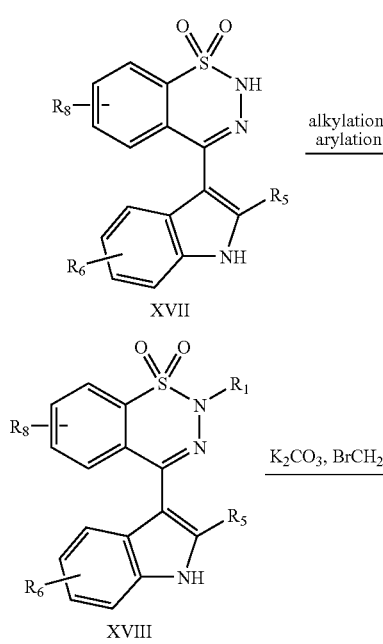

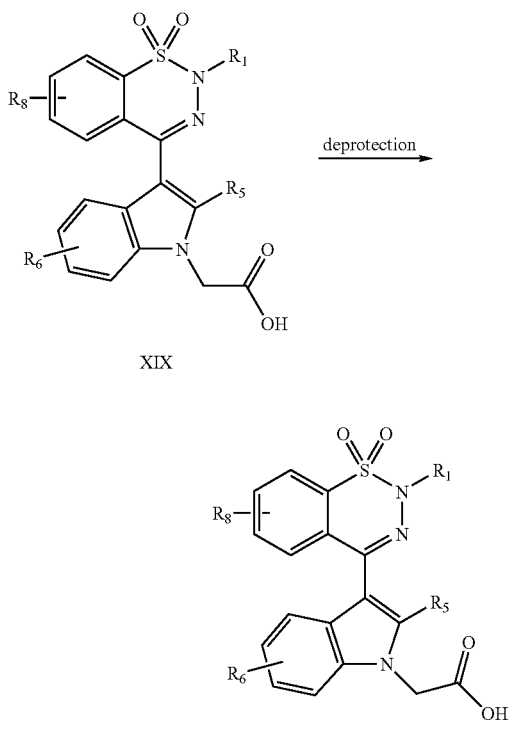

wherein R$_8$ is H, halo, C$_{1-10}$ alkoxy, cyano, C$_{1-10}$ alkyl, C$_{2-10}$ alkenyl, C$_{2-10}$ alkynyl, C$_{1-10}$ alkylaryl, C$_{1-10}$ alkylheteroaryl, —C$_{1-10}$ alkyl-O—C$_{1-10}$ alkyl, —C$_{1-10}$ alkyl-O-aryl, —C$_{1-10}$ alkyl-O-heteroaryl, aryl, or heteroaryl; and Y is a protecting group, such as alkyl (e.g., t-butyl).

Indole quinazolinones may be prepared by Scheme 3:

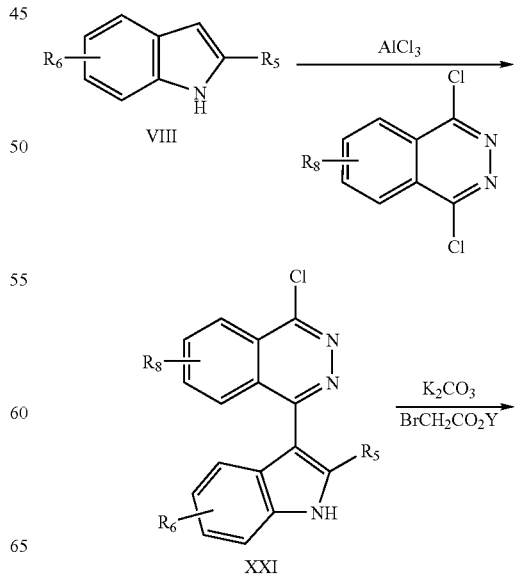

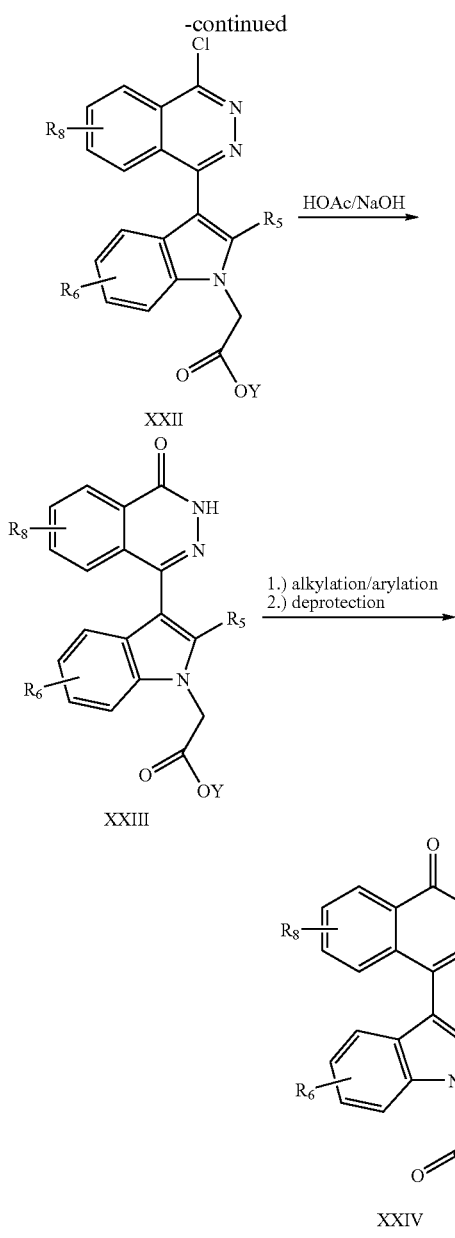

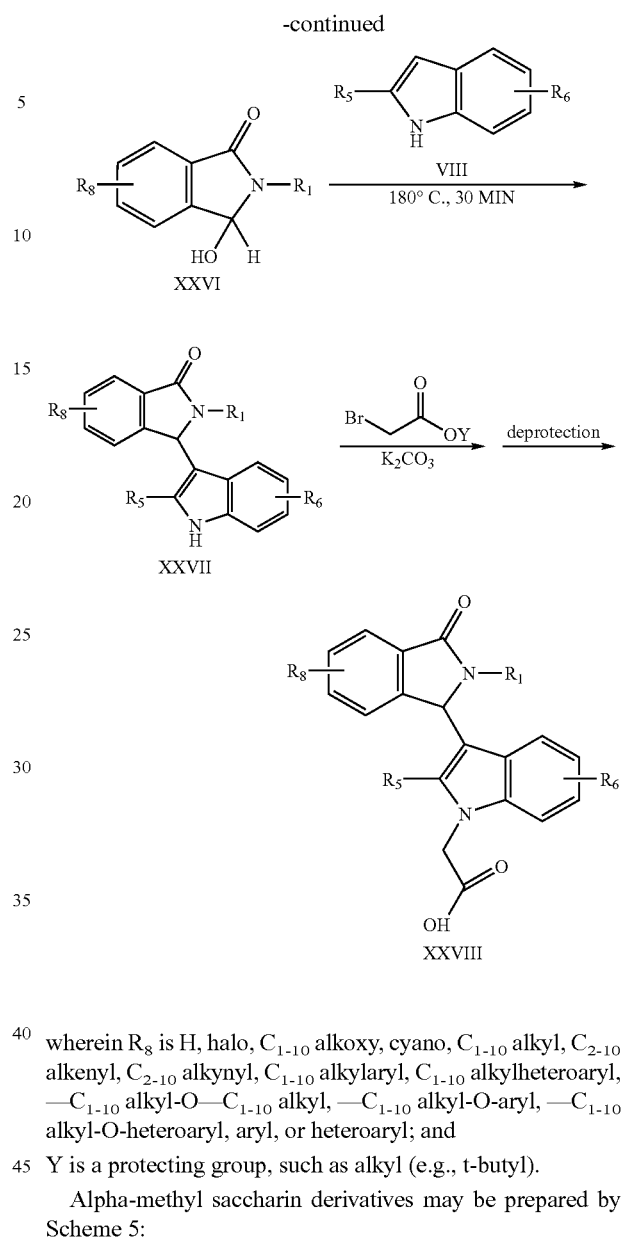

wherein $R_8$ is H, halo, $C_{1-10}$ alkoxy, cyano, $C_{1-10}$ alkyl, $C_{2-10}$ alkenyl, $C_{2-10}$ alkynyl, $C_{1-10}$ alkylaryl, $C_{1-10}$ alkylheteroaryl, —$C_{1-10}$ alkyl-O—$C_{1-10}$ alkyl, —$C_{1-10}$ alkyl-O-aryl, —$CO_{1-10}$ alkyl-O-heteroaryl, aryl, or heteroaryl; and Y is a protecting group, such as alkyl (e.g. t-butyl).

Indole isoindolones may be prepared by Scheme 4:

Scheme 4.

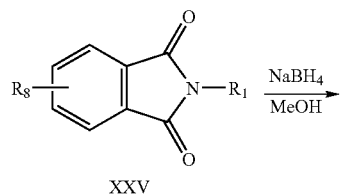

wherein $R_8$ is H, halo, $C_{1-10}$ alkoxy, cyano, $C_{1-10}$ alkyl, $C_{2-10}$ alkenyl, $C_{2-10}$ alkynyl, $C_{1-10}$ alkylaryl, $C_{1-10}$ alkylheteroaryl, —$C_{1-10}$ alkyl-O—$C_{1-10}$ alkyl, —$C_{1-10}$ alkyl-O-aryl, —$C_{1-10}$ alkyl-O-heteroaryl, aryl, or heteroaryl; and Y is a protecting group, such as alkyl (e.g., t-butyl).

Alpha-methyl saccharin derivatives may be prepared by Scheme 5:

Scheme 5.

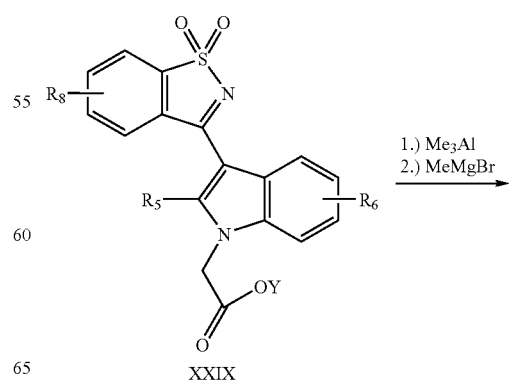

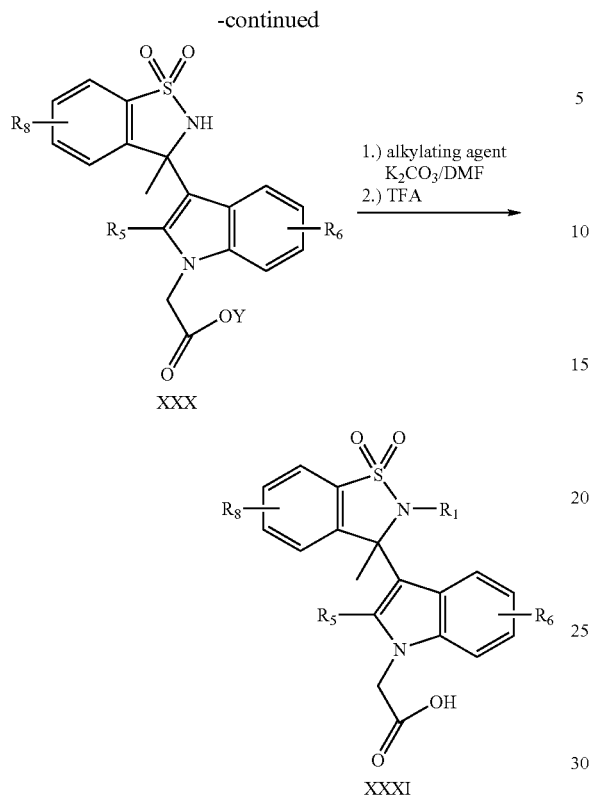
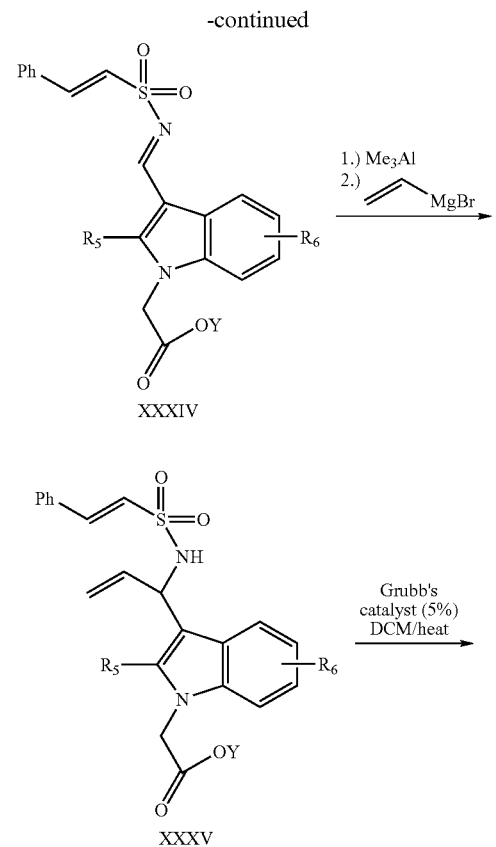
wherein Y is a protecting group, such as alkyl (e.g., t-butyl); and
$R_8$ is H, halo, $C_{1-10}$ alkoxy, cyano, $C_{1-10}$ alkyl, $C_{2-10}$ alkenyl, $C_{2-10}$ alkynyl, $C_{1-10}$ alkylaryl, $C_{1-10}$ alkylheteroaryl, —$C_{1-10}$ alkyl-O—$C_{1-10}$ alkyl, —$C_{1-10}$ alkyl-O-aryl, —$C_{1-10}$ alkyl-O-heteroaryl, aryl, or heteroaryl.
Des-benzo saccharin derivatives may be prepared by Scheme 6:
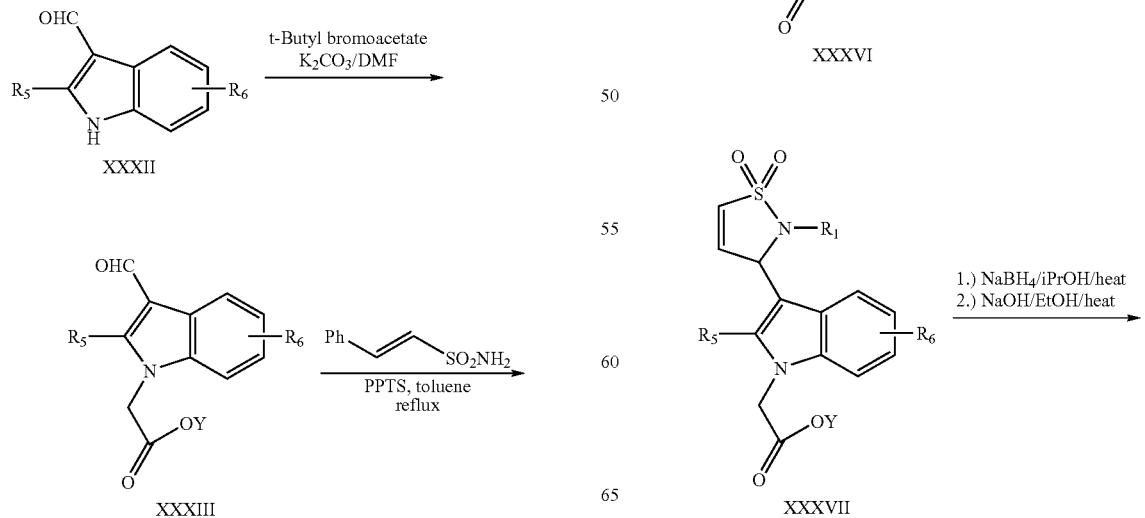

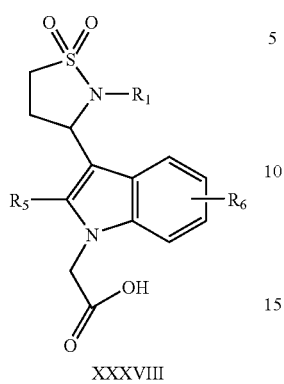

XXXVIII wherein Y is a protecting group, such as alkyl (e.g., t-butyl).

Dihydro-pyridazinone derivatives may be prepared by Scheme 7:

Scheme 7.

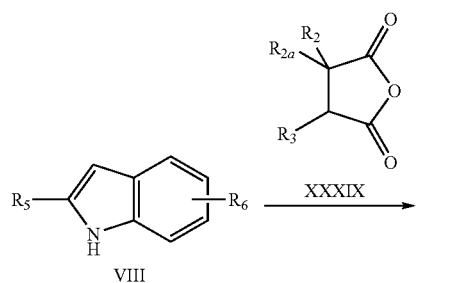

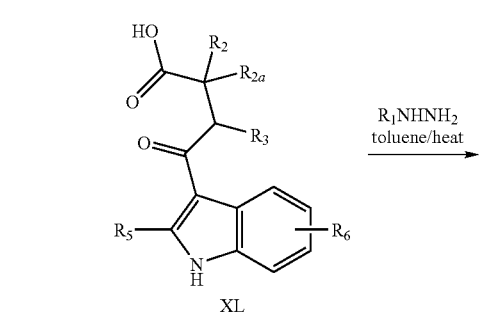

XL

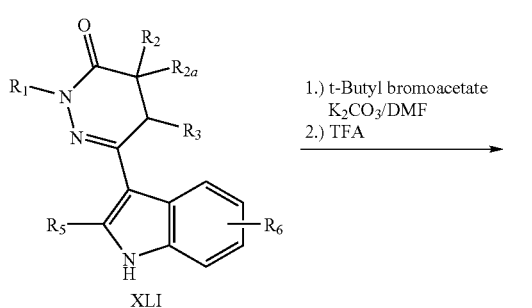

XLI

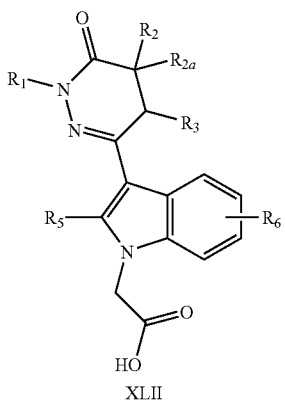

XLII

In one embodiment, the invention relates to a method of preparing a compound having formula XII or XIII, comprising a) halogenating a compound having formula VI with a halogenating agent (e.g., $SOCl_2$) in a solvent or mixture of solvents (e.g., dioxane and dimethylformamide (DMF)) at elevated temperature (e.g., about 80-120° C.) for a sufficient time (e.g., overnight) to form a compound having formula VII, where Q is a halogen (e.g., Cl), which is then isolated (e.g., concentrated to dryness and recrystallized) (see, e.g., U.S. Pat. No. 4,140,693);

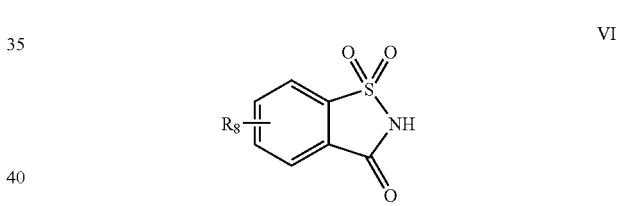

VI

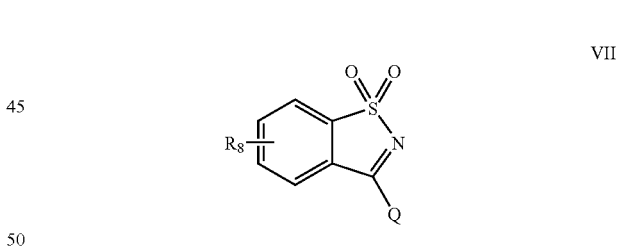

VII b) condensing a compound having formula VII with an indole compound VIII in the presence of a Lewis acid (e.g., $AlCl_3$) in a polar solvent (e.g., 1,2-dichloroethane) at elevated temperature (e.g., about 65° C.) for a sufficient time (e.g., overnight) to form a compound having formula IX, which is then isolated (e.g., the reaction is cooled and quenched with water, filtered, washed, and dried);

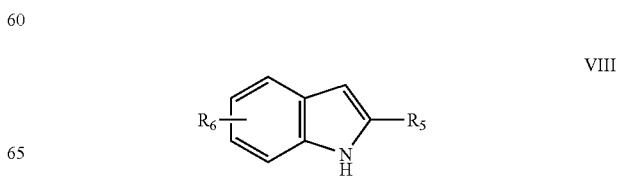

VIII

-continued

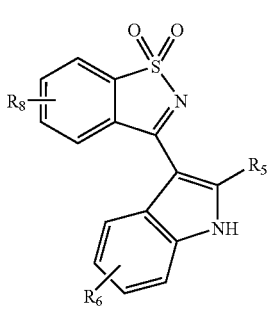

IX c) alkylating a compound having formula IX with a halogenated acetic acid alkyl ester (e.g., t-butyl bromoacetate) in a solvent (e.g., DMF) in the presence of a base (e.g., K₂CO₃) at elevated temperature (e.g., about 80-100° C.) for a sufficient time (e.g., several hours) to form a compound having formula X, which is then isolated (e.g. extracted, dried, and concentrated);

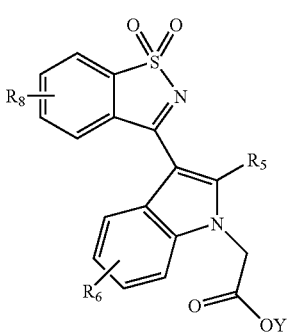

X d) reducing a compound having formula X with a reducing agent (e.g., NaBH₄) in a polar solvent (e.g., methanol) at about room temperature to form a compound having formula XI, which is then isolated (e.g., quenched with an organic acid (e.g., acetic acid), extracted with an organic solvent (e.g., dichloromethane (DCM)), dried and concentrated);

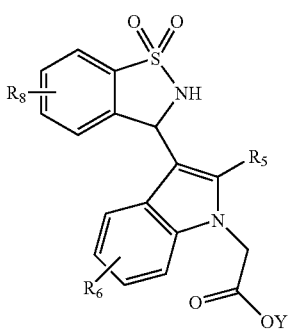

XI e) deprotecting a compound having formula XI e.g., with an organic acid (e.g., trifluoroacetic acid (TFA)) at about room temperature, to form a compound having formula XII, which is then isolated (e.g. concentrated to dryness and purified by preparative liquid chromatography/mass spectrometry (LCMS)); or

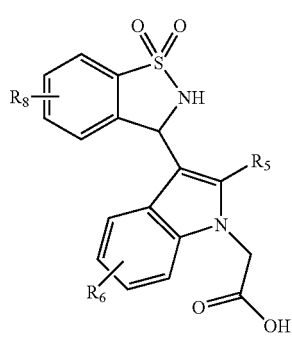

XII f) alkylating or arylating a compound having formula XI followed by deprotecting to form a compound having formula XIII, which is then isolated (e.g., concentrated to dryness and purified by LCMS).

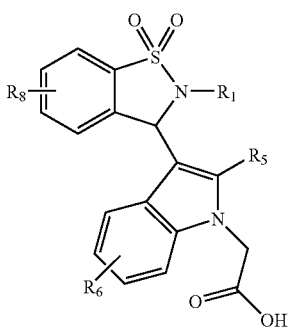

XIII

In one embodiment, the invention relates to a method of preparing a compound having formula XII or XIII, comprising deprotecting a compound having formula XI to form a compound having formula XII; or

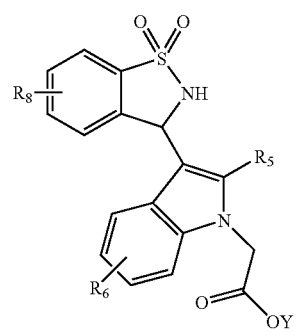

XI

-continued

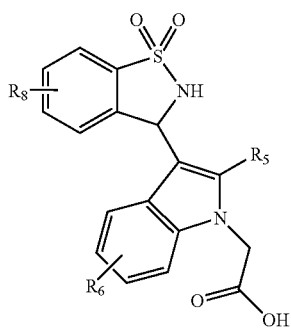

XII alkylating or arylating a compound having formula XI followed by deprotecting to form a compound having formula XIII.

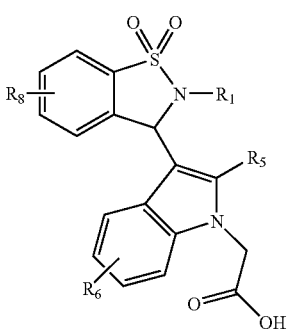

XIII

In one embodiment, the invention relates to a method of preparing a compound having formula XIX or XX, comprising a) condensing a compound having formula XIV with hydrazine e.g., in a non-polar solvent (e.g., ether) at about room temperature followed by an organic acid (e.g., acetic acid) to form a compound having formula XV, which is then isolated (e.g., washed with water, dried, and concentrated);

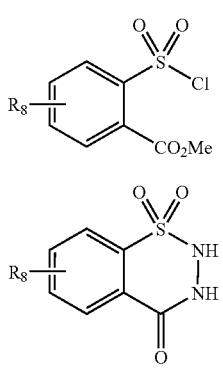

XIV

XV b) halogenating a compound having formula XV with a halogenating agent (e.g., POCl$_3$) e.g., at elevated temperature (e.g., about 80-100° C.) for a sufficient time (e.g., several hours) to form a compound having formula XVI, wherein Q is a halogen (e.g., Cl), which is then isolated (e.g., quenched with ice, extracted with a non-polar solvent (e.g., DCM), dried, and concentrated);

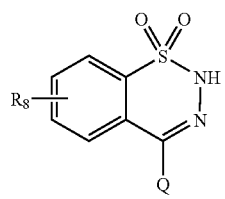

XVI c) condensing a compound having formula XVI with an indole compound VIII in the presence of a Lewis acid (e.g., AlCl$_3$) in a polar solvent (e.g., 1,2-dichloroethane) e.g., at elevated temperature (e.g., about 65-70° C.) for a sufficient time (e.g., overnight) to form a compound having formula XVII, which is then isolated (e.g., cooled and quenched with ice, extracted with an organic solvent and purified by chromatography);

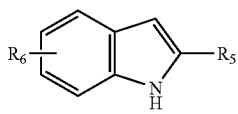

VIII

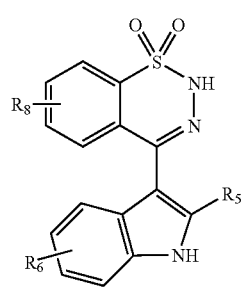

XVII d) alkylating or arylating a compound having formula XVII to form a compound having formula XVIII, which is then isolated (e.g., extracted and concentrated to dryness and purified by preparative LCMS);

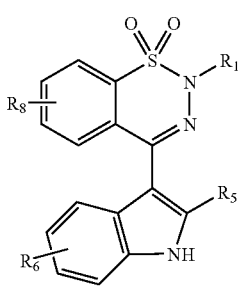

XVIII e) alkylating a compound having formula XVIII with a halogenated acetic acid alkyl ester (e.g., t-butyl bromoacetate) in a solvent (e.g. DMF) in the presence of a base (e.g., K$_2$CO$_3$) e.g. at elevated temperature (e.g., about 75-100° C.) for a sufficient time (e.g., several hours) to form a compound having formula XIX, which is then isolated (e.g., extracted and concentrated to dryness); and

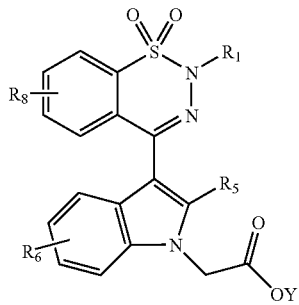
XIX f) deprotecting a compound having formula XIX e.g., with an organic acid (e.g., TFA) e.g., at about room temperature to form a compound having formula XX, which is then isolated (e.g., concentrated to dryness and purified by preparative LCMS).

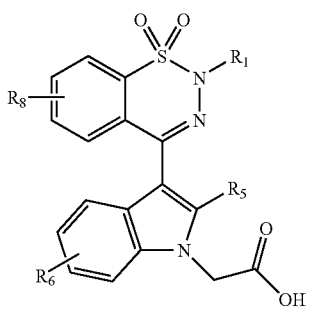
XX

In one embodiment, the invention relates to a method of preparing a compound having formula XX, comprising deprotecting a compound having formula XIX to form a compound having formula XX.

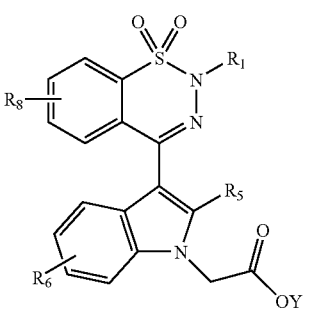
XIX

-continued

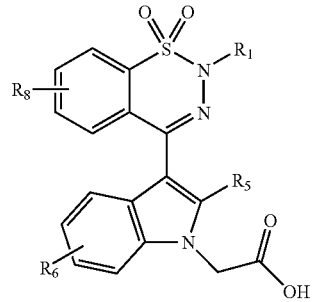
XX

In one embodiment, the invention relates to a method of preparing a compound having formula XXIV, comprising a) condensing a compound having formula VIII with a 1,4-dihalo phthalazine compound (e.g., 1,4-dichlorophthalazine) in the presence of a Lewis acid (e.g., AlCl₃) in a polar solvent (e.g., 1,2-dichloroethane) at elevated temperature (e.g., about 65° C.) for a sufficient time (e.g., overnight) to form a compound having formula XXI, wherein Q is halogen (e.g., Cl), which is then isolated (e.g., cooled and quenched with water, filtered, and dried);

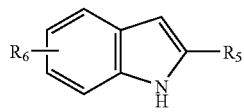
VIII

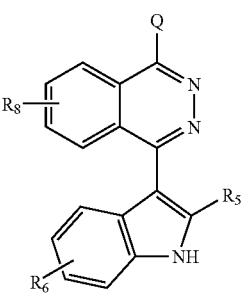
XXI b) alkylating a compound having formula XXI with a halogenated acetic acid ester (e.g., t-butyl bromoacetate) in a solvent (e.g., DMF) in the presence of a base (e.g., K₂CO₃) at about room temperature for several hours to form a compound having formula XXII;

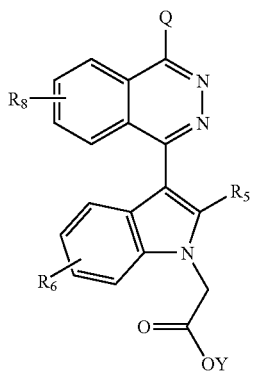

c) hydrolyzing a compound having formula XXII with an organic acid (e.g., acetic acid) e.g., in the presence of a base (e.g., NaOH) at elevated temperature (e.g., about 70° C.) for a sufficient time (e.g., several hours) to form a compound having formula XXIII, which is then isolated (e.g., cooled, extracted, dried, and concentrated); and

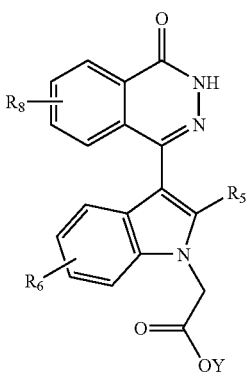

d) alkylating or arylating a compound having formula XXIII (e.g., with benzyl bromide) followed by deprotecting to form a compound having formula XXIV.

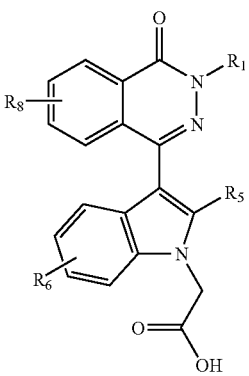

In one embodiment, the invention relates to a method of preparing a compound having formula XXIV, comprising alkylating or arylating a compound having formula XXIII followed by deprotecting to form a compound having formula XXIV.

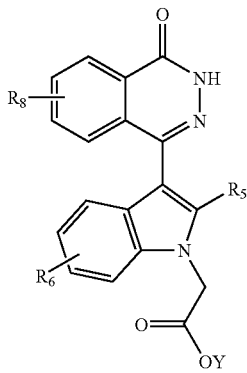

In one embodiment, the invention relates to a method of preparing a compound having formula XXVIII, comprising a) reducing a compound having formula XXV with a reducing agent (e.g., NaBH$_4$) in a polar solvent (e.g., methanol) e.g., at reduced temperature (e.g., about 0° C.) and then about room temperature to form a compound having formula XXVI, which is then isolated (e.g., quenched e.g., with an organic acid (e.g., acetic acid), extracted e.g., with a non-polar solvent (e.g., DCM), washed, and concentrated);

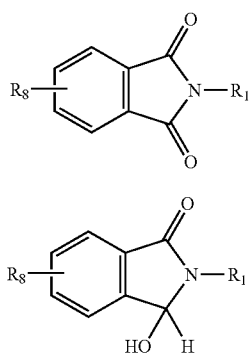

b) condensing a compound having formula XXVI with an indole compound VIII e.g., at elevated temperature (e.g., about 180° C.) for a sufficient time (e.g., about 30 minutes)

to form a compound having formula XXVII, which is then isolated (e.g., cooled and recrystallized (e.g., from ethanol/water)); and

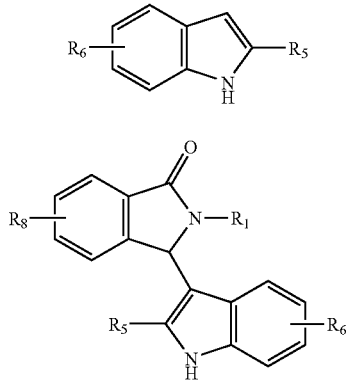

VIII

XXVII c) alkylating a compound having formula XXVII with a halogenated acetic acid alkyl ester (e.g., t-butyl bromoacetate) in a solvent (e.g., DMF) in the presence of a base (e.g., $K_2CO_3$) at elevated temperature (e.g., about 80-100° C.) for a sufficient time (e.g., several hours), followed by deprotection e.g., with an organic acid (e.g., TFA), to form a compound having formula XXVIII, which is then isolated (e.g., extracted to dryness and purified by LCMS).

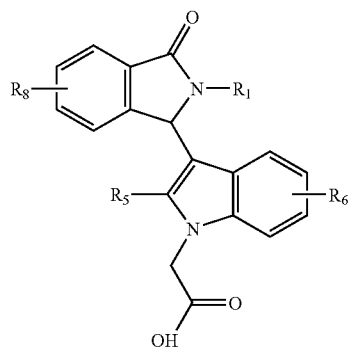

XXVIII

In one embodiment, the invention relates to a method of preparing a compound having formula XXVIII, comprising condensing a compound having formula XXVII with a halogenated acetic acid alkyl ester followed by deprotecting to form a compound having formula XXVIII.

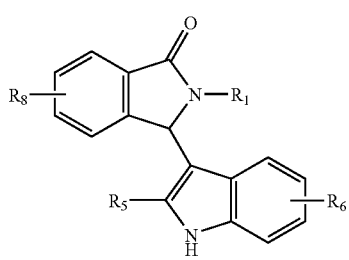

XXVII

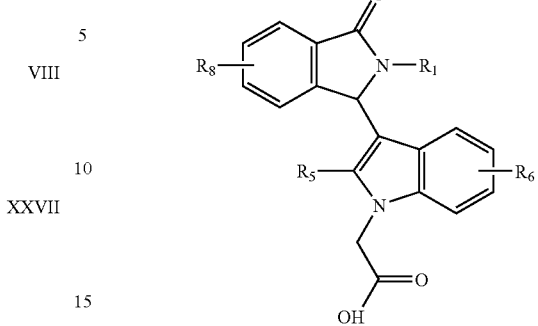

XXVIII

In one embodiment, the invention relates to a method of preparing a compound having formula XXXI, comprising a) methylating a compound having formula XXIX with a methylating agent (e.g., MeMgBr) in the presence of a Lewis acid (e.g., $Me_3Al$) at reduced temperature (e.g., 0° C.) to form a compound having formula XXX, which may then be isolated (e.g., extracted, dried, and purified by silica gel chromatography); and

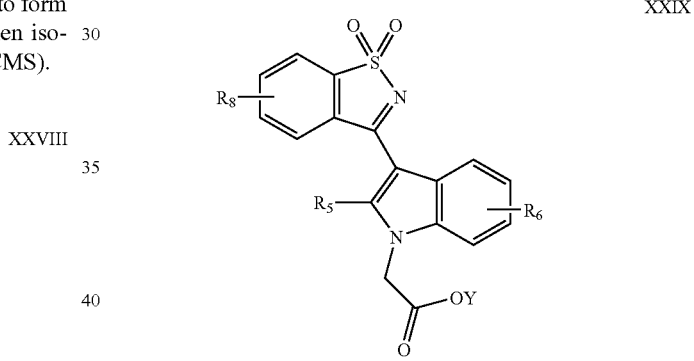

XXIX

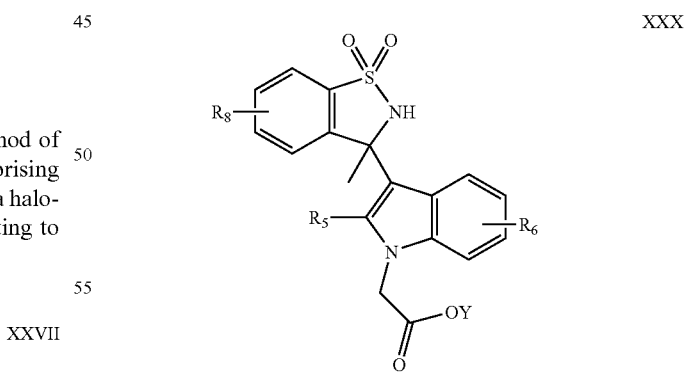

XXX b) alkylating or arylating a compound having formula XXX in a solvent (e.g., DMF) in the presence of a base (e.g., $K_2CO_3$) at elevated temperature (e.g., about 80-100° C.) for a sufficient time (e.g., several hours), followed by deprotection e.g., with an organic acid (e.g., TFA), to form a compound having formula XXXI, which is then isolated (e.g., extracted to dryness and purified by LCMS).

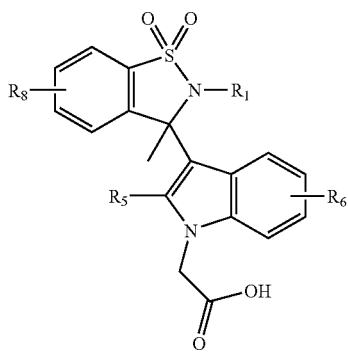

XXXI

In one embodiment, the invention relates to a method of preparing a compound having formula XXXI, comprising alkylating or arylating a compound having formula XXX to form a compound having formula XXXI.

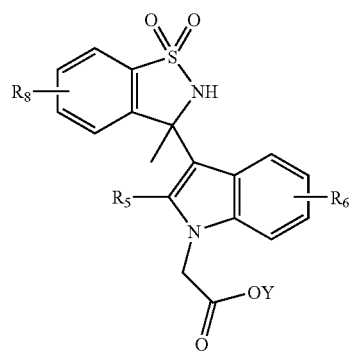

XXX

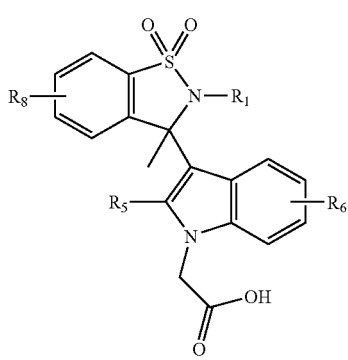

XXXI

In one embodiment, the invention relates to a method of preparing a compound having formula XXXVIII, comprising
a) alkylating a compound having formula XXXII with a halogenated acetic acid alkyl ester (e.g., t-butyl bromoacetate) in a solvent (e.g., DMF) in the presence of a base (e.g., $K_2CO_3$) at elevated temperature (e.g., about 80-100° C.) for a sufficient time (e.g., several hours) to form a compound having formula XXXIII, which may then be isolated (e.g., extracted, dried, and purified by silica gel chromatography);

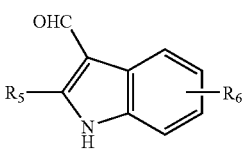

XXXII

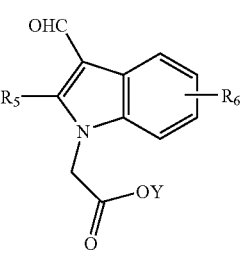

XXXIII b) condensing a compound having formula XXXIII with 2-phenylethenesulfonic acid amide in a solvent (e.g., toluene) at elevated temperature (e.g., about 80-100° C.) for a sufficient time (e.g., several hours) to form a compound having formula XXXIV, which may then be isolated (e.g., extracted, dried, and purified by silica gel chromatography);

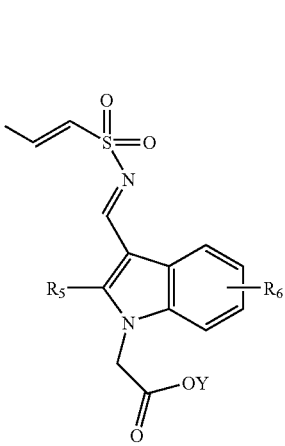

XXXIV c) alkylating a compound having formula XXXIV with an alkylating agent (e.g., $CH_2CHMgBr$) in the presence of a Lewis acid (e.g. $Me_3Al$) at room temperature for a sufficient time (e.g., 10-30 minutes) to form a compound having formula XXXV, which may then be isolated (e.g., extracted, dried, and purified by silica gel chromatography);

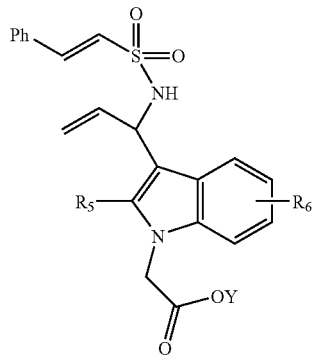

XXXV d) cyclizing a compound having formula XXXV in the presence of a catalyst (e.g., 5% Grubb's catalyst) in a solvent (e.g. DCM) at elevated temperature for a sufficient time (e.g., several hours) to form a compound having formula XXXVI, which is then isolated (e.g., by silica gel chromatography);

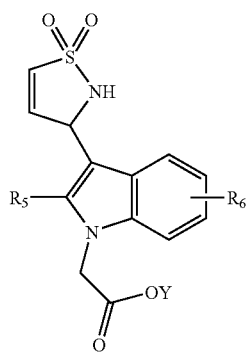

XXXVI e) alkylating or arylating a compound having formula XXXVI in a solvent (e.g., DMF) in the presence of a base (e.g., $K_2CO_3$) at elevated temperature (e.g., about 80-100° C.) for a sufficient time (e.g., several hours) to form a compound having formula XXXVII, which may then be isolated (e.g., extracted, dried, and purified by silica gel chromatography); and

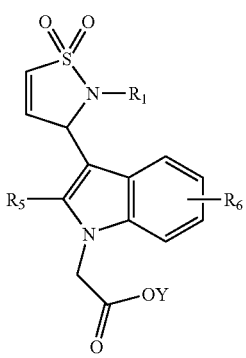

XXXVII f) reducing a compound having formula XXXVII with a reducing agent (e.g., $NaBH_4$) in a solvent (e.g., isopropanol) at elevated temperature, followed by deprotection with a base (e.g., NaOH) in a solvent (e.g., ethanol) at elevated temperature (e.g., about 80-100° C.) for a sufficient time (e.g., several hours) to form a compound having formula XXXVIII, which may then be isolated (e.g., extracted to dryness and purified by LCMS).

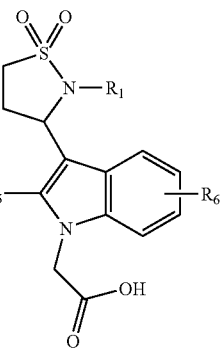

XXXVIII

In one embodiment, the invention relates to a method of preparing a compound having formula XXXVIII, comprising reducing a compound having formula XXXVII followed by deprotecting to form a compound having formula XXXVIII.

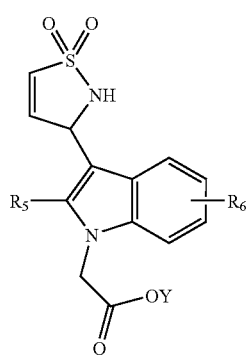

XXXVI

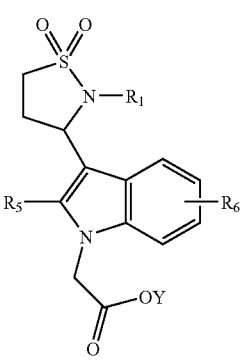

XXXVIII

In one embodiment, the invention relates to a method of preparing a compound having formula XLII, comprising a) acylating an indole compound having formula VIII with a compound having formula XXXIX in the presence of a Lewis acid (e.g., $AlCl_3$) (e.g., about 60-80° C.) for a sufficient time (e.g., several hours) to form a compound having formula XL;

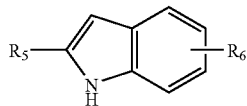 VIII

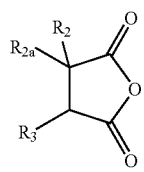 XXXIX

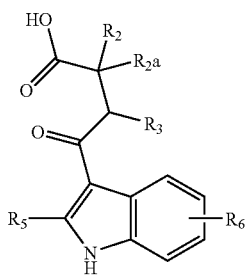 XL b) cyclizing a compound having formula XL with an alkyl-hydrazide (e.g., R$_1$NHNH$_2$) in a solvent (e.g., toluene) at elevated temperature for a sufficient time (e.g. several hours) to form a compound having formula XLI; and

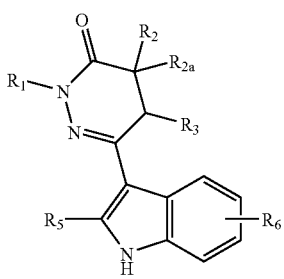 XLI c) alkylating a compound having formula XLI with a halogenated acetic acid alkyl ester (e.g., t-butyl bromoacetate) in a solvent (e.g., DMF) in the presence of a base (e.g., K$_2$CO$_3$) at elevated temperature (e.g., about 80-100° C.) for a sufficient time (e.g., several hours), followed by deprotection e.g., with an organic acid (e.g., TFA), to form a compound having formula XLII, which may then be isolated (e.g., extracted to dryness and purified by LCMS).

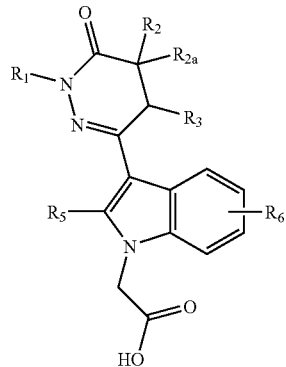 XLII

In one embodiment, the invention relates to a method of preparing a compound having formula XLII, comprising condensing a compound having formula XLI with a halogenated acetic acid alkyl ester followed by deprotecting to form a compound having formula XLII.

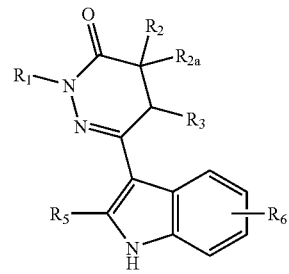 XLI

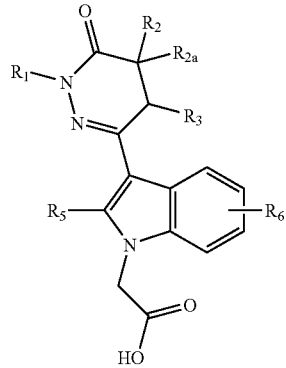 XLII

An important aspect of the present invention is that compounds of Formula I inhibit the binding of PGD$_2$ and its metabolites, as well as any other endogenous ligands, to the CRTH2 receptor. Therefore, it is contemplated that these compounds inhibit the effects of PGD$_2$ or its metabolites or other ligands on cells containing CRTH2 receptors. The inhibitors of the present invention can be used to block the effect of endogenous ligands of the CRTH2 receptor in any disorder that can be treated, ameliorated, or prevented by blocking the CRTH2 receptor. Thus, the present invention provides compositions and methods for targeting animals characterized as having elevated levels of PGD$_2$ or other endogenous ligands of the CRTH2 receptor. The present invention also contemplates methods of treating animals having normal levels of PGD$_2$ or other endogenous ligands of the CRTH2 receptor that would benefit from decreasing the effects of these molecules to sub-normal levels.

In some embodiments, the compositions and methods of the present invention are used to treat diseased cells, tissues, organs, or pathological conditions and/or disease states in an animal (e.g., a mammalian subject including, but not limited to, humans and veterinary animals). In this regard, various disorders, diseases and pathologies are amenable to treatment or prophylaxis using the present methods and compositions. A non-limiting list of these diseases and conditions includes, but is not limited to, disorders of the respiratory tract, including asthma, chronic obstructive pulmonary disease, bronchitis, rhinitis, nasal polyposis, sarcoidosis, farmer's lung, fibroid lung, idiopathic interstitial pneumonia, cystic fibrosis, and cough; disorders of the bones and joints, including arthritis, ankylosing spondylitis, Reiter's disease, Behcet's disease, Sjorgren's syndrome, and systemic sclerosis; disorders of the skin and eyes, including psoriasis, dermatitis, Lichen planus, pemphigus, epidermolysis bullosa, urticaria, angiodermas, vasculitides, erythemas, cutaneous eosinophilias, chronic skin ulcers, uveitis, corneal ulcers, and conjunctivitis; disorders of the gastrointestinal tract, including celiac disease, proctitis, gastroenteritis, mastocytosis, Crohn's disease, ulcerative colitis, irritable bowel disease, and food-related allergies; disorders of the central and peripheral nervous system, including Alzheimer's disease, amyotrophic lateral sclerosis, Creutzfeldt-Jacob's disease, AIDS dementia complex, Huntington's disease, Guillain-Barre syndrome, multiple sclerosis, encephalomyelitis, myasthenia gravis, tropical spastic paraparesis, CNS trauma, migraine, and stroke; disorders of other tissues and systemic disorders, including atherosclerosis, AIDS, lupus erythematosus, Hashimoto's thyroiditis, type I diabetes, nephrotic syndrome, eosinophilia fascitis, hyper IgE syndrome, leprosy, thrombocytopenia purpura, post-operative adhesions, sepsis, ischemic/reperfusion injury, hepatitis, glomerulonephritis, and chronic renal failure; and acute and chronic allograft rejection Some embodiments of the present invention provide methods for administering an effective amount of a compound of Formula I and at least one additional therapeutic agent. The additional therapeutic agent may be any therapeutic agent that has been used, is currently used, or is known to be useful for treating, ameliorating, or preventing a disorder encompassed by the present invention. For example, the additional therapeutic agent may be another compound that inhibits binding to the CRTH2 receptor (e.g., indomethacin). In another embodiment, the additional therapeutic drug is one that has a complementary effect to the compounds of the present invention. For a more detailed description of therapeutic agents, those skilled in the art are referred to instructive manuals including, but not limited to, the Physician's Desk Reference and to Goodman and Gilman's "Pharmaceutical Basis of Therapeutics" ninth edition, Eds. Hardman et al, 1996. The combination of a compound of the invention and one or more therapeutic agents can have additive potency or an additive therapeutic effect. The invention also encompasses synergistic combinations where the therapeutic efficacy is greater than additive. Preferably, such combinations also reduce or avoid unwanted or adverse effects. In certain embodiments, the combination therapies encompassed by the invention provide an improved overall therapy relative to administration of a compound of Formula I or any therapeutic agent alone. In certain embodiments, doses of existing or experimental therapeutic agents can be reduced or administered less frequently which increases patient compliance, thereby improving therapy and reducing unwanted or adverse effects.

Examples of useful therapeutic agents include, but are not limited to, agents used to treat asthma and rhinitis (steroids (e.g., budesomide), β2-receptor agonists (e.g., albuterol), leukotriene receptor antagonists (e.g., montelukast)), agents used to treat autoimmune disease (glucocorticoids, cyclosporine, tacrolimus, mycophenolate mofetil), agents used to treat nervous system disorders (anticholinesterases, dopamine, levodopa, serotonin receptor agonists (e.g., sumatriptan), amantadine, donepezil, riluzole), agents used to treat ischemia/reperfusion injury (nitroglycerin, nifedipine), and agents used to treat gastrointestinal disorders (neostigmine, metoclopramide, sulfasalazine).

In some embodiments of the present invention, a compound of Formula I and one or more therapeutic agents are administered to an animal at different periodicities, at different durations, at different concentrations, by different administration routes, etc. In some embodiments, the compound is administered prior to the therapeutic agent, e.g. 0.5, 1, 2 3, 4, 5, 10, 12, or 18 hours, 1, 2, 3, 4, 5, or 6 days, 1, 2, 3, or 4 weeks prior to the administration of the therapeutic agent. In some embodiments, the compound is administered after the therapeutic agent, e.g., 0.5, 1, 2 3, 4, 5, 10, 12, or 18 hours, 1, 2, 3, 4, 5, or 6 days, 1, 2, 3, or 4 weeks after the administration of the therapeutic agent. In some embodiments, the compound and the therapeutic agent are administered concurrently but on different schedules, e.g., the compound is administered daily while the therapeutic agent is administered once a week, once every two weeks, once every three weeks, or once every four weeks. In other embodiments, the compound is administered once a week while the therapeutic agent is administered daily, once a week, once every two weeks, once every three weeks, or once every four weeks.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to animals, e.g. humans, orally at a dose of 0.0025 to 50 mg/kg, or an equivalent amount of the pharmaceutically acceptable salt thereof, per day of the body weight of the animal being treated for disorders responsive to inhibition of the CRTH2 receptor. Preferably, about 0.01 to about 10 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, and most preferably, from about 0.01 to about 5 mg/kg.

The unit oral dose may comprise from about 0.01 to about 50 mg, preferably about 0.1 to about 10 mg of the compound. The unit dose may be administered one or more times daily as one or more tablets or capsules each containing from about 0.1 to about 10 mg, conveniently about 0.25 to 50 mg of the compound.

In a topical formulation, the compound may be present at a concentration of about 0.01 to 100 mg per gram of carrier. In a preferred embodiment, the compound is present at a concentration of about 0.07-1.0 mg/ml, more preferably, about 0.1-0.5 mg/ml, most preferably, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally or topically and which can be used for the preferred type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by injection, topically or orally, contain from about 0.01 to 99 percent, preferably from about 0.25 to 75 percent of active compound(s), together with the excipient.

The pharmaceutical compositions of the invention may be administered to any animal which may experience the beneficial effects of the compounds of the invention. Foremost among such animals are mammals, e.g., humans, although the invention is not intended to be so limited. Other animals include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal, or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

Lotions may be conveniently prepared by dissolving the active ingredient, in a suitable high molecular weight alcohol such as propylene glycol or polyethylene glycol.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

General Analytical Conditions:

HPLC analysis and purification was performed using a Waters 2525 binary gradient pump, Waters 2767 sample manager, Waters 2487 UV detector (220 and 254 nM), and Waters Micromass ZQ electrospray mass spec detector. The Micromass ZQ was set for both positive and negative ionization (cone voltage=25 and 50, respectively).

Analytical HPLC analysis was performed as follows:
Waters XTerra MS C18 50×4.6 mm 3.5 μm column
Mobile Phase: 10 mM Ammonium Acetate buffer at pH 5.75 and Acetonitrile
Acetonitrile: 10 to 75% at 3.5 minutes, 75 to 99% at 3.9 minutes, 99% hold to 4.2 minutes, 99 to 10% at 4.5 minutes, re-equilibrate.

Preparative HPLC was performed as follows:
Waters XTerra Prep MS C18 50×19 mm 5 μm column
Mobile Phase: 10 mM Ammonium Acetate buffer at pH 5.75 and Acetonitrile
Acetonitrile: 10 to 99% at 8 minutes, 99% hold to 9 minutes, 99 to 10% at 9.5 minutes, re-equilibrate.

NMR analysis was performed using a Bruker BioSpin UltraSheild NMR (300 MHz).

EXAMPLE 1

[3-(1,1-Dioxo-2,3-dihydro-1H-1$\lambda^6$-benzo[d]isothiazol-3-yl)-indol-1-yl]-acetic Acid a.) 3-Chloro-benzo[d]isothiazole 1,1-dioxide (Wade et al., U.S. Pat. No. 4,140,693) (Scheme 1)

Saccharin (10 g) was treated sequentially with dioxane (40 mL), thionyl chloride (15 mL) and DMF (0.4 mL). The resulting suspension was heated to reflux for 24 hours. The reaction mixture was concentrated to dryness and recrystallized from 60 mL toluene to give 5.7 g of the sub-title compound as a white solid.

b.) 3-(1H-Indol-3-yl)-benzo[d]isothiazole 1,1-dioxide

Indole (117 mg, 1 mmol) and 3-chloro-benzo[d]isothiazole 1,1-dioxide (201 mg, 1 mmol) were treated 5 mL of 1,2-dichloroethane followed by AlCl$_3$ (160 mg, 1.2 mmol). The reaction mixture was heated to 65° C. overnight, then cooled and quenched with water (1 mL). The resulting solid was filtered, washed with water, and dried to give 0.3 grams of the sub-title compound. MS: ESI (negative): 281 (M–H).

c.) [3-(1,1-Dioxo-1H-1$\lambda^6$-benzo[d]isothiazol-3-yl)-indol-1-yl]-acetic Acid tert-butyl Ester A solution of the product from example 1, step b (300 mg) was dissolved in DMF and treated with K$_2$CO$_3$ (166 mg, 1.2 mmol) followed by t-butyl bromoacetate (150 μL, 1 mmol). The reaction was heated to 80° C. for 1 h. Additional K$_2$CO$_3$ and t-butyl bromoacetate were added (1 mmol each) and the reaction was heated to 100° C. for 2 h. The reaction was cooled and partitioned between EtOAc and water. The organic layer was washed with water 3 times then dried over MgSO$_4$ and concentrated to give the sub-title compound as a yellow solid. MS: ESI (positive): 397 (M+H).

d.) [3-(1,1-Dioxo-2,3-dihydro-1H-1$\lambda^6$-benzo[d]isothiazol-3-yl)-indol-1-yl]-acetic Acid tert-butyl Ester A solution of the product from example 1, step c (100 mg, 0.25 mmol) was dissolved in 4 mL MeOH. NaBH$_4$ (30 mg, 0.75 mmol) was added and the reaction was stirred at rt for ½ h. Additional NaBH$_4$ was added as needed in order to push the reaction to completion. The reaction was carefully quenched with HOAc until the evolution of hydrogen ceased. The resulting solution was partitioned between dichloromethane (DCM) and H$_2$O. The organic layer was dried over MgSO$_4$ and concentrated to an orange oil that was used without further purification. MS: ESI (negative): 397 (M–H).

e.) [3-(1,1-Dioxo-2,3-dihydro-1H-1$\lambda^6$-benzo[d]isothiazol-3-yl)-indol-1-yl]-acetic Acid The product of example 1, step d (32 mg, 0.08 mmol) was treated with trifluoroacetic acid (TFA) (neat) or 70% TFA in DCM. After stirring 2-24 h, the reaction was concentrated to dryness and purified by preparative LCMS to give the title compound. $^1$H NMR (DMSO-d$_6$) δ 7.90-7.86 (m, 1H), 7.66-7.57 (m, 2H), 7.38 (s, 1H), 7.29 (d, J=8.1 Hz, 1H), 7.25-7.20 (m, 2H), 7.06 (t, J=7.2 Hz, 1H), 6.87 (t, J=7.2 Hz, 1H), 6.07 (s, 1H), 4.62 (s, 2H); MS: ESI (negative): 341 (M–H).

EXAMPLE 2

[3-(1,1-Dioxo-2,3-dihydro-1H-1$\lambda^6$-benzo[d]isothiazol-3-yl)-5-methyl-indol-1-yl]-acetic Acid a.) 3-(5-Methyl-1H-indol-3-yl)-benzo[d]isothiazole 1,1-dioxide (Scheme 1)

The sub-title compound was prepared as described for example 1, step b) using 5-methyl indole.

b.) [3-(1,1-Dioxo-1H-1$\lambda^6$-benzo[d]isothiazol-3-yl)-5-methyl-indol-1-yl]-acetic Acid tert-butyl Ester The sub-title compound was prepared as described for example 1, step c) using the product from step a).

c.) [3-(1,1-Dioxo-2,3-dihydro-1H-1$\lambda^6$-benzo[d]isothiazol-3-yl)-5-methyl-indol-1-yl]-acetic Acid tert-butyl Ester The sub-title compound was prepared as described for example 1, step d) using the product from step b).

d.) [3-(1,1-Dioxo-2,3-dihydro-1H-1$\lambda^6$-benzo[d]isothiazol-3-yl)-5-methyl-indol-1-yl]-acetic Acid The title compound was prepared as described for example 1, step e) using the product from step c). MS: ESI (negative): 355 (M–H).

EXAMPLE 3

[3-(1,1-Dioxo-2,3-dihydro-1H-1$\lambda^6$-benzo[d]isothiazol-3-yl)-2-methyl-indol-1-yl]-acetic Acid a.) 3-(2-Methyl-1H-indol-3-yl)-benzo[d]isothiazole 1,1-dioxide (Scheme 1)

The sub-title compound was prepared as described for example 1, step b) using 2-methyl indole. The product did not crystallize upon quenching, and was instead purified by partitioning between DCM and water.

b.) [3-(1,1-Dioxo-1H-1λ⁶-benzo[d]isothiazol-3-yl)-2-methyl-indol-1-yl]-acetic Acid tert-butyl Ester The sub-title compound was prepared as described for example 1, step c) using the product from step a). This compound was purified by chromatography (EtOAc/Hex) prior to use in subsequent steps.

c.) [3-(1,1-Dioxo-2,3-dihydro-1H-1λ⁶-benzo[d]isothiazol-3-yl)-2-methyl-indol-1-yl]-acetic Acid tert-butyl Ester The sub-title compound was prepared as described for example 1, step d) using the product from step b).

d.) [3-(1,1-Dioxo-2,3-dihydro-1H-1λ⁶-benzo[d]isothiazol-3-yl)-2-methyl-indol-1-yl]-acetic Acid The title compound was prepared as described for example 1, step e) using the product from step c). MS: ESI (negative): 355 (M–H).

EXAMPLE 4

[3-(1,1-Dioxo-2,3-dihydro-1H-1λ⁶-benzo[d]isothiazol-3-yl)-5-methoxy-indol-1-yl]-acetic Acid a.) 3-(5-Methoxy-1H-indol-3-yl)-benzo[d]isothiazole 1,1-dioxide (Scheme 1)

The sub-title compound was prepared as described for example 1, step b) using 5-methoxy indole.

b.) [3-(1,1-Dioxo-1H-1λ⁶-benzo[d]isothiazol-3-yl)-5-methoxy-indol-1-yl]-acetic Acid tert-butyl Ester The sub-title compound was prepared as described for example 1, step c) using the product from step a).

c.) [3-(1,1-Dioxo-2,3-dihydro-1H-1λ⁶-benzo[d]isothiazol-3-yl)-5-methoxy-indol-1-yl]-acetic Acid tert-butyl Ester The sub-title compound was prepared as described for example 1, step d) using the product from step b).

d.) [3-(1,1-Dioxo-2,3-dihydro-1H-1λ⁶-benzo[d]isothiazol-3-yl)-5-methoxy-indol-1-yl]-acetic Acid The title compound was prepared as described for example 1, step e) using the product from step c). MS: ESI (negative): 371 (M–H).

EXAMPLE 5

[5-Chloro-3-(1,1-dioxo-2,3-dihydro-1H-1λ⁶-benzo[d]isothiazol-3-yl)-indol-1-yl]-acetic Acid a.) 3-(5-Chloro-1H-indol-3-yl)-benzo[d]isothiazole 1,1-dioxide (Scheme 1)

The sub-title compound was prepared as described for example 1, step b) using 5-chloro indole.

b.) [5-Chloro-3-(1,1-dioxo-1H-1λ⁶-benzo[d]isothiazol-3-yl)-indol-1-yl]-acetic Acid tert-butyl Ester The sub-title compound was prepared as described for example 1, step c) using the product from step a).

c.) [5-Chloro-3-(1,1-dioxo-2,3-dihydro-1H-1λ⁶-benzo[d]isothiazol-3-yl)-indol-1-yl]-acetic Acid tert-butyl Ester The sub-title compound was prepared as described for example 1, step d) using the product from step b).

d.) [5-Chloro-3-(1,1-dioxo-2,3-dihydro-1H-1λ⁶-benzo[d]isothiazol-3-yl)-indol-1-yl]-acetic Acid The product from step c) (100 mg) was dissolved in 3 mL EtOH and treated with 0.5 mL of 1 M NaOH. The reaction was heated to 50° C. for 2 h. Upon cooling, the reaction was washed with DCM, acidified with 1 M HCl, and extracted into DCM. The organic layer was washed twice with water, dried over MgSO₄, and concentrated to give the title compound as a solid. MS: ESI (negative): 375, 377 (M–H).

EXAMPLE 6

[5-Chloro-3-(1,1-dioxo-2,3-dihydro-1H-1λ⁶-benzo[d]isothiazol-3-yl)-2-methyl-indol-1-yl]-acetic Acid a.) 3-(5-Chloro-2-methyl-1H-indol-3-yl)-benzo[d]isothiazole 1,1-dioxide (Scheme 1)

The sub-title compound was prepared as described for example 1, step b) using 5-chloro-2-methyl indole.

b.) [5-Chloro-3-(1,1-dioxo-1H-1λ⁶-benzo[d]isothiazol-3-yl)-2-methyl-indol-1-yl]-acetic Acid tert-butyl Ester The sub-title compound was prepared as described for example 1, step c) using the product from step a).

c.) [5-Chloro-3-(1,1-dioxo-2,3-dihydro-1H-1λ⁶-benzo[d]isothiazol-3-yl)-2-methyl-indol-1-yl]-acetic Acid tert-butyl Ester The sub-title compound was prepared as described for example 1, step d) using the product from step b).

d.) [5-Chloro-3-(1,1-dioxo-2,3-dihydro-1H-1λ⁶-benzo[d]isothiazol-3-yl)-2-methyl-indol-1-yl]-acetic Acid The title compound was prepared as described for example 5, step d) using the product from step c). ¹H NMR (DMSO-d₆) 12.95 (bs, 1H), 7.93 (s, 1H), 7.93-7.90 (m, 1H), 7.64-7.57 (m, 2H), 7.40 (d, J=9.0 Hz, 1H), 7.07-7.04 (m, 1H), 7.00 (dd, J=2.1, 8.7 Hz, 1H), 6.92 (s, 1H), 6.16 (s, 1H), 5.00 (s, 2H), 2.39 (s, 3H); MS: ESI (negative): 389, 391 (M–H).

EXAMPLE 7

[3-(1,1-Dioxo-2,3-dihydro-1H-1λ⁶-benzo[d]isothiazol-3-yl)-2,5-dimethyl-indol-1-yl]-acetic Acid a.) 3-(2,5-Dimethyl-1H-indol-3-yl)-benzo[d]isothiazole 1,1-dioxide (Scheme 1)

The sub-title compound was prepared as described for example 1, step b) using 2,5-dimethyl indole.

b.) [3-(1,1-Dioxo-1H-1λ⁶-benzo[d]isothiazol-3-yl)-2,
5-dimethyl-indol-1-yl]-acetic Acid tert-butyl Ester The sub-title compound was prepared as described for example 1, step c) using the product from step a).

c.) [3-(1,1-Dioxo-2,3-dihydro-1H-1λ⁶-benzo[d]
isothiazol-3-yl)-2,5-dimethyl-indol-1-yl]-acetic Acid
tert-butyl Ester The sub-title compound was prepared as described for example 1, step d) using the product from step b).

d.) [3-(1,1-Dioxo-2,3-dihydro-1H-1λ⁶-benzo[d]
isothiazol-3-yl)-2,5-dimethyl-indol-1-yl]-acetic Acid The title compound was prepared as described for example 5, step d) using the product from step c). MS: ESI (negative): 369 (M−H).

EXAMPLE 8

[5-Bromo-3-(1,1-dioxo-2,3-dihydro-1H-1λ⁶-benzo
[d]isothiazol-3-yl)-indol-1-yl]-acetic Acid a.) 3-(5-Bromo-1H-indol-3-yl)-benzo[d]isothiazole
1,1-dioxide (Scheme 1)

The sub-title compound was prepared as described for example 1, step b) using 5-bromo indole.

b.) [5-Bromo-3-(1,1-dioxo-1H-1λ⁶-benzo[d]isothiazol-3-yl)-indol-1-yl]-acetic Acid tert-butyl Ester The sub-title compound was prepared as described for example 1, step c) using the product from step a).

c.) [5-Bromo-3-(1,1-dioxo-2,3-dihydro-1H-1λ⁶-
benzo[d]isothiazol-3-yl)-indol-1-yl]-acetic Acid tert-
butyl Ester The sub-title compound was prepared as described for example 1, step d) using the product from step b).

d.) [5-Bromo-3-(1,1-dioxo-2,3-dihydro-1H-1λ⁶-
benzo[d]isothiazol-3-yl)-indol-1-yl]-acetic Acid The title compound was prepared as described for example 5, step d) using the product from step c). MS: ESI (negative): 419, 421 (M−H).

EXAMPLE 9

[5-Cyano-3-(1,1-dioxo-2,3-dihydro-1H-1λ⁶-benzo
[d]isothiazol-3-yl)-indol-1-yl]-acetic Acid a.) 3-(1,1-Dioxo-1H-1λ⁶-benzo[d]isothiazol-3-yl)-
1H-indole-5-carbonitrile (Scheme 1)

The sub-title compound was prepared as described for example 1, step b) using 5-cyano indole.

b.) [5-Cyano-3-(1,1-dioxo-1H-1λ⁶-benzo[d]isothiazol-3-yl)-indol-1-yl]-acetic Acid tert-butyl Ester The sub-title compound was prepared as described for example 1, step c) using the product from step a).

c.) [5-Cyano-3-(1,1-dioxo-2,3-dihydro-1H-1λ⁶-
benzo[d]isothiazol-3-yl)-indol-1-yl]-acetic Acid tert-
butyl Ester The sub-title compound was prepared as described for example 1, step d) using the product from step b).

d.) [5-Cyano-3-(1,1-dioxo-2,3-dihydro-1H-1λ⁶-
benzo[d]isothiazol-3-yl)-indol-1-yl]-acetic Acid The title compound was prepared as described for example 5, step d) using the product from step c). MS: ESI (negative): 366 (M−H).

EXAMPLE 10

[3-(1,1-Dioxo-2,3-dihydro-1H-1λ⁶-benzo[d]isothia-
zol-3-yl)-5-fluoro-2-methyl-indol-1-yl]-acetic Acid a.) 3-(5-Fluoro-2-methyl-1H-indol-3-yl)-benzo[d]
isothiazole 1,1-dioxide (Scheme 1)

The sub-title compound was prepared as described for example 1, step b) using 5-fluoro-2-methyl indole.

b.) [3-(1,1-Dioxo-1H-1λ⁶-benzo[d]isothiazol-3-yl)-
5-fluoro-2-methyl-indol-1-yl]-acetic Acid tert-butyl
Ester The sub-title compound was prepared as described for example 1, step c) using the product from step a).

c.) [3-(1,1-Dioxo-2,3-dihydro-1H-1λ⁶-benzo[d]
isothiazol-3-yl)-5-fluoro-2-methyl-indol-1-yl]-acetic
Acid tert-butyl Ester The sub-title compound was prepared as described for example 1, step d) using the product from step b).

d.) [3-(1,1-Dioxo-2,3-dihydro-1H-1λ⁶-benzo[d]
isothiazol-3-yl)-5-fluoro-2-methyl-indol-1-yl]-acetic
Acid The title compound was prepared as described for example 5, step d) using the product from step c). MS: ESI (negative): 373 (M−H).

EXAMPLE 11

[4-Chloro-3-(1,1-dioxo-2,3-dihydro-1H-1λ⁶-benzo
[d]isothiazol-3-yl)-indol-1-yl]-acetic Acid a.) 3-(4-Chloro-1H-indol-3-yl)-benzo[d]isothiazole
1,1-dioxide (Scheme 1)

The sub-title compound was prepared as described for example 1, step b) using 4-chloro indole.

b.) [4-Chloro-3-(1,1-dioxo-1H-1λ⁶-benzo[d]isothia-
zol-3-yl)-indol-1-yl]-acetic Acid tert-butyl Ester The sub-title compound was prepared as described for example 1, step c) using the product from step a).

c.) [4-Chloro-3-(1,1-dioxo-2,3-dihydro-1H-1λ$^6$-benzo[d]isothiazol-3-yl)-2-methyl-indol-1-yl]-acetic Acid tert-butyl Ester The sub-title compound was prepared as described for example 1, step d) using the product from step b).

d.) [4-Chloro-3-(1,1-dioxo-2,3-dihydro-1H-1λ$^6$-benzo[d]isothiazol-3-yl)-indol-1-yl]-acetic Acid The title compound was prepared as described for example 5, step d) using the product from step c). $^1$H NMR (DMSO-d$_6$) δ 13.00 (bs, 1H), 8.34 (bd, J=4.2 Hz, 1H), 7.84 (d, J=7.5 Hz, 1H), 7.65 (t, J=7.0 Hz, 1H), 7.58 (t, J=7.2 Hz, 1H), 7.43-7.55 (m, 2H), 7.19-7.11 (m, 3H), 6.52 (s, 1H), 5.00 (s, 2H); MS: ESI (negative): 375, 377 (M−H).

EXAMPLE 12

[6-Chloro-3-(1,1-dioxo-2,3-dihydro-1H-1λ$^6$-benzo[d]isothiazol-3-yl)-indol-1-yl]-acetic Acid a.) 3-(6-Chloro-1H-indol-3-yl)-benzo[d]isothiazole 1,1-dioxide (Scheme 1)

The sub-title compound was prepared as described for example 1, step b) using 6-chloro indole.

b.) [6-Chloro-3-(1,1-dioxo-1H-1λ$^6$-benzo[d]isothiazol-3-yl)-indol-1-yl]-acetic Acid tert-butyl Ester The sub-title compound was prepared as described for example 1, step c) using the product from step a).

c.) [6-Chloro-3-(1,1-dioxo-2,3-dihydro-1H-1λ$^6$-benzo[d]isothiazol-3-yl)-2-methyl-indol-1-yl]-acetic Acid tert-butyl Ester The sub-title compound was prepared as described for example 1, step d) using the product from step b).

d.) [6-Chloro-3-(1,1-dioxo-2,3-dihydro-1H-1λ$^6$-benzo[d]isothiazol-3-yl)-indol-1-yl]-acetic Acid The title compound was prepared as described for example 5, step d) using the product from step c). $^1$H NMR (DMSO-d$_6$) δ 13.01 (bs, 1H), 8.46 (d, J=3.6 Hz, 1H), 7.90-7.87 (m, 1H), 7.63-7.58 (m, 2H), 7.64 (d, J=1.8 Hz, 1H), 7.45 (s, 1H), 7.26 (d, 1H, J=8.7 Hz), 7.23-7.29 (m, 1H), 6.97 (dt, J=1.5, 8.4 Hz, 1H), 6.09 (d, J=3.0 Hz, 1H), 5.04 (s, 2H); MS: ESI (negative): 375, 377 (M−H).

EXAMPLE 13

[3-(6-Fluoro-1,1-dioxo-2,3-dihydro-1H-1λ$^6$-benzo[d]isothiazol-3-yl)-2-methyl-indol-1-yl]-acetic Acid a.) 5-Fluorosaccharin (Scheme 1)

5-Fluoro-2-methyl-benzenesulfonyl chloride (1 g, 4.7 mmol) in 5 mL THF was added dropwise to a solution of ammonium hydroxide (1.6 mL, 15 mmol) in 10 mL THF. After stirring 1 h, the reaction was concentrated to dryness. The resulting solid was dissolved in 10 mL of 1 M NaOH and treated with KMnO$_4$ (2.4 g). The solution was heated to 50° C. overnight. The resulting solution was filtered through celite and acidified to pH ~1 with 10% HCl. After standing for several minutes, a precipitate formed. The precipitate was filtered, washed with water, and dried to give 0.29 grams of the sub-title compound as a white solid.

b.) 3-Chloro-6-fluoro-benzo[d]isothiazole 1,1-dioxide

The product from step a) (0.29 g) was treated with 4 mL dioxane, 1.5 mL thionyl chloride, and 40 μL DMF. The resulting solution was heated overnight at reflux and subsequently concentrated to dryness. The crude intermediate was used without further purification.

c.) 6-Fluoro-3-(2-methyl-1H-indol-3-yl)-benzo[d]isothiazole 1,1-dioxide

The sub-title compound was prepared as described for example 1, step b) using 2-methyl indole and the product from step b). The product did not crystallize upon quenching, and was instead purified by partitioning between DCM and water.

d.) [3-(6-Fluoro-1,1-dioxo-1H-1λ$^6$-benzo[d]isothiazol-3-yl)-2-methyl-indol-1-yl]-acetic Acid tert-butyl Ester The sub-title compound was prepared as described for example 1, step c) using the product from step c).

e.) [3-(6-Fluoro-1,1-dioxo-2,3-dihydro-1H-1λ$^6$-benzo[d]isothiazol-3-yl)-2-methyl-indol-1-yl]-acetic Acid tert-butyl Ester The sub-title compound was prepared as described for example 1, step d) using the product from step d).

f.) [3-(6-Fluoro-1,1-dioxo-2,3-dihydro-1H-1λ$^6$-benzo[d]isothiazol-3-yl)-2-methyl-indol-1-yl]-acetic Acid The title compound was prepared as described for example 1, step e) using the product from step e). MS: ESI (negative): 373 (M−H).

EXAMPLE 14

[3-(2-Methyl-1,1-dioxo-2,3-dihydro-1H-1λ$^6$-benzo[d]isothiazol-3-yl)-indol-1-yl]-acetic Acid (Scheme 1)

The intermediate from example 1, step d (33 mg, 0.08 mmol) was dissolved in DMF (1 mL) and treated with K$_2$CO$_3$ (28 mg, 0.2=mmol) followed by methyl iodide. The reaction was heated to 70°-80° C. for 1 h. The reaction mixture was cooled and partitioned between EtOAc and water. The organic layer was washed several times with water then concentrated to dryness. The crude residue was then treated with TFA (2 mL) for 2 h. The reaction was concentrated and purified by preparative LCMS to give the title compound. $^1$H NMR (DMSO-d6) δ 8.22-8.20 (m, 1H), 7.88-7.85 (m, 2H), 7.81 (s, 1H), 7.54 (d, J=8.1 Hz, 1H), 7.40-7.35 (m, 1H), 7.28 (t, J=7.5 Hz, 1H), 7.17 (d, J=7.8 Hz, 1H), 7.05 (t, J=7.2 Hz, 1H), 5.94 (s, 1H), 4.80 (s, 2H), 2.88 (s, 3H); MS: ESI (negative): 355 (M−H).

EXAMPLE 15

[3-(3-Benzyl-4-oxo-3,4-dihydro-phthalazin-1-yl)-indol-1-yl]-acetic Acid a.) 1-Chloro-4-(1H-indol-3-yl)-phthalazine (Scheme 3)

The sub-title compound was prepared in one step as described by Pal et al., *J. Org. Chem.* 68:6806 (2003).

b.) [3-(4-Chloro-phthalazin-1-yl)-indol-1-yl]-acetic Acid tert-butyl Ester

The product of step a) (280 mg, 1 mmol) was dissolved in 10 mL DMF and treated with 1.6 mmol t-butyl bromoacetate followed by $K_2CO_3$ (1.4 mmol). The reaction was stirred overnight at rt then partitioned between EtOAc and water. The organic layer was washed 3 times with water, dried over $MgSO_4$ and concentrated to give the sub-title compound as a while solid. MS: ESI (positive): 394 (M+H).

c.) [3-(4-Oxo-3,4-dihydro-phthalazin-1-yl)-indol-1-yl]-acetic Acid

The product of step b) (50 mg, 0.13 mmol) was dissolved in 4 mL THF. NaOH (0.52 mL of 1 M aq) was added and the reaction was heated to 60° C. for 3 days. The reaction was cooled, acidified with 1 M HCl, and extracted into DCM. Concentration gave the sub-title product as a yellow oil. MS: ESI (negative): 318 (M–H).

d.) [3-(3-Benzyl-4-oxo-3,4-dihydro-phthalazin-1-yl)-indol-1-yl]-acetic Acid

The product of step c) was dissolved in DMF (4 mL) and treated with $K_2CO_3$ (55 mg, 0.4 mmol) and benzyl bromide (0.25 mmol). The reaction was heated to 70° C. for 12 h. Additional $K_2CO_3$ (0.2 mmol) and benzyl bromide (0.25 mmol) was added and heating was continued for 3 h. The reaction was cooled and partitioned between EtOAc and water. The organic layer was washed 3 times with water and concentrated. The residue was dissolved in EtOH (2 mL) and treated with NaOH (0.5 mL, 1 M). After heating to 70° C. for 1 h, the reaction was cooled, acidified with HCl, and extracted into DCM. The organic layer was concentrated, dissolved in DMF, and purified by preparative LCMS. $^1$H NMR (DMSO-$d_6$) δ 8.41 (d, J=6.9 Hz, 1H), 8.16 (d, J=7.2 Hz, 1H), 7.98-7.89 (m, 2H), 7.87 (s, 1H), 7.61 (d, J=8.1 Hz, 1H), 7.44-7.27 (m, 6H), 7.17 (t, J=7.3 Hz, 1H), 7.03 (t, J=7.5 Hz, 1H), 5.43 (s, 2H), 4.80 (s, 2H); MS: ESI (negative): 408 (M–H).

EXAMPLE 16

[3-(3-Benzyl-4-oxo-3,4-dihydro-phthalazin-1-yl)-5-chloro-2-methyl-indol-1-yl]-acetic Acid a.) 1-Chloro-4-(5-chloro-2-methyl-1H-indol-3-yl)-phthalazine (Scheme 3)

5-Chloro-2-methylindole (0.74 g, 2.26 mmol) and 1,4-dichloro-phthalazine (0.45 g, 2.26 mmol) were treated with 30 mL of 1,2-dichloroethane and 3.2=mmol of $AlCl_3$ (427 mg). The resulting suspension was heated to 65° C. overnight. The reaction was cooled and quenched with 3 mL water. The resultant precipitate was filtered and dried under vacuum to give 0.65 g of the sub-title compound. MS: ESI (negative): 326, 328 (M–H).

b.) [5-Chloro-3-(4-chloro-phthalazin-1-yl)-2-methyl-indol-1-yl]-acetic Acid tert-butyl Ester The sub-title compound was prepared from the product of step a) using the procedure described in example 15, step b). MS: ESI (positive): 442, 444 (M+H).

c.) [5-Chloro-2-methyl-3-(4-oxo-3,4-dihydro-phthalazin-1-yl)-indol-1-yl]-acetic Acid tert-butyl Ester The product of step b) (300 mg) was treated with 10 mL HOAc and 2 mL of 1 M NaOH. The suspension was heated to 70° C. for 4 h. The reaction was cooled and partitioned between EtOAc and water. The organic layer was dried over $MgSO_4$ and concentrated to give 300 mg of the sub-title compound as a yellow oil. MS: ESI (negative): 422, 424 (M–H).

d.) [3-(3-Benzyl-4-oxo-3,4-dihydro-phthalazin-1-yl)-5-chloro-2-methyl-indol-1-yl]-acetic Acid The sub-title compound was prepared from the product of step c) and benzyl bromide using the procedure described in example 14. $^1$H NMR (DMSO-$d_6$) δ 13.20 (bs, 1H), 8.37-8.34 (m, 1H), 7.88-7.80 (m, 2H), 7.52 (d, J=9.3 Hz, 1H), 7.46 (d, J=7.2 Hz, 1H), 7.36-7.09 (m, 7H), 5.39 (d, J=15 Hz, 1H), 5.35 (d, J=15 Hz, 1H), 5.08 (s, 2H), 2.18 (s, 3H); MS: ESI (negative): 456,458 (M–H).

EXAMPLE 17

[3-(2-Benzyl-1,1-dioxo-1,2-dihydro-1λ6-benzo[e][1,2,3]thiadiazin-4-yl)-indol-1-yl]-acetic Acid a.) 1,1-Dioxo-2,3-dihydro-1H-1λ$^6$-benzo[e][1,2,3]thiadiazin-4-one (Scheme 2)

2-Chlorosulfonyl-benzoic acid methyl ester (7.04 g, 30 mmol) was added to hydrazine hydrate (66 mmol) stirring rapidly in 300 mL ether. The reaction was stirred overnight in an open flask and allowed to slowly concentrate. The remaining solvent was concentrated and the residue was treated with HOAc (3 mL) and DCM. The solution was washed with water, dried over $MgSO_4$, and concentrated to give 3 g of a white solid.

b.) 4-Chloro-2H-benzo[e][1,2,3]thiadiazine 1,1-dioxide

The product of step a) (300 mg) was treated with 5 mL $POCl_3$ and 2 drops DMF and heated to 100° C. overnight. The reaction was quenched over ice and immediately extracted into DCM. After drying over $MgSO_4$ and concentrating, the sub-title compound was isolated as an orange oil (240 mg). MS: ESI (negative): 215, 217 (M–H).

c.) 4-(1H-Indol-3-yl)-2H-benzo[e][1,2,3]thiadiazine 1,1-dioxide

The product of step b) (0.55 g, 2.5 mmol) was heated with indole (0.29 g, 2.5 mmol) and $AlCl_3$ (0.47 g, 3.5 mmol) in 25 mL 1,2-dichloroethane to 70° C. for 2 days. The reaction was quenched over ice and partitioned between water and DCM/EtOH. The organic layer concentrated and the sub-title compound was purified by chromatography (EtOAc/Hex) to give 435 mg of a foam. MS: ESI (negative): 296 (M–H).

d.) [3-(2-Benzyl-1,1-dioxo-1,2-dihydro-1$\lambda^6$-benzo[e][1,2,3]thiadiazin-4-yl)-indol-1-yl]-acetic Acid The product of step c) (93 mg, 0.3 mmol) was dissolved in 3 mL DMF and treated with $K_2CO_3$ (50 mg, 0.36 mmol) and benzyl bromide (57 mg, 0.33 mmol). After stirring at 75° C. overnight, t-butyl bromoacetate (0.36 mmol, 70 mg) and was added along with an additional quantity of $K_2CO_3$ (0.39 mmol, 54 mg). The reaction was heated for an additional 2 hours. The crude reaction was partitioned between EtOAc and water. The organic layer was concentrated to dryness and treated with TFA (3 mL). After 1 h, the reaction was concentrated and purified by preparative LCMS to give the title compound. $^1$H NMR (DMSO-$d_6$) δ 8.15 (d, 1H, J=3.6 Hz), 8.07-7.94 (m, 3H), 7.92 (s, 1H), 7.59 (d, J=7.5 Hz, 1H), 7.51-7.31 (m, 6H), 7.22 (t, J=7.2 Hz, 1H), 7.04 (t, J=7.8 Hz, 1H), 5.12 (s, 2H), 5.07 (s, 2H); MS: ESI (negative): 444 (M–H).

EXAMPLE 18

[3-(2-Methyl-1,1-dioxo-1,2-dihydro-1λ6-benzo[e][1,2,3]thiadiazin-4-yl)-indol-1-yl]-acetic Acid (Scheme 2)

The product of Example 17, step c) was alkylated with methyl iodide and t-butyl bromoacetate following the procedure described in example 17, step d). $^1$H NMR (DMSO-$d_6$) δ 8.11-7.90 (m, 5H), 7.85 (s, 1H), 7.44 (d, J=8.1 Hz, 1H), 7.22 (dt, J=0.9, 7.5 Hz, 1H), 7.15 (dt, J=1.2, 7.5 Hz, 1H), 4.72 (s, 2H), 3.51 (s, 3H); MS: ESI (negative): 368 (M–H).

EXAMPLE 19

[3-(1,1-Dioxo-2-phenethyl-1,2-dihydro-1$\lambda^6$-benzo[e][1,2,3]thiadiazin-4-yl)-2-methyl-indol-1-yl]-acetic Acid a.) 4-(2-Methyl-1H-indol-3-yl)-2H-benzo[e][1,2,3]thiadiazine 1,1-dioxide (Scheme 2)

The product of Example 17, step b) (1.5 g, 7 mmol) was heated with 2-methylindole (0.92 g, 7 mmol) and $AlCl_3$ (1.12 g, 8.4 mmol) in 70 mL 1,2-dichloroethane to 70° C. for 3 days. The reaction was quenched with water (2 mL) and cooled. The resulting precipitate was filtered and subsequently purified by chromatography (EtOAc/Hex) to give 200 mg of the sub-title compound. MS: ESI (negative): 296 (M–H).

b.) [3-(1,1-Dioxo-2-phenethyl-1,2-dihydro-1$\lambda^6$-benzo[e][1,2,3]thiadiazin-4-yl)-2-methyl-indol-1-yl]-acetic Acid The product of step a) was alkylated with 2-bromoethylbenzene and t-butyl bromoacetate following the procedure described in example 17, step d). $^1$H NMR (DMSO-$d_6$) δ 8.05 (d, J=6.9 Hz, 1H), 7.89 (t, J=7.6 Hz, 1H), 7.80 (t, J=7.8 Hz, 1H), 7.45-7.40 (m, 2H), 7.27-7.16 (m, 6H), 4.67 (s, 2H), 4.13 (t, J=7.2 Hz, 2H), 3.14 (t, J=7.2 Hz, 2H), 2.26 (s, 3H); MS: ESI (negative): 472 (M–H).

EXAMPLE 20

[3-(2-Methyl-3-oxo-2,3-dihydro-1H-isoindol-1-yl)-indol-1-yl]-acetic Acid a.) 3-Hydroxy-2-methyl-2,3-dihydro-isoindol-1-one (Scheme 4)

$NaBH_4$ (566 mg, 14.91 mmol) was added to a stirring solution of 2-methyl-isoindole-1,3-dione (2.0 g, 12.42 mmol) in methanol (20 mL) at 0° C. Stirring at 0° C. was maintained for 1 hour, then the reaction was warmed to room temperature. Additional $NaBH_4$ (566 mg, 14.91 mmol) was added in order to push the reaction to completion. The reaction was then quenched with acetic acid (5 mL) and partitioned between water and dichloromethane. The organic layer was washed several times with water and concentrated under vacuum to give 659-mg of the sub-title compound as a white solid. MS: ESI (positive): 164 (M+H).

b.) 3-(1H-Indol-3-yl)-2-methyl-2,3-dihydro-isoindol-1-one (Rees et al., *J. Chem. Soc.* 687 (1965))

The product from example 20, step a) (650 mg, 3.98 mmol) and indole (780 mg, 6.67 mmol) were heated (neat) to 180° C. for 30 minutes. The reaction was cooled to rt and the product was recrystallized from ethanol/water to give 452 mg of the sub-title compound as a tan solid.

c.) [3-(2-Methyl-3-oxo-2,3-dihydro-1H-isoindol-1-yl)-indol-1-yl]-acetic Acid

The product from example 20, step b) (450 mg, 1.72 mmol) was dissolved in DMF and treated with $K_2CO_3$ (284 mg, 2.06 mmol) followed by t-butyl bromoacetate (255 μL, 1.72 mmol). The reaction was heated to 100° C. for 5 h. The reaction was cooled, diluted with EtOAc, washed 3 times with water, and concentrated. The crude product was treated with TFA (neat) at room temperature for 45 minutes. The reaction was then concentrated to dryness and purified by preparative LCMS to give the title compound. $^1$H NMR ($CD_3OD$) δ 7.74-7.78 (m, 1H), 7.43 (t, J=3.7 Hz, 1H), 7.41 (t, J=3.6 Hz, 1H), 7.36 (s, 1H), 7.28-7.31 (m, 1H), 7.20 (d, J=8.1 Hz, 1H), 6.96 (t, J=7.2 Hz, 1H), 6.67 (t, J=7.2 Hz, 1H), 6.48 (d, J=7.8 Hz, 1H), 4.62 (s, 2H), 2.78 (s, 3H); MS: ESI (negative): 319 (M–H).

EXAMPLE 21

[3-(1-Benzyl-6-oxo-1,6-dihydro-pyridazin-3-yl)-5-chloro-2-methyl-indol-1-yl]-acetic Acid a.) 5-Chloro-3-(6-chloro-pyridazin-3-yl)-2-methyl-1H-indole (Scheme 3)

The sub-title compound was prepared using 1,4-dichloro-pyridazine as described for example 16, step a). MS: ESI (negative): 276, 278 (M–H).

b.) [5-Chloro-3-(6-chloro-pyridazin-3-yl)-2-methyl-indol-1-yl]-acetic Acid tert-butyl Ester The sub-title compound was prepared from the product of step a) using the procedure described in example 15, step b). MS: ESI (positive): 392, 394 (M+H).

c.) [5-Chloro-3-(6-hydroxy-pyridazin-3-yl)-2-methyl-indol-1-yl]-acetic Acid tert-butyl Ester The sub-title compound was prepared from the product of step b) using the procedure described in example 16, step c). The reaction was heated overnight. MS: ESI (negative): 372, 374 (M−H).

d.) [3-(1-Benzyl-6-oxo-1,6-dihydro-pyridazin-3-yl)-5-chloro-2-methyl-indol-1-yl]-acetic Acid The title compound was prepared from the product of step c) using the procedure described in example 14, step d). $^1$H NMR (DMSO-d$_6$) δ 7.75 (d, J=9.6 Hz, 1H), 7.61 (d, J=2.1 Hz, 1H), 7.51 (d, J=8.7 Hz, 1H), 7.39 (s, 1H), 7.38 (d, J=1.8 Hz, 1H), 7.35-7.30 (m, 1H), 7.15 (dd, J=8.1, 2.1 Hz, 1H), 7.07 (d, J=9.6 Hz, 1H), 5.35 (s, 2H), 5.07 (s, 2H), 2.41 (s, 3H); MS: ESI (negative): 406, 408 (M−H).

EXAMPLE 22

{3-[2-(3,5-Dimethyl-isoxazol-4-ylmethyl)-3-oxo-2,3-dihydro-1H-isoindol-1-yl]-indol-1-yl}-acetic Acid a.) 2-(3,5-Dimethyl-isoxazol-4-ylmethyl)-isoindole-1,3-dione (Scheme 4)

4-Chloromethyl-3,5-dimethyl-isoxazole (500 μL, 3.40 mmol) was added to a mixture of phthalimide (500 mg, 3.40 mmol) and K$_2$CO$_3$ (500 mg, 3.62 mmol) in DMF (5 mL) and stirred at ambient temperature overnight. The reaction was then heated to 70° C. for 5 hours and subsequently cooled and partitioned between ethyl acetate and water. The organic layer was washed several times with water and concentrated to give 1.0 g of the sub-title compound as a white solid. MS: ESI (positive): 257 (M+H).

b.) 2-(3,5-Dimethyl-isoxazol-4-ylmethyl)-3-hydroxy-2,3-dihydro-isoindol-1-one

NaBH$_4$ (36 mg, 0.938 mmol) was added slowly to a stirring mixture of 2-(3,5-Dimethyl-isoxazol-4-ylmethyl)-isoindole-1,3-dione (20 mg, 0.781 mmol) in methanol (2 mL). After stirring at room temperature for 10 minutes, the reaction was quenched with acetic acid (1 mL) and partitioned between water and dichloromethane. The organic layer was washed several times with water and concentrated under vacuum to give the sub-title compound as a white solid. MS: ESI (positive): 259 (M+H).

c.) 2-(3,5-Dimethyl-isoxazol-4-ylmethyl)-3-(1H-indol-3-yl)-2,3-dihydro-isoindol-1-one The product of step b) was treated according to the conditions described in example 22, step b). The product was purified by chromatography (EtOAc/Hex) to give the sub-title compound as a brown oil. MS: ESI (positive): 358 (M+H).

d.) {3-[2-(3,5-Dimethyl-isoxazol-4-ylmethyl)-3-oxo-2,3-dihydro-1H-isoindol-1-yl]-indol-1-yl}-acetic Acid The title compound was prepared from the product of step c) as described for example 22, step c). MS: ESI (negative): 414 (M−H).

EXAMPLE 23

{2-Methyl-3-[2-(3-methyl-butyl)-1,1-dioxo-1,2-dihydro-1λ$^6$-benzo[e][1,2,3]thiadiazin-4-yl]-indol-1-yl}-acetic Acid (Scheme 2)

The title compound was prepared from the product of example 19, step a) and 1-bromo-3-methyl-butane using the procedure described in example 17, step d). $^1$H NMR (DMSO-d$_6$) δ 8.09 (d, J=7.2 Hz, 1H), 7.90 (t, J=7.5 Hz, 1H), 7.81 (t, J=7.8 Hz, 1H), 7.44 (d, J=7.8 Hz, 1H), 7.38 (d, J=8.1 Hz, 1H), 7.19 (d, J=7.8 Hz, 1H), 7.09 (t, J=7.8 Hz, 1H), 4.52 (s, 2H), 3.89 (t, J=6.9 Hz, 2H), 1.90 (s, 3H), 1.74 (q, J=6.9 Hz, 2H), 1.64 (sept., J=6.7 Hz, 1H), 0.92 (d, J=6.3 Hz, 6H); MS: ESI (negative): 438 (M−H).

EXAMPLE 24

{5-Chloro-3-[3-(4-fluoro-benzyl)-4-oxo-3,4-dihydro-phthalazin-1-yl]-2-methyl-indol-1-yl}-acetic Acid (Scheme 3)

The title compound was prepared from the product of example 16, step c) and 4-fluorobenzyl bromide using the procedure described in example 14. $^1$H NMR (DMSO-d$_6$) δ 13.25 (bs, 1H), 8.41 (d, J=6.6 Hz, 1H), 7.94-7.87 (m, 2H), 7.58 (d, J=8.7 Hz, 1H), 7.52 (d, J=9.0 Hz, 1H), 7.45 (dd, J=5.7, 8.4 Hz, 2H), 7.24-7.10 (m, 4H), 5.44 (d, J=14.4 Hz, 1H), 5.38 (d, J=14.4 Hz, 1H), 5.14 (s, 2H), 2.24 (s, 3H); MS: ESI (negative): 474, 476 (M−H).

EXAMPLE 25

(5-Chloro-3-{3-[2-(4-chloro-phenoxy)-ethyl]-4-oxo-3,4-dihydro-phthalazin-1-yl}-2-methyl-indol-1-yl)-acetic Acid (Scheme 3)

The title compound was prepared from the product of example 16, step c) and 1-(2-bromo-ethoxy)-4-chloro-benzene using the procedure described in example 14. MS: ESI (negative): 520, 522 (M−H).

EXAMPLE 26

[3-(3-Benzothiazol-2-ylmethyl-4-oxo-3,4-dihydro-phthalazin-1-yl)-5-chloro-2-methyl-indol-1-yl]-acetic Acid (Scheme 3)

The title compound was prepared from the product of example 16, step c) and 2-chloromethyl-benzothiazole using the procedure described in example 14. $^1$H NMR (DMSO-d$_6$) δ 8.44-8.41 (m, 1H), 8.08 (d, J=8.1 Hz, 1H), 7.99 (d, J=8.1 Hz, 1H), 7.96-7.92 (m, 2H), 7.50 (t, J=7.5 Hz, 1H), 7.44 (t, J=7.5 Hz, 1H), 7.24 (d, J=1.8 Hz, 1H), 7.15 (dd, J=8.7, 2.1 Hz, 1H), 5.86 (s, 2H), 5.12 (s, 2H), 2.28 (s, 3H); MS: ESI (negative): 513, 515 (M–H).

EXAMPLE 27

{5-Chloro-3-[3-(2,3-dihydro-benzo[1,4]dioxin-2-ylmethyl)-4-oxo-3,4-dihydro-phthalazin-1-yl]-2-methyl-indol-1-yl}-acetic Acid (Scheme 3)

The title compound was prepared from the product of example 16, step c) and 2-chloromethyl-2,3-dihydro-benzo[1,4]dioxine using the procedure described in example 14. MS: ESI (negative): 514, 516 (M–H).

EXAMPLE 28

[3-(2-Benzyl-1,1-dioxo-2,3-dihydro-1H-1$\lambda^6$-benzo[d]isothiazol-3-yl)-indol-1-yl]-acetic Acid (Scheme 1)

The title compound was prepared by the method described for example 14 using benzyl bromide. $^1$H NMR (DMSO-d$_6$) δ 7.99 (d, J=8.7 Hz, 1H), 7.66-7.57 (m, 2H), 7.43 (s, 1H), 7.31-7.22 (m, 5H), 7.17 (d, J=7.5 Hz, 1H), 7.04 (t, J=7.6 Hz, 1H), 6.95 (d, J=7.8 Hz, 1H), 6.80 (t, J=7.5H, 1H), 5.76 (s, 1H), 4.53 (s, 2H), 4.55 (d, J=15.9 Hz, 1H), 3.93 (d, J=15.9 Hz, 1H); MS: ESI (negative): 431 (M–H).

EXAMPLE 29

{3-[2-(3-Methyl-butyl)-1,1-dioxo-2,3-dihydro-1H-1$\lambda^6$-benzo[d]isothiazol-3-yl]-indol-1-yl}-acetic Acid (Scheme 1)

The title compound was prepared by the method described for example 14 using isoamyl bromide. MS: ESI (negative): 411 (M–H).

EXAMPLE 30

[3-(1,1-Dioxo-2-quinolin-2-ylmethyl-2,3-dihydro-1H-1$\lambda^6$-benzo[d]isothiazol-3-yl)-indol-1-yl]-acetic Acid (Scheme 1)

The title compound was prepared by the method described for example 14 using 2-bromomethyl-quinoline. MS: ESI (negative): 482 (M–H).

EXAMPLE 31

(3-{2-[3-(4-Fluoro-phenoxy)-benzyl]-1,1-dioxo-2,3-dihydro-1H-1$\lambda^6$benzo[d]isothiazol-3-yl}-indol-1-yl)-acetic Acid (Scheme 1)

The title compound was prepared by the method described for example 14 using 3-(4-fluorophenoxy)benzyl bromide. MS: ESI (negative): 541 M–H).

EXAMPLE 32

[3-(2-Biphenyl-2-ylmethyl-1,1-dioxo-2,3-dihydro-1H-1$\lambda^6$-benzo[d]isothiazol-3-yl)-indol-1-yl]-acetic Acid (Scheme 1)

The title compound was prepared by the method described for example 14 using o-phenylbenzyl bromide. MS: ESI (negative): 507 (M–H).

EXAMPLE 33

{3-[1,1-Dioxo-2-(2-thiophen-2-yl-thiazol-4-ylmethyl)-2,3-dihydro-1H-1$\lambda^6$-benzo[d]isothiazol-3-yl]-indol-1-yl}-acetic Acid (Scheme 1)

The title compound was prepared by the method described for example 14 using 4-chloromethyl-2-thiophen-2-yl-thiazole. MS: ESI (negative): 520 (M–H).

EXAMPLE 34

(3-{2-[2-(4-Chloro-phenyl)-thiazol-4-ylmethyl]-1,1-dioxo-2,3-dihydro-1H-1$\lambda^6$-benzo[d]isothiazol-3-yl}-indol-1-yl)-acetic Acid (Scheme 1)

The title compound was prepared by the method described for example 14 using 4-chloromethyl-2-(4-chloro-phenyl)-thiazole. $^1$H NMR (DMSO-d$_6$) 13.05 (bs, 1H), 8.01 (d, J=8.7 Hz, 1H), 7.87 (d, J=8.4 Hz, 2H), 7.67-7.61 (m, 2H), 7.60 (s, 1H), 7.54 (s, 1H), 7.50 (d, J=8.1 Hz, 2H), 7.37 (d, J=8.4 Hz, 1H), 7.21-7.18 (m, 1H), 7.08 (t, J=7.6 Hz, 1H), 7.02 (d, J=7.8 Hz, 1H), 6.86 (t, J=7.5 Hz, 1H), 6.19 (s, 1H), 5.01 (s, 2H), 4.62 (d, J=16.5 Hz, 1H), 4.21 (d, J=16.5 Hz, 1H); MS: ESI (negative): 548, 550 (M–H).

EXAMPLE 35

{3-[2-(3,5-Dimethyl-isoxazol-4-ylmethyl)-1,1-dioxo-2,3-dihydro-1H-1$\lambda^6$benzo[d]isothiazol-3-yl]-indol-1-yl}-acetic Acid (Scheme 1)

The title compound was prepared by the method described for example 14 using 4-chloromethyl-3,5-dimethyl-isoxazole. MS: ESI (negative): 450 (M–H).

EXAMPLE 36

{2-Methyl-3-[2-(5-methyl-3-phenyl-isoxazol-4-ylmethyl)-1,1-dioxo-2,3-dihydro-1H-1$\lambda^6$-benzo[d]isothiazol-3-yl]-indol-1-yl}-acetic Acid (Scheme 1)

The title compound was prepared by the method described for example 14 using the product from example 3, step c) and 4-chloromethyl-5-methyl-3-phenyl-isoxazole. MS: ESI (negative): 526 (M–H).

EXAMPLE 37

(3-{2-[(4-Fluoro-phenylcarbamoyl)-methyl]-1,1-dioxo-2,3-dihydro-1H-1$\lambda^6$-benzo[d]isothiazol-3-yl}-2-methyl-indol-1-yl)-acetic Acid (Scheme 1)
The title compound was prepared by the method described for example 14 using the product from example 3, step c) and alpha-chloro-4-fluoroacetanilide. $^1$H NMR (DMSO-d$_6$) δ 8.06-8.03 (m, 1H), 7.70-7.62 (m, 2H), 7.51-7.46 (m, 2H), 7.39 (d, J=8.4 Hz, 1H), 7.17-7.13 (m, 2H), 7.02 (t, J=8.1 Hz, 1H), 6.80 (t, J=7.5 Hz, 1H), 6.72 (bs, 1H), 6.55 (s, 1H), 5.00 (s, 2H), 4.15 (d, J=17.4 Hz, 1H), 3.40 (d, J=17.4 Hz, 1H), 2.39 (s, 3H); MS: ESI (negative): 506 (M−H).

EXAMPLE 38

{3-[2-(2-Hydroxy-ethyl)-1,1-dioxo-2,3-dihydro-1H-1$\lambda^6$-benzo[d]isothiazol-3-yl]-2-methyl-indol-1-yl}-acetic Acid (Scheme 1)
The title compound was prepared by the method described for example 14 using the product from example 3, step c) and 2-bromoethanol. $^1$H NMR (DMSO-d$_6$) δ 7.98-7.95 (m, 1H), 7.62-7.58 (m, 3H), 7.36 (d, J=8.4 Hz, 1H), 7.04-7.01 (m, 2H), 6.80-6.78 (m, 1H), 6.14 (s, 1H), 5.00 (s, 2H), 4.75 (bs, 1H), 3.59-3.53 (m, 1H), 3.26-3.17 (m, 2H), 3.02-2.92 (m, 1H), 2.39 (s, 3H); MS: ESI (negative): 399 (M−H).

EXAMPLE 39

(3-{2-[2-(4-Chloro-phenoxy)-ethyl]-1,1-dioxo-2,3-dihydro-1H-1$\lambda^6$-benzo[d]isothiazol-3-yl}-2-methyl-indol-1-yl)-acetic Acid (Scheme 1)
The title compound was prepared by the method described for example 14 using the product from example 3, step c) and 1-(2-bromo-ethoxy)-4-chloro-benzene. MS: ESI (negative): 509 (M−H).

EXAMPLE 40

[3-(2-Ethoxycarbonylmethyl-1,1-dioxo-2,3-dihydro-1H-1$\lambda^6$benzo[d]isothiazol-3-yl)-2-methyl-indol-1-yl]-acetic Acid (Scheme 1)
The title compound was prepared by the method described for example 14 using the product from example 3, step c) and ethyl bromoacetate. MS: ESI (negative): 441 (M−H).

EXAMPLE 41

{3-[2-(2,3-Dihydro-benzo[1,4]dioxin-2-ylmethyl)-1,1-dioxo-2,3-dihydro-1H-1$\lambda^6$-benzo[d]isothiazol-3-yl]-2-methyl-indol-1-yl}-acetic Acid (Scheme 1)
The title compound was prepared by the method described for example 14 using the product from example 3, step c) and 2-bromomethyl-2,3-dihydro-benzo[1,4]dioxine. MS: ESI (negative): 503 (M−H).

EXAMPLE 42

{2-Methyl-3-[2-(2-methyl-thiazol-4-ylmethyl)-1,1-dioxo-2,3-dihydro-1H-1$\lambda^6$benzo[d]isothiazol-3-yl]-indol-1-yl}-acetic Acid (Scheme 1)
The title compound was prepared by the method described for example 14 using the product from example 3, step c) and 4-chloromethyl-2-methyl-thiazole. $^1$H NMR (DMSO-d$_6$) δ 13.04 (bs, 1H), 8.00 (d, J=8.7 Hz, 1H), 7.66-7.58 (m, 2H), 7.37 (d, J=8.1 Hz, 1H), 7.19 (s, 1H), 7.08 (d, J=6.3 Hz, 1H), 7.01 (t, J=7.8 Hz, 1H), 6.87-6.76 (m, 2H), 6.18 (s, 1H), 5.00 (s, 2H), 4.51 (d, J=16.2 Hz, 1H), 3.92 (d, J=16.2 Hz, 1H), 2.58 (s, 3H), 2.31 (s, 3H); MS: ESI (negative): 466 (M−H).

EXAMPLE 43

{3-[1,1-Dioxo-2-(3-trifluoromethyl-benzyl)-2,3-dihydro-1H-1$\lambda^6$-benzo[d]isothiazol-3-yl]-2-methyl-indol-1-yl}-acetic Acid (Scheme 1)
The title compound was prepared by the method described for example 14 using the product from example 3, step c) and 3-trifluoromethyl-benzyl bromide. MS: ESI (negative): 513 (M−H).

EXAMPLE 44

{2-Methyl-3-[2-(3-methyl-butyl)-1,1-dioxo-2,3-dihydro-1H-1$\lambda^6$-benzo[d]isothiazol-3-yl]-indol-1-yl}-acetic Acid (Scheme 1)
The title compound was prepared by the method described for example 14 using the product from example 3, step c) and 1-iodo-3-methyl-butane. MS: ESI (negative): 425 (M−H).

EXAMPLE 45

[3-(2-Allyl-1,1-dioxo-2,3-dihydro-1H-1$\lambda^6$-benzo[d]isothiazol-3-yl)-2-methyl-indol-1-yl]-acetic Acid (Scheme 1)
The title compound was prepared by the method described for example 14 using the product from example 3, step c) and allyl bromide. MS: ESI (negative): 395 (M−H).

EXAMPLE 46

{3-[1,1-Dioxo-2-(3-phenoxy-propyl)-2,3-dihydro-1H-1$\lambda^6$-benzo[d]isothiazol-3-yl]-2-methyl-indol-1-yl}-acetic Acid (Scheme 1)
The title compound was prepared by the method described for example 14 using the product from example 3, step c) and (3-bromo-propoxy)-benzene. MS: ESI (negative): 489 (M−H).

EXAMPLE 47

[3-(2-Isopropyl-1,1-dioxo-2,3-dihydro-1H-1λ$^6$-benzo[d]isothiazol-3-yl)-2-methyl-indol-1-yl]-acetic Acid (Scheme 1)
The title compound was prepared by the method described for example 14 using the product from example 3, step c) and 2-iodo propane. $^1$H NMR (DMSO-d$_6$) δ 7.91-7.88 (m, 1H), 7.63-7.53 (m, 2H), 7.35 (d, J=8.4 Hz, 1H), 7.17-6.78 (m, 4H), 6.14 (s, 1H), 4.98 (s, 2H), 3.68 (sept., J=6.8 Hz, 1H), 2.43 (s, 3H), 1.34 (d, J=6.9 Hz, 3H), 1.02 (d, J=6.9 Hz, 3H); MS: ESI (negative): 397 (M−H).

EXAMPLE 48

[3-(2-Benzothiazol-2-ylmethyl-1,1-dioxo-2,3-dihydro-1H-1λ$^6$-benzo[d]isothiazol-3-yl)-5-methyl-indol-1-yl]-acetic Acid (Scheme 1)
The title compound was prepared by the method described for example 14 using the product from example 2, step c) and 2-bromomethyl-benzothiazole. MS: ESI (negative): 502 (M−H).

EXAMPLE 49

{3-[2-(4-Fluoro-benzyl)-1,1-dioxo-2,3-dihydro-1H-1λ$^6$-benzo[d]isothiazol-3-yl]-5-methyl-indol-1-yl}-acetic Acid (Scheme 1)
The title compound was prepared by the method described for example 14 using the product from example 2, step c) and 4-fluorobenzyl bromide. $^1$H NMR (DMSO-d$_6$) 8.00 (d, J=6.6 Hz, 1H), 7.66-7.58 (m, 2H), 7.39 (s, 1H), 7.24 (dd, J=3.0, 8.4 Hz, 2H), 7.22-7.20 (m, 1H), 7.04 (t, J=8.8 Hz, 2H), 6.90 (d, J=8.1 Hz, 1H), 6.76 (s, 1H), 5.75 (s, 1H), 4.94 (s, 2H), 4.50 (d, J=15.9 Hz, 1H), 3.97 (d, J=15.9 Hz, 1H), 2.16 (s, 3H); MS: ESI (negative): 463 (M−H).

EXAMPLE 50

{3-[2-(3-Benzyloxy-propyl)-1,1-dioxo-2,3-dihydro-1H-1λ$^6$-benzo[d]isothiazol-3-yl]-5-methyl-indol-1-yl}-acetic Acid (Scheme 1)
The title compound was prepared by the method described for example 14 using the product from example 2, step c) and (3-bromo-propoxymethyl)-benzene. MS: ESI (negative): 503 (M−H).

EXAMPLE 51

{3-[1,1-Dioxo-2-(3-trifluoromethyl-benzyl)-2,3-dihydro-1H-1λ$^6$-benzo[d]isothiazol-3-yl]-5-methyl-indol-1-yl}-acetic Acid (Scheme 1)
The title compound was prepared by the method described for example 14 using the product from example 2, step c) and 3-trifluoromethyl benzyl bromide. MS: ESI (negative): 513 (M−H).

EXAMPLE 52

{3-[2-(3-Methoxy-propyl)-1,1-dioxo-2,3-dihydro-1H-1λ$^6$-benzo[d]isothiazol-3-yl]-5-methyl-indol-1-yl}-acetic Acid (Scheme 1)
The title compound was prepared by the method described for example 14 using the product from example 2, step c) and 3-bromo-1-methoxy propane. $^1$H NMR (DMSO-d$_6$) 7.95-7.92 (m, 1H), 7.60 (d, J=3.6 Hz, 1H), 7.58 (s, 1H), 7.28 (d, J=8.1 Hz, 1H), 7.12-7.09 (m, 1H), 7.02 (t, J=7.2 Hz, 1H), 6.97 (d, J=8.4 Hz, 1H), 6.79 (t, J=7.5 Hz, 1H), 5.89 (s, 1H), 4.57 (s, 2H), 3.44-3.03 (m, 4H), 3.01 (s, 3H), 2.45 (s, 3H), 1.71 (quint., J=6.6 Hz, 2H); MS: ESI (negative): 427 (M−H).

EXAMPLE 53

{3-[2-(Cyano-methyl-methyl)-1,1-dioxo-2,3-dihydro-1H-1λ$^6$-benzo[d]isothiazol-3-yl]-5-methyl-indol-1-yl}-acetic Acid (Scheme 1)
The title compound was prepared by the method described for example 14 using the product from example 2, step c) and 2-bromo-propionitrile. MS: ESI (negative): 408 (M−H).

EXAMPLE 54

{3-[2-(4-Fluoro-benzyl)-1,1-dioxo-2,3-dihydro-1H-1λ$^6$-benzo[d]isothiazol-3-yl]-5-methoxy-indol-1-yl}-acetic Acid (Scheme 1)
The title compound was prepared by the method described for example 14 using the product from example 4, step c) and 4-fluorobenzyl bromide. MS: ESI (negative): 479 (M−H).

EXAMPLE 55

[3-(1,1-Dioxo-2-phenethyl-2,3-dihydro-1H-1λ$^6$-benzo[d]isothiazol-3-yl)-5-methoxy-indol-1-yl]-acetic Acid (Scheme 1)
The title compound was prepared by the method described for example 14 using the product from example 4, step c) and 2-bromoethylbenzene. $^1$H NMR (DMSO-d$_6$) 13.03 (bs, 1H), 7.98 (d, J=8.7 Hz, 1H), 7.65-7.60 (m, 2H), 7.50 (s, 1H), 7.29 (d, J=9.0 Hz, 1H), 7.25-7.13 (m, 4H), 7.09 (d, J=8.1 Hz, 2H), 6.74 (dd, J=2.4, 9.0 Hz, 1H), 6.54 (d, J=2.4 Hz, 1H), 5.95 (s, 1H), 5.00 (s, 2H), 3.51 (s, 3H), 3.42 (ddd, J=6.3, 10.2, 15.9 Hz, 1H), 3.14 (ddd, J=5.7, 9.9, 15.0 Hz, 1H), 3.00-2.70 (m, 2H); MS: ESI (negative): 475 (M−H).

EXAMPLE 56

{5-Methoxy-3-[2-(1-methyl-2-phenyl-ethyl)-1,1-dioxo-2,3-dihydro-1H-1λ$^6$-benzo[d]isothiazol-3-yl]-indol-1-yl}-acetic Acid (Scheme 1)
The title compound was prepared by the method described for example 14 using the product from example 4, step c) and (2-bromo-propyl)-benzene. MS: ESI (negative): 489 (M−H).

EXAMPLE 57

{3-[2-(4-Cyano-benzyl)-1,1-dioxo-2,3-dihydro-1H-1$\lambda^6$-benzo[d]isothiazol-3-yl]-5-methoxy-indol-1-yl}-acetic Acid (Scheme 1)

The title compound was prepared by the method described for example 14 using the product from example 4, step c) and 4-cyanobenzyl bromide. MS: ESI (negative): 486 (M−H).

EXAMPLE 58

[3-(2-Allyl-1,1-dioxo-2,3-dihydro-1H-1$\lambda^6$-benzo[d]isothiazol-3-yl)-5-chloro-2-methyl-indol-1-yl]-acetic Acid (Scheme 1)

The title compound was prepared by the method described for example 14 using the product from example 6, step c) and allyl bromide. $^1$H NMR (DMSO-d$_6$) 13-14 (bs, 1H), 8.00 (d, J=8.7 Hz, 1H), 7.67-7.59 (m, 2H), 7.45 (d, J=8.7 Hz, 1H), 7.06 (d, J=6.3 Hz, 1H), 7.02 (dd, J=1.8, 8.7 Hz, 1H), 6.83 (s, 1H), 5.96 (s, 1H), 5.82-5.69 (m, 1H), 5.14 (d, J=7.5 Hz, 1H), 5.10 (s, 1H), 5.03 (s, 2H), 3.90 (dd, J=4.8, 15.9 Hz, 1H), 3.45-3.36 (m, 1H), 2.37 (s, 3H); MS: ESI (negative): 429, 431 (M−H).

EXAMPLE 59

[5-Chloro-3-(2-ethoxycarbonylmethyl-1,1-dioxo-2,3-dihydro-1H-1$\lambda^6$-benzo[d]isothiazol-3-yl)-2-methyl-indol-1-yl]-acetic Acid (Scheme 1)

The title compound was prepared by the method described for example 14 using the product from example 6, step c) and ethyl bromoacetate. $^1$H NMR (DMSO-d$_6$) 13.15 (bs, 1H), 8.07-8.03 (m, 1H), 7.70-7.63 (m, 2H), 7.44 (d, J=8.7 Hz, 1H), 7.12 (d, J=8.1 Hz, 1H), 7.02 (dd, J=1.8, 8.7 Hz, 1H), 6.72 (s, 1H), 6.28 (s, 1H), 5.03 (s, 2H), 4.05-3.92 (m, 2H), 3.41 (q, J=6.9 Hz, 2H), 1.05 (t, J=6.9 Hz, 3H); MS: ESI (negative): 475, 477 (M−H).

EXAMPLE 60

{5-Chloro-3-[2-(4-fluoro-benzyl)-1,1-dioxo-2,3-dihydro-1H-1$\lambda^6$-benzo[d]isothiazol-3-yl]-2-methyl-indol-1-yl}-acetic Acid (Scheme 1)

The title compound was prepared by the method described for example 14 using the product from example 6, step c) and 4-fluorobenzyl bromide. $^1$H NMR (DMSO-d$_6$) 13.2 (bs, 1H), 8.05 (d, J=8.1 Hz, 1H), 7.67 (t, J=7.2 Hz, 1H), 7.62 (dt, J=1.5, 75 Hz, 1H), 7.44 (d, J=8.7 Hz, 1H), 7.19-6.96 (m, 6H), 6.83 (s, 1H), 5.83 (s, 1H), 5.01 (d, J=18.3 Hz, 1H), 5.00 (d, J=18.3 Hz, 1H), 4.50 (d, J=15.6 Hz, 1H), 3.83 (d, J=15.6 Hz, 1H), 2.11 (s, 3H); MS: ESI (negative): 497, 499 (M−H).

EXAMPLE 61

{5-Chloro-2-methyl-3-[2-(5-methyl-3-phenyl-isoxazol-4-ylmethyl)-1,1-dioxo-2,3-dihydro-1H-1$\lambda^6$-benzo[d]isothiazol-3-yl]-indol-1-yl}-acetic Acid (Scheme 1)

The title compound was prepared by the method described for example 14 using the product from example 6, step c) and 4-chloromethyl-5-methyl-3-phenyl-isoxazole. $^1$H NMR (DMSO-d$_6$) 7.99-7.91 (m, 1H), 7.69-7.60 (m, 2H)), 7.43 (d, J=8.7 Hz, 1H), 7.36 (d, J=7.2 Hz, 2H), 7.23-6.75 (m, 6H), 5.94 (s, 1H), 4.96 (s, 2H), 4.33 (d, J=14.1 Hz, 1H), 4.07 (d, J=14.1 Hz, 1H), 3.30 (s, 3H), 2.41 (s, 3H); MS: ESI (negative): 560, 562 (M−H).

EXAMPLE 62

{3-[2-(3,5-Dimethyl-isoxazol-4-ylmethyl)-6-fluoro-1,1-dioxo-2,3-dihydro-1H-1$\lambda^6$-benzo[d]isothiazol-3-yl]-2-methyl-indol-1-yl}-acetic Acid (Scheme 1)

The title compound was prepared by the method described for example 14 using the product from example 13, step e) and chloromethyl-3,5-dimethyl-isoxazole. $^1$H NMR (DMSO-d$_6$) δ 13.1 (bs, 1H), 7-99 (dd, J=2.4, 7.5 Hz, 1H), 7.47 (dt, J=2.1, 8.8 Hz, 1H), 7.14-6.74 (m, 4H), 5.93 (s, 1H), 5.01 (s, 2H), 4.02 (d, J=15 Hz, 1H), 3.98 (d, 1H, J=15 Hz, 1H), 2.40 (s, 3H), 2.04 (s, 3H), 1.71 (s, 3H); MS: ESI (negative): 482 (M−H).

EXAMPLE 63

{3-[6-Fluoro-2-(3-fluoro-benzyl)-1,1-dioxo-2,3-dihydro-1H-1$\lambda^6$benzo[d]isothiazol-3-yl]-2-methyl-indol-1-yl}-acetic Acid (Scheme 1)

The title compound was prepared by the method described for example 14 using the product from example 13, step e) and 4-fluorobenzyl bromide. $^1$H NMR (DMSO-d$_6$) δ 13.2 (bs, 1H), 8.11 (dd, J=2.4, 7.5 Hz, 1H), 7.50 (dt, J=2.4, 8.8 Hz, 1H), 7.41 (d, J=8.4 Hz, 1H), 7.32-6.77 (m, 8H), 5.89 (s, 1H), 5.00 (d, J=18 Hz, 1H), 4.98 (d, J=18 Hz, 1H), 4.56 (d, J=15.9 Hz, 1H), 3.81 (d, J=15.9 Hz, 1H), 2.11 (s, 3H); MS: ESI (negative): 481 (M−H).

EXAMPLE 64

[3-(6-Fluoro-1,1-dioxo-2-phenethyl-2,3-dihydro-1H-1$\lambda^6$-benzo[d]isothiazol-3-yl)-2-methyl-indol-1-yl]-acetic Acid (Scheme 1) The title compound was prepared by the method described for example 14 using the product from example 13, step e) and 2-phenethyl bromide. MS: ESI (negative): 477 (M−H).

EXAMPLE 65

{3-[2-(3,5-Dimethyl-isoxazol-4-ylmethyl)-3-methyl-1,1-dioxo-2,3-dihydro-1H-1$\lambda^6$-benzo[d]isothiazol-3-yl]-2-methyl-indol-1-yl}-acetic Acid a.) [2-Methyl-3-(3-methyl-1,1-dioxo-2,3-dihydro-1H-1$\lambda^6$-benzo[d]isothiazol-3-yl)-indol-1-yl]-acetic Acid tert-butyl Ester (Scheme 5)

The product of example 3, step b) (1.0 g, 2.44 mmol) was dissolved in 40 mL toluene and cooled to 0° C. Me$_3$Al (1.83 mL of 2 M solution in toluene) was slowly added and the reaction was stirred for 45 minutes at 0° C. MeMgBr (3.5 mL of 1.4 M solution) was added and the reaction was allowed to warn to rt. The reaction was quenched with saturated NH$_4$Cl then partitioned between water and EtOAc. The organic layer was dried over MgSO$_4$ and the crude product was purified by silica gel chromatography (EtOAc/Hex) to give 450 mg of the sub-title compound.

b.) {3-[2-(3,5-Dimethyl-isoxazol-4-ylmethyl)-3-methyl-1,1-dioxo-2,3-dihydro-1H-1$\lambda^6$-benzo[d]isothiazol-3-yl]-2-methyl-indol-1-yl}-acetic Acid The product of step a) (50 mg, 0.12 mmol) was dissolved in 2 mL of DMF and treated with 0.24 mmol (35 mg) of 4-chloromethyl-3,5-dimethyl-isoxazole and 0.23 mmol (32 mg) of K$_2$CO$_3$. The reaction was heated to 80° C. for 1 h then diluted with EtOAc (5 mL) and was washed 3× with water. The organic layer was concentrated and subsequently treated with EtOH (5 mL) and 1M NaOH (1 mL). The reaction was heated to 75° C. for 2 h, cooled to rt, acidified with 1M HCl (3 mL) and extracted 3× into DCM. The combined extracts were concentrated and purified by preparative LCMS to give the title compound. $^1$H NMR (DMSO-d$_6$) δ 7.81 (dd, J=3.6, 5.7 Hz, 1H), 7.56 (dt, J=3.0, 8.7 Hz, 2H), 7.28 (d, J=8.1 Hz, 1H), 7.14-7.11 (m, 2H), 7.00 (t, J=7.2 Hz, 1H), 6.80 (t, J=7.2 Hz, 1H), 4.64 (s, 2H), 4.01 (d, J=14.7 Hz, 1H), 3.89 (d, J=14.7 Hz, 1H), 2.10 (s, 3H), 1.91 (s, 3H), 1.89 (s, 3H), 1.80 (s, 3H); MS: ESI (negative): 478.6 (M–H).

EXAMPLE 66

{3-[2-(3-Fluoro-benzyl)-3-methyl-1,1-dioxo-2,3-dihydro-1H-1$\lambda^6$-benzo[d]isothiazol-3-yl]-2-methyl-indol-1-yl}-acetic Acid (Scheme 5)

The product of example 65, step a) (50 mg, 0.12 mmol) was dissolved in 2 mL DMF and treated with K$_2$CO$_3$ (32 mg, 0.23 mmol) and 3-fluoro-benzylbromide (43 mg, 0.23 mmol). After heating to 75° C. for 2 h, the reaction was cooled, diluted with EtOAc, and washed 3× H$_2$O. The organic solution was concentrated and treated with 3 mL TFA for 2 h at rt. The reaction was concentrated and the title compound was isolated by preparative LCMS to give the title compound. MS: ESI (negative): 477.5 (M–H).

EXAMPLE 67

{2-Methyl-3-[3-methyl-1,1-dioxo-2-(2-phenoxy-ethyl)-2,3-dihydro-1H-1-benzo[d]isothiazol-3-yl]-indol-1-yl}-acetic Acid (Scheme 5)

The title compound was prepared by the method described in example 66 using (2-bromo-ethoxy)-benzene. MS: ESI (negative): 489.7 (M–H).

EXAMPLE 68

{3-[2-(3,5-Dimethyl-isoxazol-4-ylmethyl)-3-oxo-2,3-dihydro-1H-isoindol-1-yl]-2-methyl-indol-1-yl}-acetic Acid a.) 2-(3,5-Dimethyl-isoxazol-4-ylmethyl)-3-(2-methyl-1H-indol-3-yl)-2,3-dihydro-isoindol-1-one (Scheme 4)

The product of example 22, step b) (230 mg, 0.89 mmol) was treated with 2-methyl indole (196 mg, 1.5 mmol) and heated (neat) to 180° C. for 1 h. The reaction was cooled and the sub-title product was purified by silica chromatography (EtOAc/Hex).

b.) {3-[2-(3,5-Dimethyl-isoxazol-4-ylmethyl)-3-oxo-2,3-dihydro-1H-isoindol-1-yl]-2-methyl-indol-1-yl}-acetic Acid tert-butyl Ester The product from step a) (100 mg, 0.3=mmol) was dissolved in DMF (4 mL) and treated with t-butyl bromoacetate (112 mg, 0.6 mmol) and K$_2$CO$_3$ (103 mg, 0.75 mmol). After heating to 70° C. for 14 h, the reaction was diluted with DCM and washed repeatedly with water. Concentration gave 110 mg of the sub-title compound which was used without further purification.

c.) {3-[2-(3,5-Dimethyl-isoxazol-4-ylmethyl)-3-oxo-2,3-dihydro-1H-isoindol-1-yl]-2-methyl-indol-1-yl}-acetic Acid The crude product of step b) was dissolved in 3 mL EtOH and treated with 0.5 mL of 1 M NaOH. After heating to 70° C. for 1 h, the reaction was cooled, acidified with 1 M HCl and extracted into DCM. The extracts were concentrated and the title compound was purified by preparative LCMS to give the title compound. $^1$H NMR (DMSO-d$_6$) δ 7.84-7.81 (m, 1H), 7.56-7.46 (m, 2H), 7.25 (d, J=8.1 Hz, 1H), 7.19-7.16 (m, 1H), 6.93 (t, J=7.5 Hz, 1H), 6.69 (t, J=7.5 Hz, 1H), 6.39 (d, J=7.8 Hz, 1H), 3.73 (s, 1H), 4.85 (d, J=15.2 Hz, 1H), 4.52 (d, J=17.1 Hz, 1H), 4.51 (d, J=17.1 Hz, 1H), 3.51 (d, J=15.3 Hz, 1H), 2.35 (s, 3H), 2.07 (s, 3H), 2.02 (s, 3H); MS: ESI (negative): 428.6 (M–H).

EXAMPLE 69

{3-[2-(3,5-Dimethyl-isoxazol-4-ylmethyl)-1,1-dioxo-$\lambda^6$-isothiazolidin-3-yl]-2-methyl-indol-1-yl}-acetic Acid a.) (3-Formyl-2-methyl-indol-1-yl)-acetic Acid tert-butyl Ester (Scheme 6)

K$_2$CO$_3$ (15 mmol, 2.07 g) and 1-formyl-2-methyl indole (10 mmol, 1.59 g) were stirred in 50 mL DMF. t-Butyl bromoacetate (12mmol, 1.77 mL) was added and the reaction was heated to 80° C. for 1 h. The reaction was cooled, diluted with 100 mL EtOAc, and washed with water (3×50 mL). The organic solution was dried over MgSO$_4$ and concentrated to give the sub-title compound as a yellow solid (2.6 g).

b.) {2-Methyl-3-[(2-phenyl-ethenesulfonylimino)-methyl]-indol-1-yl}-acetic Acid tert-butyl Ester The product of step a) (1.5 g, 5.5 mmol), 2-phenyl-ethenesulfonic acid amide (1.0 g, 5.5 mmol), and PPTS (75 mg) were treated with 500 mL toluene and heated to reflux overnight in a flask equipped with a Dean-Stark trap. The hot reaction mixture was decanted and allowed to cool. The resulting precipitate was filtered and washed with toluene to give 1.86 g of the sub-title compound as a white solid.

c.) {2-Methyl-3-[1-(2-phenyl-ethenesulfonylamino)-allyl]-indol-1-yl}-acetic Acid tert-butyl Ester The product of step b) (2.2 g, 5 mmol) was treated with 100 mL toluene. The slurry was stirred at 0° C. and treated with Me$_3$Al (3.8 mL of 2 M in toluene) followed by vinyl magnesium bromide (10 mL of 1 M). The reaction was warmed to rt and stirred for 10 minutes. The reaction was cooled to 0° C., quenched with aqueous acetic acid, and partitioned between water and EtOAc (200 mL each). The organic layer was washed with 1 M NaOH, dried over MgSO$_4$ and purified over silica gel (30% EtOAc/Hex) to give 1.25 g of the sub-title compound as an oil.

d.) [3-(1,1-Dioxo-2,3-dihydro-1H-$\lambda^6$-isothiazol-3-yl)-2-methyl-indol-1-yl]-acetic Acid tert-butyl Ester The product of step c) (1.26 g, 2.7 mmol) was dissolved in 300 mL DCM under an Ar atmosphere. Grubbs catalyst (2$^{nd}$ generation, 154 mg, 0.19 mmol) was added and the solution was heated to reflux for 3 h. The reaction was concentrated and the sub-title compound was purified by silica gel chromatography (EtOAc/Hex) to give 0.80 g of the sub-title compound as a dark oil.

e.) [3-(1,1-Dioxo-$\lambda^6$-isothiazolidin-3-yl)-2-methyl-indol-1-yl]-acetic Acid tert-butyl Ester The product of step d) (65 mg, 0.18 mmol) was dissolved in 4 mL isopropanol and treated with NaBH$_4$ (7 mg, 0.18 mmol). The reaction was heated to 80° C. for 2 h, after which time an additional 7 mg of NaBH$_4$ was added. Heating was continued for 1 h. The reaction was quenched with HOAc and partitioned between DCM and water. The organic layer was washed with water and concentrated to give 58 mg of crude sub-title compound which was used without further purification.

f.) {3-[2-(3,5-Dimethyl-isoxazol-4-ylmethyl)-1,1-dioxo-$\lambda^6$-isothiazolidin-3-yl]-2-methyl-indol-1-yl}-acetic Acid The product of step e) (58 mg, 0.16 mmol) was dissolved in DMF (3 mL) and treated with K$_2$CO$_3$ (44 mg, 0.32 mmol) and 4-chloromethyl-3,5-dimethyl-isoxazole (0.32 mmol, 47 mg). After heating to 80° C. for 2 h, the reaction was diluted with EtOAc and washed 3× with water. The organic layer was concentrated and treated with EtOH (3 mL) and 1 M NaOH (0.7 mL). After heating to 80° C. for 1 h the reaction was concentrated to dryness and purified by preparative LCMS to give the title compound. $^1$H NMR (DMSO-d$_6$) δ 7.70 (d, J=7.2 Hz, 1H), 7.33 (d, J=8.1 Hz, 1H), 7.07 (t, J=7.5 Hz, 1H), 6.98 (t, J=7.3 Hz, 1H), 4.77 (s, 2H), 4.61 (dd, 1H, J=6.3, 10.2 Hz), 3.72 (s, 2H), 3.57 (dd, 1H, J=7.2, 12.3 Hz), 3.25-3.05 (m, 1H), 2.62-2.25 (m, 2H), 2.21 (s, 3H), 1.88 (s, 3H); MS: ESI (negative): 416.8 (M−H).

EXAMPLE 70

[3-(3-Butyl-4-oxo-3,4,4a,5,8,8a-hexahydro-phthalazin-1-yl)-2-methyl-indol-1-yl]-acetic Acid a.) 6-(2-Methyl-1H-indole-3-carbonyl)-cyclohex-3-enecarboxylic Acid (Scheme 7)

2-Methyl indole (50 mmol, 6.55 g) and AlCl$_3$ (50 mmol, 7.3 g) were stirred in 500 mL DCE. cis-1,2,3,6-Tetrahydrophthalic anhydride (50 mmol, 7.6 g) was added and the reaction was heated to 65° C. for 6 h. The reaction was carefully quenched with 10 mL water and stirred overnight. The resulting red solid was filtered, washed with water, and dried to give 15 g of the sub-title compound.

b.) 2-Butyl-4-(2-methyl-1H-indol-3-yl)-4a,5,8,8a-tetrahydro-2H-phthalazin-1-one

The product of step a) (200 mg, 0.71 mmol) was treated with Et$_3$N (0.71 mmol, 98 uL), n-butyl hydrazine oxalate (0.71 mmol, 126 mg) and 10 mL toluene. The suspension was refluxed for 48 h. The reaction was cooled, treated with 15 mL EtOAc and 5 mL 1M NaOH, and heated to 70° C. for 30 min. The organic layer was filtered through silica gel and further eluted with EtOAc. The combined eluent was concentrated to dryness to give the sub-titled compound which was used without further purification.

c.) [3-(3-Butyl-4-oxo-3,4,4a,5,8,8a-hexahydro-phthalazin-1-yl)-2-methyl-indol-1-yl]-acetic Acid The product of step b) was dissolved in DMF (4 mL) and treated with K$_2$CO$_3$ (0.7 mmol, 97 mg) and t-butyl bromoacetate (0.5 mmol, 74 uL). After heating at 75° C. for 2 h, the reaction was cooled, diluted with EtOAc (10 mL) and washed 3× water. The organic solution was concentrated to dryness and treated with 4 mL TFA for 1.5 h. The reaction was concentrated and the title compound was purified by preparative LCMS. $^1$H NMR (DMSO-d$_6$) δ 7.76 (d, J=8.1 Hz, 1H), 7.30 (d, J=7.5 Hz, 1H), 7.09-6.99 (m, 2H), 5.70 (d, J=10.8 Hz, 1H), 5.63 (d, J=10.8 Hz, 1H), 3.91 (dt, J=6.9, 13.2 Hz, 1H), 3.62 (dt, J=6.6, 13.2 Hz, 1H), 3.36 (quint., J=5.7 Hz, 1H), 2.96 (t, J=5.1 Hz, 1H), 2.79-2.71 (m, 1H), 2.35-1.94 (m, 4H), 1.64 (quint., J=7.1 Hz, 2H), 1.31 (sext., J=7.5 Hz, 1H), 0.91 (t, J=7.2 Hz, 3H); MS: ESI (negative): 392 (M−H).

EXAMPLE 71

[3-(3-Benzyl-4-oxo-3,4,4a,5,8,8a-hexahydro-phthalazin-1-yl)-2-methyl-indol-1-yl]-acetic Acid (Scheme 7)

The title compound was prepared by the method described for example 70 except using benzyl hydrazine hydrochloride in step b). $^1$H NMR (DMSO-d$_6$) δ 7.67 (d, J=7.8 Hz, 1H), 7.42 (d, J=8.1 Hz, 1H), 7.37-7.26 (m, 5H), 7.12 (t, J=7.5 Hz, 1H), 7.03 (t, J=7.5, 1H), 5.71 (d, J=12 Hz, 1H), 5.61 (d, J=12 Hz, 1H), 5.15 (d, J=14.7 Hz, 1H), 5.01 (s, 2H), 4.81 (d, J=14.7 Hz, 1H), 3.11 (t, J=5.6 Hz, 1H), 2.81-2.75 (m, 1H), 2.35 (s, 3H), 2.35-2.18 (m, 2H), 2.07-1.88 (m, 2H); MS: ESI (positive): 428.8 (M+H).

EXAMPLE 72

[2-Methyl-3-(4-oxo-3-phenethyl-3,4,4a,5,8,8a-hexahydro-phthalazin-1-yl)-indol-1-yl]-acetic Acid (Scheme 7)

The title compound was prepared by the method described for example 70 except using phenethyl hydrazine sulfuric acid salt in step b). $^1$H NMR (DMSO-$d_6$) δ 7.73 (d, J=6.9 Hz, 1H), 7.35-7.14 (m, 7H), 7.08 (t, J=6.4 Hz, 1H), 7.03 (t, J=6.4 Hz, 1H), 5.66 (d, J=11.1 Hz, 1H), 5.55 (d, J=11.1 Hz, 1H), 4.47 (s, 2H), 4.18 (dt, J=7.2, 13.2 Hz, 1H), 3.88 (dt, J=6.9, 13.5 Hz, 1H), 3.32 (quint., J=5.4 Hz, 1H), 2.99 (t, J=7.2 Hz, 1H), 2.93 (t, J=5.6 Hz, 1H), 2.76-2.66 (m, 1H), 2.45 (s, 3H), 2.24-1.97 (m, 4H); MS: ESI (negative): 440.8 M−H).

EXAMPLE 73

[3-(1-Benzyl-5,5-dimethyl-6-oxo-1,4,5,6-tetrahydro-pyridazin-3-yl)-5-chloro-2-methyl-indol-1-yl]-acetic Acid a.) 4-(5-Chloro-2-methyl-1H-indol-3-yl)-2,2-dimethyl-4-oxo-butyric Acid (Scheme 7)

3,3-Dimethyl-dihydro-furan-2,5-dione (7.8 mmol, 1.0 g), 5-chloro-2-methylindole (13.8 mmol, 2.28 g), and AlCl$_3$ (9.0 mmol, 1.2 g) were stirred in 100 mL DCE overnight at 65° C. The reaction was cooled and quenched with 10 mL water. The resultant precipitate was filtered and washed with a small amount of DCE giving 1.06 g of the sub-titled compound.

b.) 2-Benzyl-6-(5-chloro-2-methyl-1H-indol-3-yl)-4,4-dimethyl-4,5-dihydro-2H-pyridazin-3-one The product of step a) (0.5 mmol, 147 mg) was treated with toluene (10 mL), benzyl hydrazine dihydrochloride (0.7 mmol, 136 mg) and Et$_3$N (1.3 mmol, 181 uL). The reaction was refluxed overnight then cooled to rt. Filtration through a pad of silica gel followed by elution with EtOAc gave the sub-title compound.

c.) [3-(1-Benzyl-5,5-dimethyl-6-oxo-1,4,5,6-tetrahydro-pyridazin-3-yl)-5-chloro-2-methyl-indol-1-yl]-acetic Acid The product of step b) (~0.3 mmol) was dissolved in 5 mL DMF and treated with K$_2$CO$_3$ (1 mmol, 138 mg) and t-butyl bromoacetate (1 mmol, 195 mg). After heating to 80° C. for ½ h, the reaction was cooled, diluted with EtOAc and washed 5× water. The reaction was concentrated, dissolved in EtOH (5 mL) and treated with 1.4 mL of 1M NaOH. After heating to 80° C. for ½ h, the reaction was acidified with 3 M HCl and extracted into DCM (3×).

The title product was purified by preparative LCMS. $^1$H NMR (DMSO-$d_6$) δ 7.65 (d, J=2.4 Hz, 1H), 7.48-7.30 (m, 6H), 7.12 (dd, J=6.6, 2.4 Hz, 1H), 5.04 (s, 2H), 4.94 (s, 2H), 2.96 (s, 2H), 2.38 (s, 3H), 1.12 (s, 6H); MS: ESI (negative): 436 (M−H).

EXAMPLE 74

[3-(1,1-Dioxo-2-phenyl-2,3-dihydro-1H-1λ$^6$-benzo[d]isothiazol-3-yl)-2-methyl-indol-1-yl]-acetic Acid a.) [3-(1,1-Dioxo-2-phenyl-2,3-dihydro-1H-λ$^6$-benzo[d]isothiazol-3-yl)-2-methyl-indol-1-yl]-acetic Acid tert-butyl Ester (Scheme 1)

The product of example 3, step c) (150 mg, 0.36 mmol) was dissolved in toluene (8 mL) and treated with CuI (69 mg, 0.36 mmol), N,N'-dimethyl ethylenediamine (77 uL, 0.72 mmol), bromobenzene (85 mg, 0.54 mmol), and K$_2$CO$_3$ (149 mg, 1.1 mmol). The reaction was heated to reflux for 3 days. Upon cooling, the reaction was filtered and concentrated to give the crude product which was used without further purification.

b.) [3-(1,1-Dioxo-2-phenyl-2,3-dihydro-1H-1λ$^6$-benzo[d]isothiazol-3-yl)-2-methyl-indol-1-yl]-acetic Acid The crude product from step a) (73 mg, 0.15 mmol) was dissolved in 8 mL EtOH and treated with 1 mL of 1 M NaOH. After heating to 80° C. for 2 h, the reaction was acidified with aqueous HCl and extracted into DCM (2×5 mL). The title compound was purified by preparative LCMS. $^1$H NMR (DMSO-$d_6$) δ 8.09-8.06 (m, 1H), 7.72-7.65 (m, 2H), 7.46-7.26 (m, 5H), 7.17 (t, J=7.3 Hz, 1H), 7.13-7.09 (m, 2H), 6.97 (t, J=7.0 Hz, 1H), 6.91-6.77 (m, 2H), 5.05 (s, 2H); MS: ESI (positive): 434.5 (M+H).

EXAMPLE 75

[3-(2-Benzyl-1,1-dioxo-1,2-dihydro-1λ$^6$-benzo[e][1,2,3]thiadiazin-4-yl)-5-fluoro-2-methyl-indol-1-yl]-acetic Acid a.) 4-(5-Fluoro-2-methyl-1H-indol-3-yl)-2H-benzo[e][1,2,3]thiadiazine 1,1-dioxide. (Scheme 2)

AlCl$_3$ (1.2 g, 10.5 mmol) was added to a solution of 4-chloro-2H-benzo[e][1,2,3]thiadiazine 1,1-dioxide (1.5 g, 7.0 mmol) and 5-fluoro-2-methyl indole (1.0 g, 7.0 mmol) in DCE (35 mL), and stirred overnight at 70° C. The reaction solution was diluted with H$_2$O, and the product was extracted with a solution of CH$_2$Cl$_2$/EtOH (9/1, v/v). The extracted product was concentrated and purified via silica gel chromatography eluting with a gradient of 0 to 70% EtOAc in hexanes to afford 0.44 g (19%) of the sub-title compound. MS calculated for C$_{16}$H$_{12}$FN$_3$O$_2$S—H: 328, observed: 328.

b.) [3-(2-Benzyl-1,1-dioxo-1,2-dihydro-1λ$^6$-benzo[e][1,2,3]thiadiazin-4-yl)-5-fluoro-2-methyl-indol-1-yl]-acetic Acid tert-butyl Ester Benzyl bromide (10 µL, 67 µmol) and K$_2$CO$_3$ (10 mg, 72 µmol) were added to a solution of 4-(5-fluoro-2-methyl-1H-indol-3-yl)-2H-benzo[e][1,2,3]thiadiazine 1,1-dioxide (20 mg, 61 µmol) in CH$_3$CN (1 mL), and stirred overnight at 80° C. An additional amount of K$_2$CO$_3$ (10 mg, 72 µmol) and tert-butyl bromoacetate (14 µL, 92 µmol) was added, and the reaction mixture stirred an additional 2 h at 80° C. The reaction mixture was diluted with H$_2$O and CH$_2$Cl$_2$, and filtered through an Extrelut column. The Extrelut column was washed with CH$_2$Cl$_2$, and the filtrate was concentrated to afford the sub-title compound, which was carried onto the next step without further purification or characterization.

c.) [3-(2-Benzyl-1,1-dioxo-1,2-dihydro-1$\lambda^6$-benzo[e] [1,2,3]thiadiazin-4-yl)-5-fluoro-2-methyl-indol-1-yl]-acetic Acid {[3-(2-Benzyl-1,1-dioxo-1,2-dihydro-1$\lambda^6$-benzo[e][1,2,3]thiadiazin-4-yl)-5-fluoro-2-methyl-indol-1-yl]-acetic Acid tert-butyl Ester (61 μmol) was treated with TFA (2 mL) for 2 hours, concentrated, and purified by preparative LCMS to give the title compound. $^1$H NMR (d$_6$-DMSO) δ 8.14 (d, 1H), 7.92 (t, 1H), 7.81 (t, 1H), 7.46 (d, 1H), 7.38 (m, 6H), 6.88 (dt, 1H), 6.61 (dd, 1H), 4.96 (s, 2H), 4.49 (s, 2H), 2.08 (s, 3H) ppm. MS calculated for C$_{25}$H$_{20}$FN$_3$O$_4$S—H: 476, observed: 476.

EXAMPLE 76

{3-[2-(2-Chloro-benzyl)-1,1-dioxo-1,2-dihydro-1$\lambda^6$-benzo[e][1,2,3]thiadiazin-4-yl]-5-fluoro-2-methyl-indol-1-yl}-acetic Acid a.) {3-[2-(2-Chloro-benzyl)-1,1-dioxo-1,2-dihydro-1$\lambda^6$-benzo[e][1,2,3]thiadiazin-4-yl]-5-fluoro-2-methyl-indol-1-yl}-acetic Acid tert-butyl Ester. (Scheme 2)

2-Chlorobenzyl chloride (9 μL, 67 μmol) and K$_2$CO$_3$ (10 mg, 72 μmol) were added to a solution of 4-(5-fluoro-2-methyl-1H-indol-3-yl)-2H-benzo[e][1,2,3]thiadiazine 1,1-dioxide (20 mg, 61 μmol) in CH$_3$CN (1 mL), and stirred overnight at 80° C. An additional amount of K$_2$CO$_3$ (10 mg, 72 μmol) and tert-butyl bromoacetate (14 μL, 92 μmol) was added, and the reaction mixture stirred an additional 2 h at 80° C. The reaction mixture was diluted with H$_2$O and CH$_2$Cl$_2$, and filtered through an Extrelut column. The Extrelut column was washed with CH$_2$Cl$_2$, and the filtrate was concentrated to afford the sub-title compound, which was carried onto the next step without further purification or characterization.

b.) {3-[2-(2-Chloro-benzyl)-1,1-dioxo-1,2-dihydro-1$\lambda^6$-benzo[e][1,2,3]thiadiazin-4-yl]-5-fluoro-2-methyl-indol-1-yl}-acetic Acid {3-[2-(2-Chloro-benzyl)-1,1-dioxo-1,2-dihydro-1$\lambda^6$-benzo[e][1,2,3]thiadiazin-4-yl]-5-fluoro-2-methyl-indol-1-yl}-acetic Acid tert-butyl ester (61 mmol) was treated with TFA (2 mL) for 2 hours, concentrated, and purified by preparative LCMS to give the title compound. $^1$H NMR (d$_6$-DMSO) δ 8.18 (d, 1H), 7.94 (t, 1H), 7.83 (t, 1H), 7.45 (m, 6H), 6.88 (dt, 1H), 6.51 (dd, 1H), 5.19 (bs, 2H), 4.43 (s, 2H), 2.02 (s, 3H) ppm. MS calculated for C$_{25}$H$_{19}$FClN$_3$O$_4$S—H: 510, observed: 510.

EXAMPLE 77

{3-[2-(3-Chloro-benzyl)-1,1-dioxo-1,2-dihydro-1$\lambda^6$-benzo[e][1,2,3]thiadiazrn-4-yl]-5-fluoro-2-methyl-indol-1-yl}-acetic acid a.) {3-[2-(3-Chloro-benzyl)-1,1-dioxo-1,2-dihydro-1$\lambda^6$-benzo[e][1,2,3]thiadiazin-4-yl]-5-fluoro-2-methyl-indol-1-yl}-acetic acid tert-butyl ester. (Scheme 2)

3-Chlorobenzyl chloride (9 μL, 67 μmol) and K$_2$CO$_3$ (10 mg, 72 μmol) were added to a solution of 4-(5-fluoro-2-methyl-1H-indol-3-yl)-2H-benzo[e][1,2,3]thiadiazine 1,1-dioxide (20 mg, 61 μmol) in CH$_3$CN (1 mL), and stirred overnight at 80° C. An additional amount of K$_2$CO$_3$ (10 mg, 72 μmol) and tert-butyl bromoacetate (14 μL, 92 μmol) was added, and the reaction mixture stirred an additional 2 h at 80° C. The reaction mixture was diluted with H$_2$O and CH$_2$Cl$_2$, and filtered through an Extrelut column. The Extrelut column was washed with CH$_2$Cl$_2$, and the filtrate was concentrated to afford the sub-title compound, which was carried onto the next step without further purification or characterization.

b.) {3-[2-(3-Chloro-benzyl)-1,1-dioxo-1,2-dihydro-1$\lambda^6$-benzo[e][1,2,3]thiadiazin-4-yl]-5-fluoro-2-methyl-indol-1-yl}-acetic acid {3-[2-(3-Chloro-benzyl)-1,1-dioxo-1,2-dihydro-1$\lambda^6$-benzo[e][1,2,3]thiadiazin-4-yl]-5-fluoro-2-methyl-indol-1-yl}-acetic acid tert-butyl ester (61 μmol) was treated with TFA (2 mL) for 2 hours, concentrated, and purified by preparative LCMS to give the title compound. $^1$H NMR (d$_6$-DMSO) δ 8.18 (d, 1H), 7.92 (t, 1H), 7.84 (t, 1H), 7.45 (m, 6H), 6.90 (dt, 1H), 6.61 (dd, 1H), 5.10 (bs, 2H), 4.52 (s, 2H), 2.09 (s, 3H) ppm. MS calculated for C$_{25}$H$_{19}$FClN$_3$O$_4$S—H: 510, observed: 510.

EXAMPLE 78

{3-[2-(4-Chloro-benzyl)-1,1-dioxo-1,2-dihydro-1$\lambda^6$-benzo[e][1,2,3]thiadiazin-4-yl]-5-fluoro-2-methyl-indol-1-yl}-acetic acid a.) {3-[2-(4-Chloro-benzyl)-1,1-dioxo-1,2-dihydro-1$\lambda^6$-benzo[e][1,2,3]thiadiazin-4-yl]-5-fluoro-2-methyl-indol-1-yl}-acetic acid tert-butyl ester. (Scheme 2)

4-Chlorobenzyl chloride (11 mg, 67 μmol) and K$_2$CO$_3$ (10 mg, 72 μmol) were added to a solution of 4-(5-fluoro-2-methyl-1H-indol-3-yl)-2H-benzo[e][1,2,3]thiadiazine 1,1-dioxide (20 mg, 61 μmol) in CH$_3$CN (1 mL), and stirred overnight at 80° C. An additional amount of K$_2$CO$_3$ (10 mg, 72 μmol) and tert-butyl bromoacetate (14 μL, 92 μmol) was added, and the reaction mixture stirred an additional 2 h at 80° C. The reaction mixture was diluted with H$_2$O and CH$_2$Cl$_2$, and filtered through an Extrelut column. The Extrelut column was washed with CH$_2$Cl$_2$, and the filtrate was concentrated to afford the sub-title compound, which was carried onto the next step without further purification or characterization.

b.) {3-[2-(4-Chloro-benzyl)-1,1-dioxo-1,2-dihydro-1$\lambda^6$-benzo[e][1,2,3]thiadiazin-4-yl]-5-fluoro-2-methyl-indol-1-yl}-acetic acid {3-[2-(4-Chloro-benzyl)-1,1-dioxo-1,2-dihydro-1$\lambda^6$-benzo[e][1,2,3]thiadiazin-4-yl]-5-fluoro-2-methyl-indol-1-yl}-acetic acid tert-butyl ester (61 μmol) was treated with TFA (2 mL) for 2 hours, concentrated, and purified by preparative LCMS to give the title compound. $^1$H NMR (d$_6$-DMSO) δ 8.15 (d, 1H), 7.91 (t, 1H), 7.82 (t, 1H), 7.45 (m, 6H), 6.89 (dt, 1H), 6.60 (dd, 1H), 5.08 (bs, 2H), 4.59 (s, 2H), 2.08 (s, 3H) ppm. MS calculated for C$_{25}$H$_{19}$FClN$_3$O$_4$S—H: 510, observed: 510.

EXAMPLE 79

{3-[2-(3-Methoxy-benzyl)-1,1-dioxo-1,2-dihydro-1$\lambda^6$-benzo[e][1,2,3]thiadiazin-4-yl]-5-fluoro-2-methyl-indol-1-yl}-acetic acid a.) {3-[2-(3-Methoxy-benzyl)-1,1-dioxo-1,2-dihydro-1$\lambda^6$-benzo[e][1,2,3]thiadiazin-4-yl]-5-fluoro-2-methyl-indol-1-yl}-acetic acid tert-butyl ester. (Scheme 2)

3-Methoxybenzyl chloride (10 μL, 67 μmol) and K$_2$CO$_3$ (10 mg, 72 μmol) were added to a solution of 4-(5-fluoro-2-methyl-1H-indol-3-yl)-2H-benzo[e][1,2,3]thiadiazine 1,1-dioxide (20 mg, 61 μmol) in CH$_3$CN (1 mL), and stirred overnight at 80° C. An additional amount of K$_2$CO$_3$ (10 mg, 72 μmol) and tert-butyl bromoacetate (14 μL, 92 μmol) was added, and the reaction mixture stirred an additional 2 h at 80° C. The reaction mixture was diluted with H$_2$O and CH$_2$Cl$_2$, and filtered through an Extrelut column. The Extrelut column was washed with CH$_2$Cl$_2$, and the filtrate was concentrated to afford the sub-title compound, which was carried onto the next step without further purification or characterization.

b.) {3-[2-(3-Methoxy-benzyl)-1,1-dioxo-1,2-dihydro-1$\lambda^6$-benzo[e][1,2,3]thiadiazin-4-yl]-5-fluoro-2-methyl-indol-1-yl}-acetic acid {3-[2-(3-Methoxy-benzyl)-1,1-dioxo-1,2-dihydro-1$\lambda^6$-benzo[e][1,2,3]thiadiazin-4-yl]-5-fluoro-2-methyl-indol-1-yl}-acetic acid tert-butyl ester (61 μmol) was treated with TFA (2 mL) for 2 hours, concentrated, and purified by preparative LCMS to give the title compound. $^1$H NMR (d$_6$-DMSO) δ 8.13 (d, 1H), 7.91 (t, 1H), 7.84 (t, 1H), 7.48 (d, 1H), 7.38 (dd, 1H), 7.28 (t, 1H), 6.91 (m, 4H), 6.69 (dd, 1H), 5.06 (bs, 2H), 4.51 (s, 2H), 3.71 (s, 3H), 2.11 (s, 3H) ppm. MS calculated for C$_{26}$H$_{22}$FN$_3$O$_5$S—H: 506, observed: 506.

EXAMPLE 80

{3-[2-(4-Methoxy-benzyl)-1,1-dioxo-1,2-dihydro-1$\lambda^6$-benzo[e][1,2,3]thiadiazin-4-yl]-5-fluoro-2-methyl-indol-1-yl}-acetic acid a.) {3-[2-(4-Methoxy-benzyl)-1,1-dioxo-1,2-dihydro-1$\lambda^6$-benzo[e][1,2,3]thiadiazin-4-yl]-5-fluoro-2-methyl-indol-1-yl}-acetic acid tert-butyl ester. (Scheme 2)

4-Methoxybenzyl chloride (10 μL, 67 μmol) and K$_2$CO$_3$ (10 mg, 72 μmol) were added to a solution of 4-(5-fluoro-2-methyl-1H-indol-3-yl)-2H-benzo[e][1,2,3]thiadiazine 1,1-dioxide (20 mg, 61 μmol) in CH$_3$CN (1 mL), and stirred overnight at 80° C. An additional amount of K$_2$CO$_3$ (10 mg, 72 μmol) and tert-butyl bromoacetate (14 μL, 92 μmol) was added, and the reaction mixture stirred an additional 2 h at 80° C. The reaction mixture was diluted with H$_2$O and CH$_2$Cl$_2$, and filtered through an Extrelut column. The Extrelut column was washed with CH$_2$Cl$_2$, and the filtrate was concentrated to afford the sub-title compound, which was carried onto the next step without further purification or characterization.

b.) {3-[2-(4-Methoxy-benzyl)-1,1-dioxo-1,2-dihydro-1$\lambda^6$-benzo[e][1,2,3]thiadiazin-4-yl]-5-fluoro-2-methyl-indol-1-yl}-acetic acid {3-[2-(4-Methoxy-benzyl)-1,1-dioxo-1,2-dihydro-1$\lambda^6$-benzo[e][1,2,3]thiadiazin-4-yl]-5-fluoro-2-methyl-indol-1-yl}-acetic acid tert-butyl ester (61 μmol) was treated with TFA (2 mL) for 2 hours, concentrated, and purified by preparative LCMS to give the title compound. $^1$H NMR (d$_6$-DMSO) δ 8.12 (d, 1H), 7.91 (t, 1H), 7.81 (t, 1H), 7.44 (d, 1H), 7.32 (m, 3H), 6.92 (m, 3H), 6.62 (dd, 1H), 4.99 (bs, 2H), 4.51 (s, 2H.), 3.73 (s, 3H), 2.09 (s, 3H) ppm. MS calculated for C$_{26}$H$_{22}$FN$_3$O$_5$S—H: 506, observed: 506.

EXAMPLE 81

{3-[2-(2-Fluoro-benzyl)-1,1-dioxo-1,2-dihydro-1$\lambda^6$-benzo[e][1,2,3]thiadiazin-4-yl]-5-fluoro-2-methyl-indol-1-yl}-acetic acid a.) {3-[2-(2-Fluoro-benzyl)-1,1-dioxo-1,2-dihydro-1$\lambda^6$-benzo[e][1,2,3]thiadiazin-4-yl]-5-fluoro-2-methyl-indol-1-yl}-acetic acid tert-butyl ester. (Scheme 2)

2-Fluorobenzyl bromide (8 μL, 67 μmol) and K$_2$CO$_3$ (10 mg, 72 μmol) were added to a solution of 4-(5-fluoro-2-methyl-1H-indol-3-yl)-2H-benzo[e][1,2,3]thiadiazine 1,1-dioxide (20 mg, 61 μmol) in CH$_3$CN (1 mL), and stirred overnight at 80° C. An additional amount of K$_2$CO$_3$ (10 mg, 72 μmol) and tert-butyl bromoacetate (14 μL, 92 μmol) was added, and the reaction mixture stirred an additional 2 h at 80° C. The reaction mixture was diluted with H$_2$O and CH$_2$Cl$_2$, and filtered through an Extrelut column. The Extrelut column was washed with CH$_2$Cl$_2$, and the filtrate was concentrated to afford the sub-title compound, which was carried onto the next step without further purification or characterization.

b.) {3-[2-(2-Fluoro-benzyl)-1,1-dioxo-1,2-dihydro-1$\lambda^6$-benzo[e][1,2,3]thiadiazin-4-yl]-5-fluoro-2-methyl-indol-1-yl}-acetic acid {3-[2-(2-Fluoro-benzyl)-1,1-dioxo-1,2-dihydro-1$\lambda^6$-benzo[e][1,2,3]thiadiazin-4-yl]-5-fluoro-2-methyl-indol-1-yl}-acetic acid tert-butyl ester (61 μmol) was treated with TFA (2 mL) for 2 hours, concentrated, and purified by preparative LCMS to give the title compound. $^1$H NMR (d$_6$-DMSO) δ 7.94 (d, 1H), 7.72 (t, 1H), 7.63 (t, 1H), 7.22 (d, 4H), 7.02 (m, 2H), 6.69 (dt, 1H), 6.38 (dd, 1H), 4.92 (bs, 2H), 4.51 (s, 2H), 1.86 (s, 3H) ppm. MS calculated for C$_{25}$H$_{19}$F$_2$N$_3$O$_4$S—H: 494, observed: 494.

EXAMPLE 82

{3-[2-(3-Fluoro-benzyl)-1,1-dioxo-1,2-dihydro-1$\lambda^6$-benzo[e][1,2,3]thiadiazin-4-yl]-5-fluoro-2-methyl-indol-1-yl}-acetic acid a.) {3-[2-(3-Fluoro-benzyl)-1,1-dioxo-1,2-dihydro-1$\lambda^6$-benzo[e][1,2,3]thiadiazin-4-yl]-5-fluoro-2-methyl-indol-1-yl}-acetic acid tert-butyl ester. (Scheme 2)

3-Fluorobenzyl bromide (8 μL, 67 μmol) and K$_2$CO$_3$ (10 mg, 72 μmol) were added to a solution of 4-(5-fluoro-2-methyl-1H-indol-3-yl)-2H-benzo[e][1,2,3]thiadiazine 1,1-dioxide (20 mg, 61 μmol) in CH$_3$CN (1 mL), and stirred overnight at 80° C. An additional amount of K$_2$CO$_3$ (10 mg, 72 μmol) and tert-butyl bromoacetate (14 μL, 92 μmol) was added, and the reaction mixture stirred an additional 2 h at 80° C. The reaction mixture was diluted with H$_2$O and CH$_2$Cl$_2$, and filtered through an Extrelut column. The Extrelut column was washed with CH$_2$Cl$_2$, and the filtrate was concentrated to afford the sub-title compound, which was carried onto the next step without further purification or characterization.

b.) {3-[2-(3-Fluoro-benzyl)-1,1-dioxo-1,2-dihydro-1λ$^6$-benzo[e][1,2,3]thiadiazin-4-yl]-5-fluoro-2-methyl-indol-1-yl}-acetic acid {3-[2-(3-Fluoro-benzyl)-1,1-dioxo-1,2-dihydro-1λ$^6$-benzo[e][1,2,3]thiadiazin-4-yl]-5-fluoro-2-methyl-indol-1-yl}-acetic acid tert-butyl ester (61 µmol) was treated with TFA (2 mL) for 2 hours, concentrated, and purified by preparative LCMS to give the title compound. $^1$H NMR (d$_6$-DMSO) δ 8.17 (d, 1H), 7.95 (t, 1H), 7.86 (t, 1H), 7.42 (m, 3H), 7.19 (m, 3H), 6.89 (dt, 1H), 6.61 (dd, 1H), 5.09 (bs, 2H), 4.53 (s, 2H), 2.09 (s, 3H) ppm. MS calculated for C$_{25}$H$_{19}$F$_2$N$_3$O$_4$S—H: 494, observed: 494.

EXAMPLE 83

{3-[2-(4-Fluoro-benzyl)-1,1-dioxo-1,2-dihydro-1λ$^6$-benzo[e][1,2,3]thiadiazin-4-yl]-5-fluoro-2-methyl-indol-1-yl}-acetic acid a.) {3-[2-(4-Fluoro-benzyl)-1,1-dioxo-1,2-dihydro-1λ$^6$-benzo[e][1,2,3]thiadiazin-4-yl]-5-fluoro-2-methyl-indol-1-yl}-acetic acid tert-butyl ester. (Scheme 2)

4-Fluorobenzyl bromide (8 µL, 67 µmol) and K$_2$CO$_3$ (10 mg, 72 µmol) were added to a solution of 4-(5-fluoro-2-methyl-1H-indol-3-yl)-2H-benzo[e][1,2,3]thiadiazine 1,1-dioxide (20 mg, 61 µmol) in CH$_3$CN (1 mL), and stirred overnight at 80° C. An additional amount of K$_2$CO$_3$ (10 mg, 72 µmol) and tert-butyl bromoacetate (14 µL, 92 µmol) was added, and the reaction mixture stirred an additional 2 h at 80° C. The reaction mixture was diluted with H$_2$O and CH$_2$Cl$_2$, and filtered through an Extrelut column. The Extrelut column was washed with CH$_2$Cl$_2$, and the filtrate was concentrated to afford the sub-title compound, which was carried onto the next step without further purification or characterization.

b.) {3-[2-(4-Fluoro-benzyl)-1,1-dioxo-1,2-dihydro-1λ$^6$-benzo[e][1,2,3]thiadiazin-4-yl]-5-fluoro-2-methyl-indol-1-yl}-acetic acid {3-[2-(4-Fluoro-benzyl)-1,1-dioxo-1,2-dihydro-1λ$^\neq$-benzo[e][1,2,3]thiadiazin-4-yl]-5-fluoro-2-methyl-indol-1-yl}-acetic acid tert-butyl ester (61 µmol) was treated with TFA (2 mL) for 2 hours, concentrated, and purified by preparative LCMS to give the title compound. $^1$H NMR (d$_6$-DMSO) δ 8.15 (d, 1H), 7.93 (t, 1H), 7.84 (t, 1H), 7.47 (m, 3H), 7.38 (dd, 1H), 7.21 (m, 2H), 6.89 (dt, 1H), 6.57 (dd, 1H), 5.09 (bs, 2H), 4.51 (s, 2H), 2.09 (s, 3H) ppm. MS calculated for C$_{25}$H$_{19}$F$_2$N$_3$O$_4$S—H: 494, observed: 494.

EXAMPLE 84

{3-[2-(4-Trifluoromethoxy-benzyl)-1,1-dioxo-1,2-dihydro-1λ$^6$-benzo[e][1,2,3]thiadiazin-4-yl]-5-fluoro-2-methyl-indol-1-yl}-acetic acid a.) {3-[2-(4-Trifluoromethoxy-benzyl)-1,1-dioxo-1,2-dihydro-1λ$^6$-benzo[e][1,2,3]thiadiazin-4-yl]-5-fluoro-2-methyl-indol-1-yl}-acetic acid tert-butyl ester. (Scheme 2)

4-Trifluoromethoxybenzyl bromide (11 µL, 67 µmol) and K$_2$CO$_3$ (10 mg, 72 Amok) were added to a solution of 4-(5-fluoro-2-methyl-1H-indol-3-yl)-2H-benzo[e][1,2,3]thiadiazine 1,1-dioxide (20 mg, 61 µmol) in CH$_3$CN (1 mL), and stirred overnight at 80° C. An additional amount of K$_2$CO$_3$ (10 mg, 72 µmol) and tert-butyl bromoacetate (14 µL, 92 µmol) was added, and the reaction mixture stirred an additional 2 h at 80° C. The reaction mixture was diluted with H$_2$O and CH$_2$Cl$_2$, and filtered through an Extrelut column. The Extrelut column was washed with CH$_2$Cl$_2$, and the filtrate was concentrated to afford the sub-title compound, which was carried onto the next step without further purification or characterization.

b.) {3-[2-(4-Trifluoromethoxy-benzyl)-1,1-dioxo-1,2-dihydro-1λ$^6$-benzo[e][1,2,3]thiadiazin-4-yl]-5-fluoro-2-methyl-indol-1-yl}-acetic acid {3-[2-(4-Trifluoromethoxy-benzyl)-1,1-dioxo-1,2-dihydro-1λ$^6$-benzo[e][1,2,3]thiadiazin-4-yl]-5-fluoro-2-methyl-indol-1-yl}-acetic acid tert-butyl ester (61 µmol) was treated with TFA (2 mL) for 2 hours, concentrated, and purified by preparative LCMS to give the title compound. $^1$H NMR (d$_6$-DMSO) δ 8.17 (d, 1H), 7.93 (t, 1H), 7.85 (t, 1H), 7.50 (m, 3H), 7.38 (m, 3H), 6.89 (dt, 1H), 6.59 (dd, 1H), 5.11 (bs, 2H), 4.52 (s, 2H), 2.08 (s, 3H) ppm. MS calculated for C$_{26}$H$_{19}$F$_4$N$_3$O$_5$S—H: 560, observed: 560.

EXAMPLE 85

{3-[2-(3-Trifluoromethyl-benzyl)-1,1-dioxo-1,2-dihydro-1λ$^6$-benzo[e][1,2,3]thiadiazin-4-yl]-5-fluoro-2-methyl-indol-1-yl}-acetic acid a.) (3-[2-(3-Trifluoromethyl-benzyl)-1,1-dioxo-1,2-dihydro-1λ$^6$-benzo[e][1,2,3]thiadiazin-4-yl]-5-fluoro-2-methyl-indol-1-yl}-acetic acid tert-butyl ester. (Scheme 2)

3-Trifluoromethylbenzyl bromide (10 µL, 67 µmol) and K$_2$CO$_3$ (10 mg, 72 µmol) were added to a solution of 4-(5-fluoro-2-methyl-1H-indol-3-yl)-2H-benzo[e][1,2,3]thiadiazine 1,1-dioxide (20 mg, 61 µmol) in CH$_3$CN (1 mL), and stirred overnight at 80° C. An additional amount of K$_2$CO$_3$ (10 mg, 72 µmol) and tert-butyl bromoacetate (14 mL, 92 µmol) was added, and the reaction mixture stirred an additional 2 h at 80° C. The reaction mixture was diluted with H$_2$O and CH$_2$Cl$_2$, and filtered through an Extrelut column. The Extrelut column was washed with CH$_2$Cl$_2$, and the filtrate was concentrated to afford the sub-title compound, which was carried onto the next step without further purification or characterization.

b.) {3-[2-(3-Trifluoromethyl-benzyl)-1,1-dioxo-1,2-dihydro-1λ$^6$-benzo[e][1,2,3]thiadiazin-4-yl]-5-fluoro-2-methyl-indol-1-yl}-acetic acid {3-[2-(3-Trifluoromethyl-benzyl)-1,1-dioxo-1,2-dihydro-1λ$^6$-benzo[e][1,2,3]thiadiazin-4-yl]-5-fluoro-2-methyl-indol-1-yl}-acetic acid tert-butyl ester (61 µmol) was treated with TFA (2 mL) for 2 hours, concentrated, and purified by preparative LCMS to give the title compound. $^1$H NMR (d$_6$-DMSO) δ 8.18 (d, 1H), 7.95 (t, 1H), 7.86 (t, 1H), 7.70 (m, 4H), 7.48 (d, 1H), 7.37 (dd, 1H), 6.89 (dt, 1H), 6.52 (dd, 1H), 5.18 (bs, 2H), 4.48 (s, 2H), 2.07 (s, 3H) ppm. MS calculated for $C_{26}H_{19}F_4N_3O_4S$—H: 544, observed: 544.

EXAMPLE 86

{3-[2-(1-phenyl-ethyl)-1,1-dioxo-1,2-dihydro-1$\lambda^6$-benzo[e][1,2,3]thiadiazin-4-yl]-5-fluoro-2-methyl-indol-1-yl}-acetic acid a.) {3-[2-(1-phenyl-ethyl)-1,1-dioxo-1$\lambda^6$-benzo[e][1,2,3]thiadiazin-4-yl]-5-fluoro-2-methyl-indol-1-yl}-acetic acid tert-butyl ester. (Scheme 2)

(1-Bromoethyl)benzene (9 mL, 67 μmol) and $K_2CO_3$ (10 mg, 72 μmol) were added to a solution of 4-(5-fluoro-2-methyl-1H-indol-3-yl)-2H-benzo[e][1,2,3]thiadiazine 1,1-dioxide (20 mg, 61 μmol) in $CH_3CN$ (1 mL), and stirred overnight at 80° C. An additional amount of $K_2CO_3$ (10 mg, 72 μmol) and tert-butyl bromoacetate (14 μL, 92 μmol) was added, and the reaction mixture stirred an additional 2 h at 80° C. The reaction mixture was diluted with $H_2O$ and $CH_2Cl_2$, and filtered through an Extrelut column. The Extrelut column was washed with $CH_2Cl_2$, and the filtrate was concentrated to afford the sub-title compound, which was carried onto the next step without further purification or characterization.

b.) {3-[2-(1-phenyl-ethyl)-1,1-dioxo-1,2-dihydro-1$\lambda^6$-benzo[e][1,2,3]thiadiazin-4-yl]-5-fluoro-2-methyl-indol-1-yl}-acetic acid {3-[2-(1-Phenyl-ethyl)-1,1-dioxo-1,2-dihydro-1$\lambda^6$-benzo[e][1,2,3]thiadiazin-4-yl]-5-fluoro-2-methyl-indol-1-yl}-acetic acid tert-butyl ester (61 μmol) was treated with TFA (2 mL) for 2 hours, concentrated, and purified by preparative LCMS to give the title compound. $^1$H NMR ($d_6$-DMSO) δ 8.11 (d, 1H), 7.91 (t, 1H), 7.81 (t, 1H), 7.36 (m, 8H), 6.91 (m, 1H), 5.72 (m, 1H), 4.52 (s, 2H), 2.07 (s, 3H), 1.85 (d, 3H) ppm. MS calculated for $C_{26}H_{22}FN_3O_4S$—H: 490, observed: 490.

EXAMPLE 87

{3-[2-phenethyl-1,1-dioxo-1,2-dihydro-1$\lambda^6$-benzo[e][1,2,3]thiadiazin-4-yl]-5-fluoro-2-methyl-indol-1-yl}-acetic acid a.) {3-[2-phenethyl-1,1-dioxo-1,2-dihydro-1$\lambda^6$--benzo[e][1,2,3]thiadiazin-4-yl]-5-fluoro-2-methyl-indol-1-yl}-acetic acid tert-butyl ester. (Scheme 2)

(2-Bromoethyl)benzene (9 μL, 67 μmol) and $K_2CO_3$ (10 mg, 72 μmol) were added to a solution of 4-(5-fluoro-2-methyl-1H-indol-3-yl)-2H-benzo[e][1,2,3]thiadiazine 1,1-dioxide (20 mg, 61 μmol) in $CH_3CN$ (1 mL), and stirred overnight at 80° C. An additional amount of $K_2CO_3$ (10 mg, 72 μmol) and tert-butyl bromoacetate (14 μL, 92 μmol) was added, and the reaction mixture stirred an additional 2 h at 80° C. The reaction mixture was diluted with $H_2O$ and $CH_2Cl_2$, and filtered through an Extrelut column. The Extrelut column was washed with $CH_2Cl_2$, and the filtrate was concentrated to afford the sub-title compound, which was carried onto the next step without further purification or characterization.

b.) {3-[2-phenethyl-1,1-dioxo-1,2-dihydro-1$\lambda^6$--benzo[e][1,2,3]thiadiazin-4-yl]-5-fluoro-2-methyl-indol-1-yl}-acetic acid {3-[2-Phenethyl-1,1-dioxo-1,2-dihydro-1$\lambda^6$-benzo[e][1,2,3]thiadiazin-4-yl]-5-fluoro-2-methyl-indol-1-yl}-acetic acid tert-butyl ester (61 μmol) was treated with TFA (2 mL) for 2 hours, concentrated, and purified by preparative LCMS to give the title compound. $^1$H NMR ($d_6$-DMSO) δ 8.07 (d, 1H), 7.89 (t, 1H), 7.83 (t, 1H), 7.45 (m, 2H), 7.20 (m, 5H), 6.91 (m, 2H), 4.56 (s, 2H), 4.11 (t, 2H), 3.12 (t, 2H), 2.21 (s, 3H) ppm. MS calculated for $C_{26}H_{22}FN_3O_4S$—H: 490, observed: 490.

EXAMPLE 88

{3-[2-(2-Phenoxy-ethyl)-1,1-dioxo-1,2-dihydro-1$\lambda^6$-benzo[e][1,2,3]thiadiazin-4-yl]-5-fluoro-2-methyl-indol-1-yl}-acetic acid a.) {3-[2-(2-Phenoxy-ethyl)-1,1-dioxo-1,2-dihydro-1$\lambda^6$-benzo[e][1,2,3]thiadiazin-4-yl]-5-fluoro-2-methyl-indol-1-yl}-acetic acid tert-butyl ester. (Scheme 2)

β-Bromophenetole (14 mg, 67 μmol) and $K_2CO_3$ (10 mg, 72 μmol) were added to a solution of 4-(5-fluoro-2-methyl-1H-indol-3-yl)-2H-benzo[e][1,2,3]thiadiazine 1,1-dioxide (20 mg, 61 μmol) in $CH_3CN$ (1 mL), and stirred overnight at 80° C. An additional amount of $K_2CO_3$ (10 mg, 72 μmol) and tert-butyl bromoacetate (14 μL, 92 μmol) was added, and the reaction mixture stirred an additional 2 h at 80° C. The reaction mixture was diluted with $H_2O$ and $CH_2Cl_2$, and filtered through an Extrelut column. The Extrelut column was washed with $CH_2Cl_2$, and the filtrate was concentrated to afford the sub-title compound, which was carried onto the next step without further purification or characterization.

b.) {3-[2-(2-Phenoxy-ethyl)-1,1-dioxo-1,2-dihydro-1$\lambda^6$-benzo[e][1,2,3]thiadiazin-4-yl]-5-fluoro-2-methyl-indol-1-yl}-acetic acid {3-[2-(2-Phenoxy-ethyl)-1,1-dioxo-1,2-dihydro-1$\lambda^6$-benzo[e][1,2,3]thiadiazin-4-yl]-5-fluoro-2-methyl-indol-1-yl}-acetic acid tert-butyl ester (61 μmol) was treated with TFA (2 mL) for 2 hours, concentrated, and purified by preparative LCMS to give the title compound. $^1$H NMR ($d_6$-DMSO) δ 8.12 (d, 1H), 7.92 (t, 1H), 7.82 (t, 1H), 7.46 (m, 2H), 7.22 (m, 2H), 6.96 (m, 5H), 4.58 (s, 2H), 4.39 (t, 2H), 4.28 (t, 2H), 2.21 (s, 3H) ppm. MS calculated for $C_{26}H_{22}FN_3O_5S$—H: 506, observed: 506.

EXAMPLE 89

(3-{2-[2-(4-Chloro-phenoxy)-ethyl]-1,1-dioxo-1,2-dihydro-1$\lambda^6$-benzo[e][1,2,3]thiadiazin-4-yl}-5-fluoro-2-methyl-indol-1-yl)-acetic acid a.) (3-{2-[2-(4-Chloro-phenoxy)-ethyl]-1,1-dioxo-1,2-dihydro-1$\lambda^6$-benzo[e][1,2,3]thiadiazin-4-yl}-5-fluoro-2-methyl-indol-1-yl)-acetic acid tert-butyl ester. (Scheme 2)

4-Chlorophenyl 2-bromoethyl ether (16 mg, 67 μmol) and $K_2CO_3$ (10 mg, 72 μmol) were added to a solution of 4-(5-fluoro-2-methyl-1H-indol-3-yl)-2H-benzo[e][1,2,3]thiadiazine 1,1-dioxide (20 mg, 61 μmol) in $CH_3CN$ (1 mL), and stirred overnight at 80° C. An additional amount of $K_2CO_3$ (10 mg, 72 µmol) and tert-butyl bromoacetate (14 µL, 92 µmol) was added, and the reaction mixture stirred an additional 2 h at 80° C. The reaction mixture was diluted with $H_2O$ and $CH_2Cl_2$, and filtered through an Extrelut column. The Extrelut column was washed with $CH_2Cl_2$, and the filtrate was concentrated to afford the sub-title compound, which was carried onto the next step without further purification or characterization.

b.) (3-{2-[2-(4-Chloro-phenoxy)-ethyl]-1,1-dioxo-1, 2-dihydro-1λ⁶-benzo[e][1,2,3]thiadiazin-4-yl}-5-fluoro-2-methyl-indol-1-yl)-acetic acid (3-{2-[2-(4-Chloro-phenoxy)-ethyl]-1,1-dioxo-1,2-dihydro-1,6-benzo[e][1,2,3]thiadiazin-4-yl}-5-fluoro-2-methyl-indol-1-yl)-acetic acid tert-butyl ester (61 µmol) was treated with TFA (2 mL) for 2 hours, concentrated, and purified by preparative LCMS to give the title compound. $^1$H NMR ($d_6$-DMSO) δ 8.11 (d, 1H), 7.92 (t, 1H), 7.83 (t, 1H), 7.46 (m, 2H), 7.24 (m, 2H), 6.95 (m, 4H), 4.52 (s, 2H), 4.39 (t, 2H), 4.27 (t, 2H), 2.20 (s, 3H) ppm. MS calculated for $C_{26}H_{21}FClN_3O_5S$—H: 540, observed: 540.

EXAMPLE 90

{3-[2-(3,5-Dimethyl-isoxazol-4-ylmethyl)-1,1-dioxo-1,2-dihydro-1λ⁶-benzo[e][1,2,3]thiadiazin-4-yl]-5-fluoro-2-methyl-indol-1-yl}-acetic acid a.) {3-[2-(3,5-Dimethyl-isoxazol-4-ylmethyl)-1,1-dioxo-1,2-dihydro-1λ⁶-benzo[e][1,2,3]thiadiazin-4-yl]-5-fluoro-2-methyl-indol-1-yl}-acetic acid tert-butyl ester. (Scheme 2)

4-Chloromethyl-3,5-dimethylisoxazole (8 mL, 67 µmol) and $K_2CO_3$ (10 mg, 72 µmol) were added to a solution of 4-(5-fluoro-2-methyl-1H-indol-3-yl)-2H-benzo[e][1,2,3] thiadiazine 1,1-dioxide (20 mg, 61 µmol) in $CH_3CN$ (1 mL), and stirred overnight at 80° C. An additional amount of $K_2CO_3$ (10 mg, 72 µmol) and tert-butyl bromoacetate (14 mL, 92 Amok) was added, and the reaction mixture stirred an additional 2 h at 80° C. The reaction mixture was diluted with $H_2O$ and $CH_2Cl_2$, and filtered through an Extrelut column. The Extrelut column was washed with $CH_2Cl_2$, and the filtrate was concentrated to afford the sub-title compound, which was carried onto the next step without further purification or characterization.

b.) {3-[2-(3,5-Dimethyl-isoxazol-4-ylmethyl)-1,1-dioxo-1,2-dihydro-1λ⁶-benzo[e][1,2,3]thiadiazin-4-yl]-5-fluoro-2-methyl-indol-1-yl}-acetic acid {3-[2-(3,5-Dimethyl-isoxazol-4-ylmethyl)-1,1-dioxo-1,2-dihydro-1λ⁶-benzo[e][1,2,3]thiadiazin-4-yl]-5-fluoro-2-methyl-indol-1-yl}-acetic acid tert-butyl ester (61 µmol) was treated with TFA (2 mL) for 2 hours, concentrated, and purified by preparative LCMS to give the title compound. $^1$H NMR ($d_6$-DMSO) δ 7.99 (d, 1H), 7.78 (t, 1H), 7.70 (t, 1H), 7.30 (d, 1H), 7.27 (dd, 1H), 6.79 (dt, 1H), 6.62 (dd, 1H), 4.71 (s, 2H), 4.39 (s, 2H), 2.23 (s, 3H), 2.04 (s, 3H), 1.98 (s, 3H) ppm. MS calculated for $C_{24}H_{21}FN_4O_5S$—H: 495, observed: 495.

EXAMPLE 91

[3-(2-Ethyl-1,1-dioxo-1,2-dihydro-1λ⁶-benzo[e][1,2,3]thiadiazin-4-yl)-5-fluoro-2-methyl-indol-1-yl]-acetic acid a.) [3-(2-Ethyl-1,1-dioxo-1,2-dihydro-1λ⁶-benzo[e][1,2,3]thiadiazin-4-yl)-5-fluoro-2-methyl-indol-1-yl]-acetic acid tert-butyl ester. (Scheme 2)

Iodoethane (5 µL, 67 µmol) and $K_2CO_3$ (10 mg, 72 µmol) were added to a solution of 4-(5-fluoro-2-methyl-1H-indol-3-yl)-2H-benzo[e][1,2,3]thiadiazine 1,1-dioxide (20 mg, 61 µmol) in $CH_3CN$ (1 mL), and stirred overnight at 80° C. An additional amount of $K_2CO_3$ (10 mg, 72 µmol) and tert-butyl bromoacetate (14 µL, 92 µmol) was added, and the reaction mixture stirred an additional 2 h at 80° C. The reaction mixture was diluted with $H_2O$ and $CH_2Cl_2$, and filtered through an Extrelut column. The Extrelut column was washed with $CH_2Cl_2$, and the filtrate was concentrated to afford the sub-title compound, which was carried onto the next step without further purification or characterization.

b.) [3-(2-Ethyl-1,1-dioxo-1,2-dihydro-1λ⁶-benzo[e][1,2,3]thiadiazin-4-yl)-5-fluoro-2-methyl-indol-1-yl]-acetic acid

[3-(2-Ethyl-1,1-dioxo-1,2-dihydro-1λ⁶-benzo[e][1,2,3]thiadiazin-4-yl)-5-fluoro-2-methyl-indol-1-yl]-acetic acid tert-butyl ester (61 µmol) was treated with TFA (2 mL) for 2 hours, concentrated, and purified by preparative LCMS to give the title compound. $^1$H NMR ($d_6$-DMSO) δ 8.09 (d, 1H), 7.91 (t, 1H), 7.84 (t, 1H), 7.48 (d, 1H), 7.42 (dd, 1H), 6.97 (m, 2H), 4.52 (s, 2H), 3.96 (q, 2H), 2.21 (s, 3H), 1.39 (t, 3H) ppm. MS calculated for $C_{20}H_{18}FN_3O_4S$—H: 414, observed: 414.

EXAMPLE 92

[3-(2-Propyl-1,1-dioxo-1,2-dihydro-1λ⁶-benzo[e][1,2,3]thiadiazin-4-yl)-5-fluoro-2-methyl-indol-1-yl]-acetic acid a.) [3-(2-Propyl-1,1-dioxo-1,2-dihydro-1λ⁶-benzo[e][1,2,3]thiadiazin-4-yl)-5-fluoro-2-methyl-indol-1-yl]-acetic acid tert-butyl ester. (Scheme 2)

1-Iodopropane (7 µL, 67 µmol) and $K_2CO_3$ (10 mg, 72 µmol) were added to a solution of 4-(5-fluoro-2-methyl-1-indol-3-yl)-2H-benzo[e][1,2,3]thiadiazine 1,1-dioxide (20 mg, 61 Amok) in $CH_3CN$ (1 mL), and stirred overnight at 80° C. An additional amount of $K_2CO_3$ (10 mg, 72 Amok) and tert-butyl bromoacetate (14 µL, 92 µmol) was added, and the reaction mixture stirred an additional 2 h at 80° C. The reaction mixture was diluted with $H_2O$ and $CH_2Cl_2$, and filtered through an Extrelut column. The Extrelut column was washed with $CH_2Cl_2$, and the filtrate was concentrated to afford the sub-title compound, which was carried onto the next step without further purification or characterization.

b.) [3-(2-Propyl-1,1-dioxo-1,2-dihydro-1λ⁶-benzo[e][1,2,3]thiadiazin-4-yl)-5-fluoro-2-methyl-indol-1-yl]-acetic acid

[3-(2-Propyl-1,1-dioxo-1,2-dihydro-1λ⁶-benzo[e][1,2,3]thiadiazin-4-yl)-5-fluoro-2-methyl-indol-1-yl]-acetic acid tert-butyl ester (61 µmol) was treated with TFA (2 mL) for 2 hours, concentrated, and purified by preparative LCMS to give the title compound. $^1$H NMR (d$_6$-DMSO) δ 8.10 (d, 1H), 7.91 (t, 1H), 7.84 (t, 1H), 7.47 (m, 2H), 6.97 (m, 2H), 4.57 (s, 2H), 3.86 (t, 2H), 2.23 (s, 3H), 1.84 (m, 2H), 0.92 (t, 3H) ppm. MS calculated for C$_{21}$H$_{20}$FN$_3$O$_4$S—H: 428, observed: 428.

EXAMPLE 93

[3-(2-Isopropyl-1,1-dioxo-1,2-dihydro-1λ$^6$-benzo[e] [1,2,3]thiadiazin-4-yl)-5-fluoro-2-methyl-indol-1-yl]-acetic acid a.) [3-(2-Isopropyl-1,1-dioxo-1,2-dihydro-1λ$^6$-benzo [e][1,2,3]thiadiazin-4-yl)-5-fluoro-2-methyl-indol-1-yl]-acetic acid tert-butyl ester. (Scheme 2)

2-Iodopropane (7 µL, 67 µmol) and K$_2$CO$_3$ (10 mg, 72 mmol) were added to a solution of 4-(5-fluoro-2-methyl-1H-indol-3-yl)-2H-benzo[e][1,2,3]thiadiazine 1,1-dioxide (20 mg, 61 Amok) in CH$_3$CN (1 mL), and stirred overnight at 80° C. An additional amount of K$_2$CO$_3$ (10 mg, 72 µmol) and tert-butyl bromoacetate (14 mL, 92 µmol) was added, and the reaction mixture stirred an additional 2 h at 80° C. The reaction mixture was diluted with H$_2$O and CH$_2$Cl$_2$, and filtered through an Extrelut column. The Extrelut column was washed with CH$_2$Cl$_2$, and the filtrate was concentrated to afford the sub-title compound, which was carried onto the next step without further purification or characterization.

b.) [3-(2-Isopropyl-1,1-dioxo-1,2-dihydro-1λ$^6$-benzo [e][1,2,3]thiadiazin-4-yl)-5-fluoro-2-methyl-indol-1-yl]-acetic acid

[3-(2-Isopropyl-1,1-dioxo-1,2-dihydro-1λ$^6$-benzo[e][1,2, 3]thiadiazin-4-yl)-5-fluoro-2-methyl-indol-1-yl]-acetic acid tert-butyl ester (61 µmol) was treated with TEA (2 mL) for 2 hours, concentrated, and purified by preparative LCMS to give the title compound. $^1$H NMR (d$_6$-DMSO) δ 8.08 (d, 1H), 7.90 (t, 1H), 7.83 (t, 1H), 7.47 (m, 2H), 6.97 (m, 2H), 4.71 (m, 1H), 4.53 (s, 2H), 2.23 (s, 3H), 1.47 (m, 6H)) ppm. MS calculated for C$_{21}$H$_{20}$FN$_3$O$_4$S—H: 428, observed: 428.

EXAMPLE 94

[3-(2-Cyclohexyl-1,1-dioxo-1,2-dihydro-1λ$^6$-benzo [e][1,2,3]thiadiazin-4-yl)-5-fluoro-2-methyl-indol-1-yl]-acetic acid a.) [3-(2-Cyclohexyl-1,1-dioxo-1,2-dihydro-1-benzo [e][1,2,3]thiadiazin-4-yl)-5-fluoro-2-methyl-indol-1-yl]-acetic acid tert-butyl ester. (Scheme 2)

Cyclohexyl bromide (8 µL, 67 µmol) and K$_2$CO$_3$ (10 mg, 72 µmol) were added to a solution of 4-(5-fluoro-2-methyl-1H-indol-3-yl)-2H-benzo[e][1,2,3]thiadiazine 1,1-dioxide (20 mg, 61 µmol) in CH$_3$CN (1 mL), and stirred overnight at 80° C. An additional amount of K$_2$CO$_3$ (10 mg, 72 µmol) and tert-butyl bromoacetate (14 µL, 92 µmol) was added, and the reaction mixture stirred an additional 2 h at 80° C. The reaction mixture was diluted with H$_2$O and CH$_2$Cl$_2$, and filtered through an Extrelut column. The Extrelut column was washed with CH$_2$Cl$_2$, and the filtrate was concentrated to afford the sub-title compound, which was carried onto the next step without further purification or characterization.

b.) [3-(2-Cyclohexyl-1,1-dioxo-1,2-dihydro-1λ$^6$-benzo[e][1,2,3]thiadiazin-4-yl)-5-fluoro-2-methyl-indol-1-yl]-acetic acid

[3-(2-Cyclohexyl-1,1-dioxo-1,2-dihydro-1λ$^6$-benzo[e][1, 2,3]thiadiazin-4-yl)-5-fluoro-2-methyl-indol-1-yl]-acetic acid tert-butyl ester (61 Amok) was treated with TFA (2 mL) for 2 hours, concentrated, and purified by preparative LCMS to give the title compound. $^1$H NMR (d$_6$-DMSO) δ 8.08 (d, 1H), 7.88 (t, 1H), 7.81 (t, 1H), 7.42 (m, 2H), 6.91 (m, 2H), 4.55 (s, 2H), 4.29 (m, 1H), 2.23 (s, 3H), 1.88 (m, 5H), 1.65 (m, 2H), 1.47 (m, 2H), 1.11 (m, 1H) ppm. MS calculated for C$_{24}$H$_{24}$FN$_3$O$_4$S—H: 468, observed: 468.

EXAMPLE 95

CRTH-2 Binding Assay

A CRTH2 binding assay was developed to measure the ability of compounds to inhibit the binding of PGD$_2$ to human CRTH2 using a scintillation proximity assay.

Membranes containing hCRTH2 receptors were prepared from HEK 293EBNA-hCRTH2 cells (a HEK 293EBNA cell line stably expressing human CRTH2). The cells were grown to confluency, harvested and washed with PBS. The cells were resuspended in 10 mM Hepes pH 7.4, 1 mM EDTA and protease inhibitors and incubated for 30 min on ice. The cells were homogenized and centrifuged for 10 min at 1000×g. The supernate was centrifuged for 30 min at 100,000×g and the membrane pellet was then resusupended in 10 mM Hepes pH 7.4 and 1 mM EDTA. The protein concentration of the membrane preparation was determined by Bradford assay (Bio-Rad).

The ability of compounds to inhibit the interaction of PGD$_2$ to human CRTH2 was determined at seven compound concentrations. Compounds were serially diluted in DMSO then diluted into CRTH2 buffer without glycerol (10 mM Hepes pH 7.4, 1 mM EDTA, 10 mM MnCl$_2$) to six times the final desired concentration. 20 µL of the diluted compounds were transferred into non-surface binding 96 well plates (Corning). Each concentration was done in triplicate. In addition to test compounds, each plate contained 12 control wells. Six of these wells contained 20 µL of CRTH2 buffer without glycerol. These wells were used to measure total binding. Six wells contained 20 µL of CRTH2 buffer without glycerol plus 1.5 mM indomethacin. These wells were used to measure non-specific binding. Next, HEK 293EBNA-hCRTH2 membranes were resuspended in CRTH2 buffer with glycerol (10 mM Hepes pH 7.4, 1 mM EDTA, 10 mM MnCl$_2$, 25% glycerol) so that the final concentration was approximately 20 µg protein/100 µL. Polylysine coated yttrium silicate SPA beads (Amershamn) were added to the membrane mix to a concentration of 0.4 mg/100 µL and finally $^3$H-PGD$_2$ was added to the membrane/SPA bead mix to 3.6 nM. 100 µL of the membrane/SPA bead/$^3$H-PGD$_2$ mix was added to each well of the non-surface binding plates containing the diluted compound plus controls. The plates were incubated for 2 hours at room temperature with shaking and then the plates were counted on a Microbeta scintillation counter (Perkin Elmer) for 1 min per well.

IC$_{50}$ values were determined from the experimental results by nonlinear regression using Prism 4.0 software. The IC$_{50}$ values were then used in conjunction with the Ed for hCRTH2 and the $^3$H-PGD$_2$ concentration used in the experiment to calculate the K$_i$ for each compound. The results are shown in Table 1.

TABLE 1
| Ex No. | Compound | Ki (µM) |
|---|---|---|
| 1 | 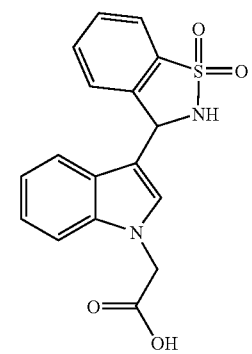 | <10 |
| 2 | 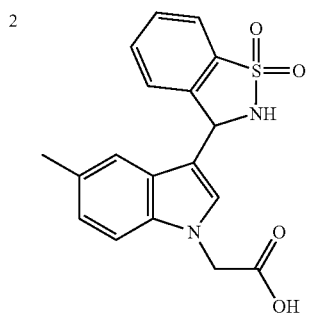 | <10 |
| 3 | 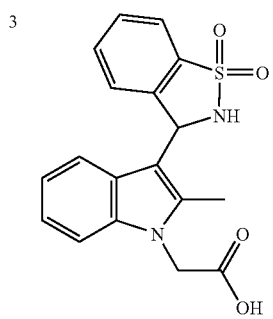 | <10 |
| 4 | 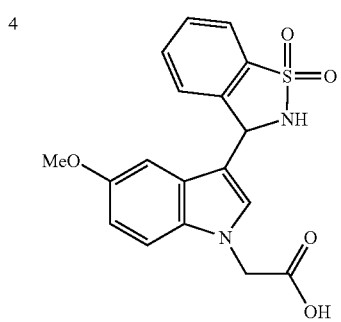 | <10 |
TABLE 1-continued
| Ex No. | Compound | Ki (µM) |
|---|---|---|
| 5 | 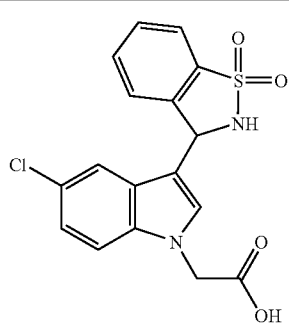 | <10 |
| 6 | 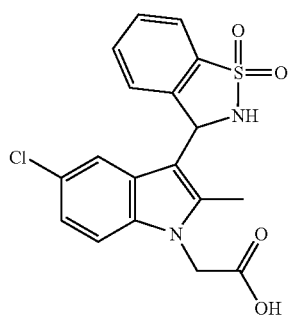 | <1 |
| 7 | 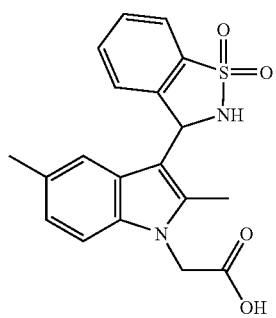 | <10 |
| 8 | 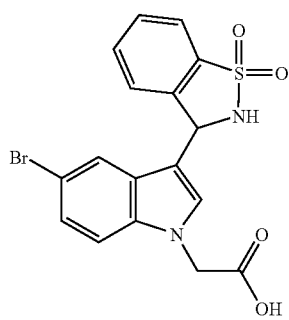 | <10 |

TABLE 1-continued

| Ex No. | Compound | Ki (μM) |
|---|---|---|
| 9 | (structure) | <10 |
| 10 | (structure) | <1 |
| 11 | (structure) | <1 |
| 12 | (structure) | <1 |
| 13 | (structure) | <1 |
| 14 | (structure) | <10 |
| 15 | (structure) | <1 |
| 16 | (structure) | <0.1 |

TABLE 1-continued

| Ex No. | Compound | Ki (μM) |
|---|---|---|
| 17 | | <1 |
| 18 | | <10 |
| 19 | | <0.1 |
| 20 | | >10 |
| 21 | | <0.1 |
| 22 | | <1 |
| 23 | | <0.1 |
| 24 | | <0.1 |

TABLE 1-continued
| Ex No. | Compound | Ki (μM) |
|---|---|---|
| 25 | 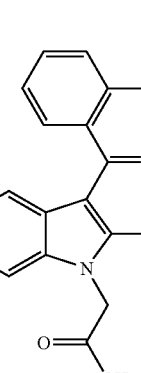 | <0.1 |
| 26 | 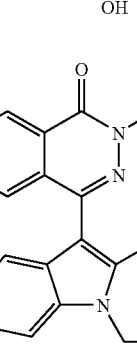 | <0.1 |
| 27 | 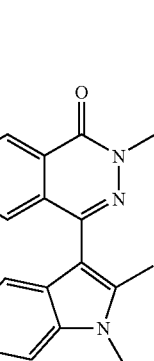 | <0.1 |
| 28 | 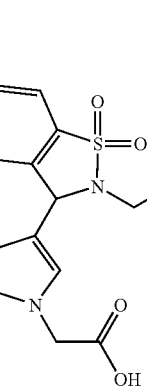 | <10 |
| 29 | 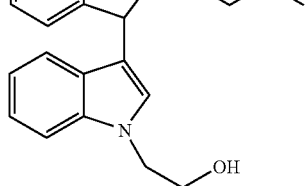 | <10 |
| 30 | 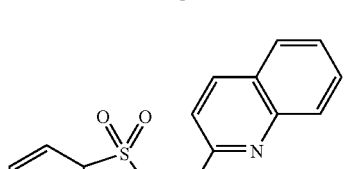 | <10 |
| 31 | | <1 |
| 32 | | <1 |

TABLE 1-continued
| Ex No. | Compound | Ki (µM) |
|---|---|---|
| 33 | 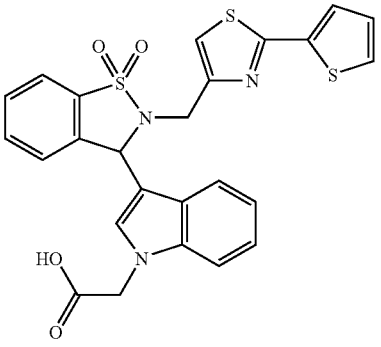 | <1 |
| 34 | 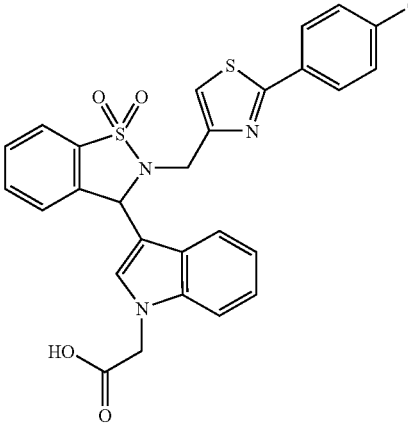 | <1 |
| 35 | 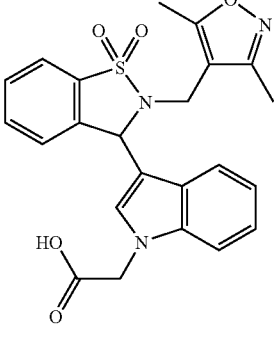 | <0.1 |
| 36 | 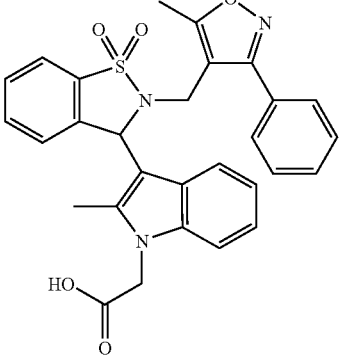 | <0.1 |
| 37 | 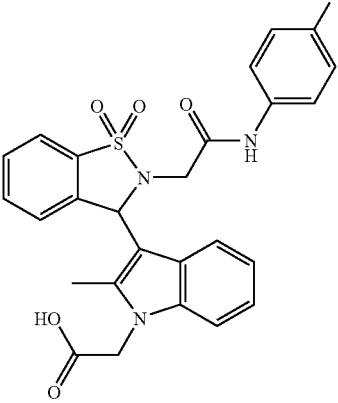 | <10 |
| 38 | 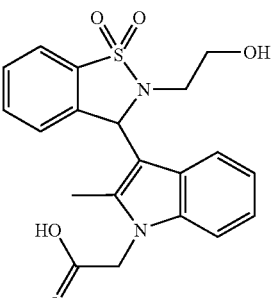 | <10 |
| 39 | 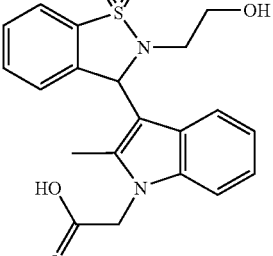 | <0.1 |
| 40 | 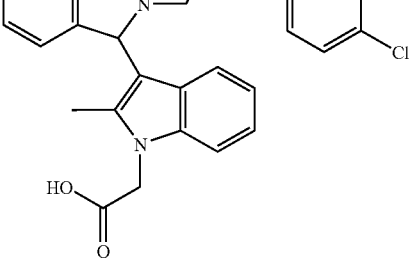 | <1 |

TABLE 1-continued
| Ex No. | Compound | Ki (μM) |
|---|---|---|
| 41 | 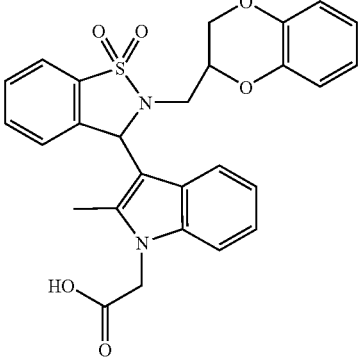 | <1 |
| 42 | 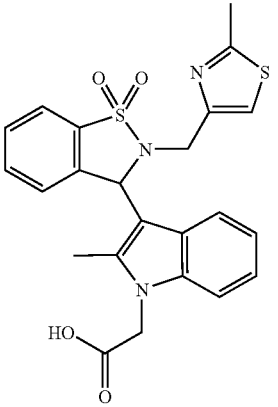 | <1 |
| 43 | 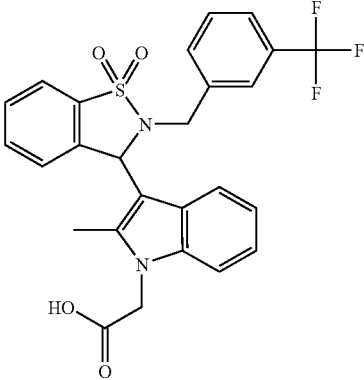 | <1 |
| 44 | 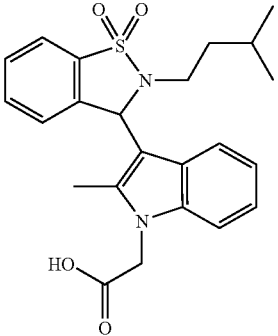 | <1 |
| 45 | 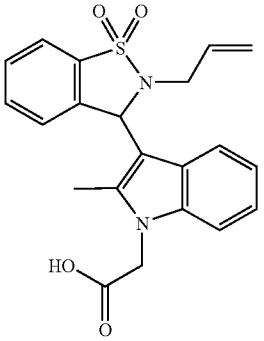 | <1 |
| 46 | 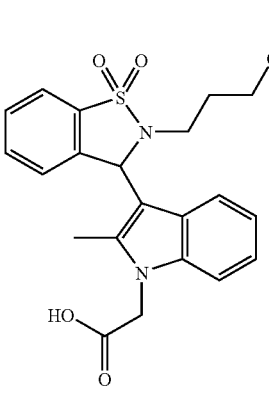 | <1 |
| 47 | 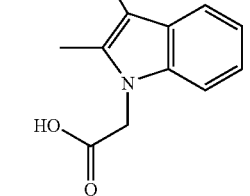 | <1 |
| 48 | 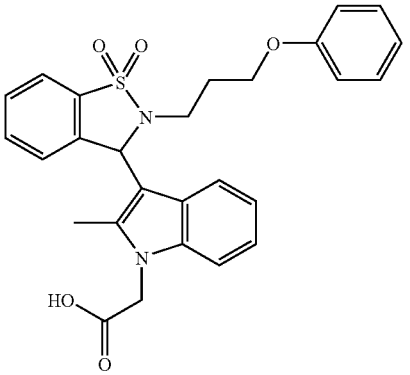 | <1 |

TABLE 1-continued
| Ex No. | Compound | Ki (μM) |
|---|---|---|
| 49 | 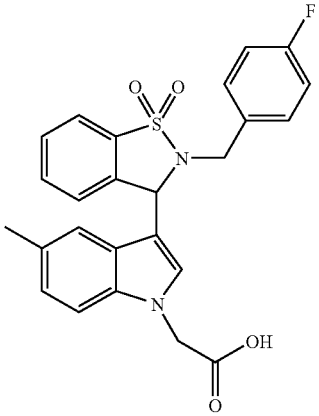 | <1 |
| 50 | 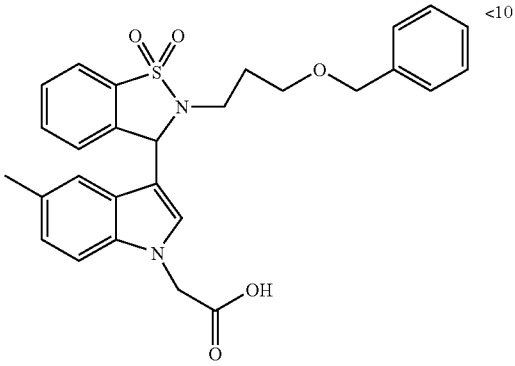 | <10 |
| 51 | 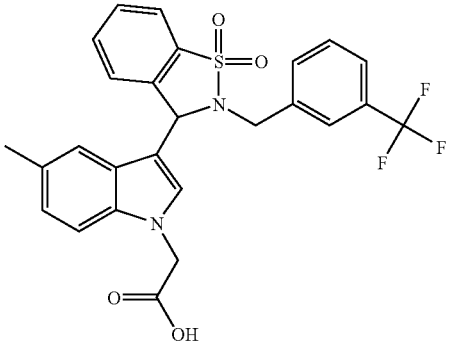 | <10 |
| 52 | 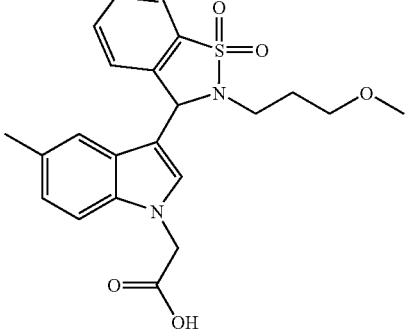 | <10 |
| 53 | 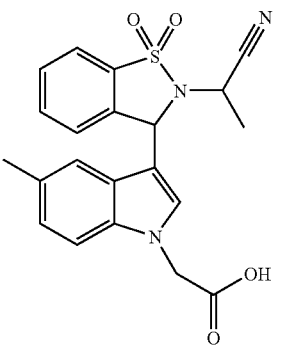 | <10 |
| 54 | 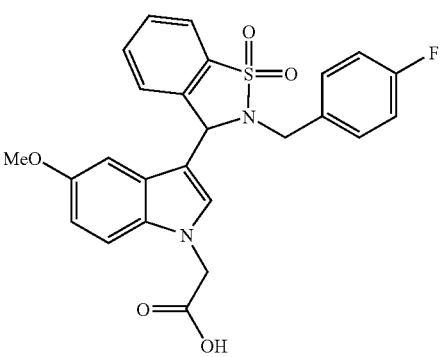 | <1 |
| 55 | 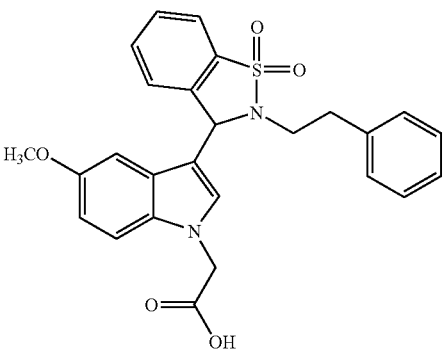 | <10 |
| 56 | 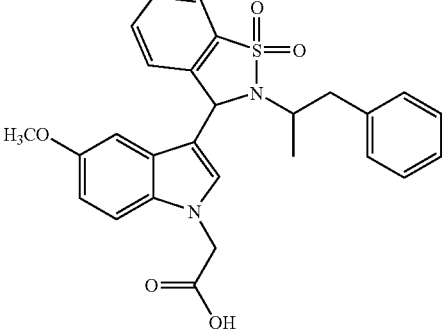 | <10 |

TABLE 1-continued

| Ex No. | Compound | Ki (μM) |
|---|---|---|
| 57 | | <10 |
| 58 | | <1 |
| 59 | | <0.1 |
| 60 | | <1 |
| 61 | | <0.1 |
| 62 | | <0.1 |
| 63 | | <1 |
| 64 | | <0.1 |

TABLE 1-continued

| Ex No. | Compound | Ki (µM) |
|---|---|---|
| 65 | (structure) | <0.1 |
| 66 | (structure) | <1 |
| 67 | (structure) | <1 |
| 68 | (structure) | <1 |
| 69 | (structure) | <0.1 |
| 70 | (structure) | <1 |
| 71 | (structure) | <1 |
| 72 | (structure) | <0.1 |

TABLE 1-continued
| Ex No. | Compound | Ki (μM) |
|---|---|---|
| 73 | 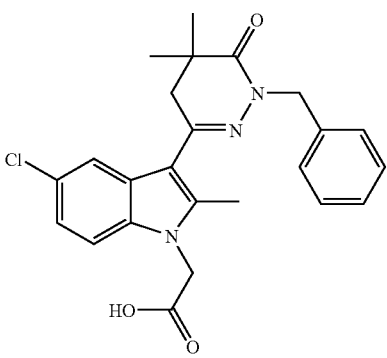 | <0.1 |
| 74 | 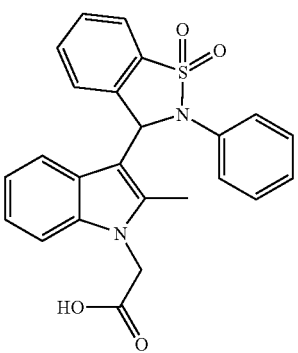 | <1 |
| 75 | 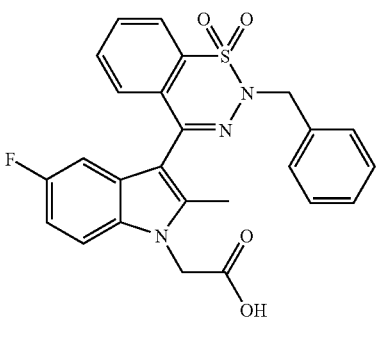 | <1 |
| 76 | 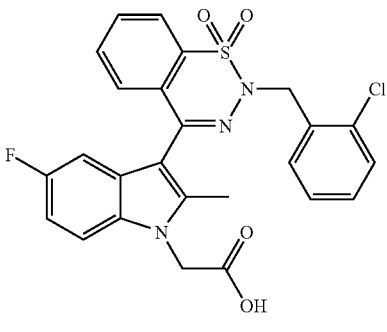 | <0.1 |
TABLE 1-continued
| Ex No. | Compound | Ki (μM) |
|---|---|---|
| 77 | 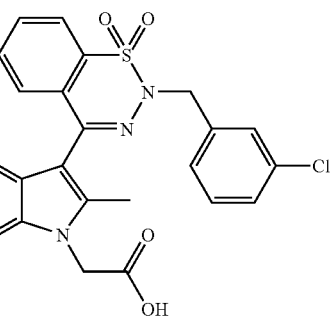 | <1 |
| 78 | 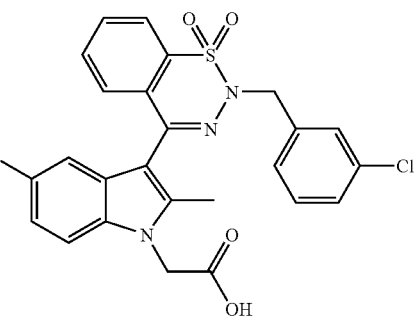 | <1 |
| 79 | 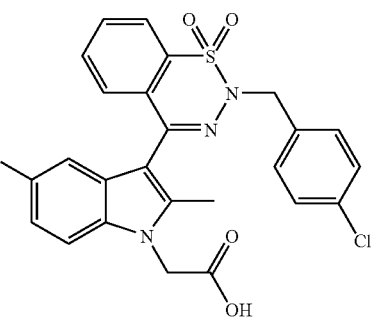 | <1 |
| 80 | 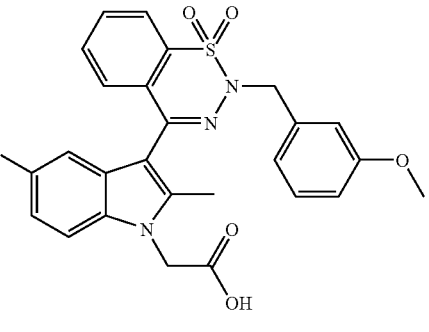 | <0.1 |

TABLE 1-continued

| Ex No. | Compound | Ki (μM) |
|---|---|---|
| 81 | (structure) | <0.1 |
| 82 | (structure) | <0.1 |
| 83 | (structure) | <0.1 |
| 84 | (structure) | <1 |
| 85 | (structure) | <1 |
| 86 | (structure) | <0.1 |
| 87 | (structure) | <1 |
| 88 | (structure) | <1 |

TABLE 1-continued

| Ex No. | Compound | Ki (μM) |
|---|---|---|
| 89 | (5-fluoro-2-methyl-indol-3-yl benzothiadiazine with N-CH2CH2-O-C6H4-Cl substituent, N-CH2COOH on indole) | <1 |
| 90 | (5-fluoro-2-methyl-indol-3-yl benzothiadiazine with N-CH2-(3,5-dimethylisoxazol-4-yl) substituent, N-CH2COOH on indole) | <0.1 |
| 91 | (5-fluoro-2-methyl-indol-3-yl benzothiadiazine with N-ethyl substituent, N-CH2COOH on indole) | <0.1 |
| 92 | (5-fluoro-2-methyl-indol-3-yl benzothiadiazine with N-propyl substituent, N-CH2COOH on indole) | <0.1 |
| 93 | (5-fluoro-2-methyl-indol-3-yl benzothiadiazine with N-isopropyl substituent, N-CH2COOH on indole) | <0.1 |
| 94 | (5-fluoro-2-methyl-indol-3-yl benzothiadiazine with N-cyclohexyl substituent, N-CH2COOH on indole) | <0.1 |

EXAMPLE 96

CRTH2 Fluorescent Imaging Assay

The ability of the disclosed compounds to act as agonists for the hCRTH2 receptor was determined by their ability to cause increases in intracellular calcium via binding to the CRTH2 receptor. The compounds were also tested for their ability to act as antagonists for the hCRTH2 receptor as measured by the ability of the compounds to block the increase in intracellular calcium normally caused by $PGD_2$ binding to the CRTH2 receptor.

Assays were performed on HEK 293EBNA-hCRTH2 cells that had been grown in DMEM media containing 10% FBS, 3 μL/mL puromycin and 1% penicillin/streptomycin/glutamine (PSG) at 37° C. in 5% $CO_2$ or on HT1080-hCRTH2 cells (a HT1080 cell line stably expressing human CRTH2) that had been grown in alphaMEM media containing 10% FBS, 500 μg/ml hygromycin, 200 nM methotrexate and 1% PSG at 37° C. in 5% $CO_2$.

For the assay, HEK 293EBNA-hCRTH2 cells or HT1080-hCRTH2 cells were grown to approximately 90% confluency and then dislodged from the plate with Trypsin-EDTA, resuspended in DMEM media, seeded in 384 well plates at $2 \times 10^4$ cells per well and incubated overnight at 37° C. The cells were loaded with a calcium sensing dye by removing the growth media and replacing it with 30 μL of dye loading Ringer's buffer (136 mM CsCl, 5.4 mM D-Glucose, 20 mM Hepes pH 7.4, 2.1 mM $MgCl_2$, 0.8 mM $CaCl_2$, 0.2% BSA with 1× Calcium3Dye (Molecular Devices) and 2.5 mM Probenecid (Sigma)) per well. The cells were incubated at 37° C. for 1 hour to allow the dye to enter the cells. Compounds were serially diluted in DMSO and then diluted to 4× their final concentration with Ringer's buffer. The compounds were added to a 384 well plate in quadruplicate. In addition to test compounds, several wells contained Ringer's buffer with DMSO. These wells serve as control wells. 10 μL was transferred from compound/control plate to the plate containing cells loaded with dye by a fluorescent imaging plate reader (Molecular Devices). The fluorescence was measured every 4 seconds for 4 minutes. These measurements indicated the level of intracellular calcium. Increases in fluorescence relative to wells containing buffer only indicated an agonist effect of the compound. Measurement at various compound concentrations allowed one to determine the $EC_{50}$ for these compounds. Following the 4 minute incubation with compound, 20 μL of Ringer's buffer with either 10 nM or 500 nM $PGD_2$ (approximate $EC_{75}$ for $PGD_2$ in HEK 293EBNA-hCRTH2 cells and HT1080-hCRTH2 cells, respectively) was added to the wells. Inhibition by the compounds of the calcium response due to antagonism of $PGD_2$ action on CRTH2 is reflected by a decrease in fluorescent signal relative to wells containing no compound. The fluorescence was measured every 2 seconds for 10 seconds before addition of $PGD_2$ and every 2 seconds for 110 seconds following addition. Measurement at various compound concentrations allowed one to determine the $IC_{50}$ for these compounds. $EC_{50}$ and $IC_{50}$ values were determined from the experimental results by non-linear regression using the Prism 4.0 software. The results are shown in Table 2.

TABLE 2

| Example Number | HT1080-hCRTH2 $IC_{50}$ (μM) |
|---|---|
| 16 | 0.019 |
| 24 | 0.06 |
| 61 | 0.17 |
| 62 | 0.022 |

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

What is claimed is:

1. A compound having Formula IV:

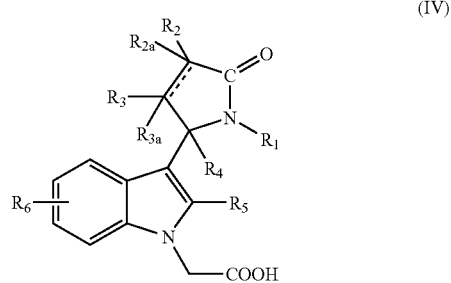

(IV)

or a pharmaceutically acceptable salt, ester or amide thereof, where said ester is derived from a $C_{1-6}$ alcohol and said amide is derived from a $C_{1-6}$ amine,
wherein:
the dotted line is a single or double bond;
$R_1$ is selected from H, optionally substituted $C_{1-10}$ alkyl, optionally substituted $C_{2-10}$ alkenyl, optionally substituted $C_{2-10}$ alkynyl, optionally substituted $C_{1-10}$ alkylaryl, optionally substituted $C_{1-10}$ alkylheteroaryl, optionally substituted $-C_{1-10}$ alkyl-O-$C_{1-10}$ alkyl, optionally substituted $-C_{1-10}$ alkyl-O-aryl, optionally substituted $-C_{1-10}$ alkyl-O-heteroaryl, optionally substituted aryl, and optionally substituted heteroaryl;

$R_2$, $R_{2a}$, $R_3$ and $R_{3a}$ are independently selected from H, halogen, and $C_{1-10}$ alkyl, wherein $R_{2a}$ and $R_{3a}$ are present only when the carbons to which they are attached are saturated; or $R_2$ and $R_3$ taken together with the carbon atoms to which they are attached, form an optionally substituted saturated, unsaturated, or aromatic 5- or 6-membered ring; or $R_2$ and $R_{2a}$ taken together with the carbon atoms to which they are attached, form an optionally substituted saturated 3-6 membered ring;

$R_4$ is H, $C_{1-10}$ alkyl, $C_{2-10}$ alkenyl, $C_{2-10}$ alkynyl, or halogen, wherein $R_4$ is present only when the carbon to which it is attached is saturated;

$R_5$ is H, $C_{1-10}$ alkyl, perhaloalkyl, $C_{2-10}$ alkenyl, $C_{2-10}$ alkynyl, $C_{1-10}$ alkylaryl, $C_{1-10}$ alkylheteroaryl, aryl, or heteroaryl, wherein said aryl or heteroaryl is optionally substituted with one or more substituents selected from $C_{1-10}$ alkyl, halogen, $C_{1-10}$ alkoxy, and CN;

$R_6$ is one or more H, halogen, $C_{1-10}$ alkyl, $C_{2-10}$ alkenyl, $C_{2-10}$ alkynyl, CN, $OR_7$, $SR_7$, aryl or heteroaryl groups; and $R_7$ is H, $C_{2-10}$ alkyl, $C_{2-10}$ alkenyl, $C_{2-10}$ alkynyl, aryl, or heteroaryl, wherein unless otherwise specified, optional substituents are selected from $C_{1-10}$ alkyl, halogen, halo $C_{1-10}$ alkyl, halo $C_{1-10}$ alkoxy, cycloalkyl, hydroxy, cyano, aryl, aryloxy, carbamoyl, aralkyl, heteroaryl, heteroaryloxy, alkoxycarbonyl, amino, acyloxy, arylacyloxy, heterocyclo, heterocycloalkoxy, partially unsaturated heterocyclalkyl and partially unsaturated heterocyclylalkoxy, and where each optional substituent may be further substituted with one or more $C_{1-6}$ alkly, halogen, halo $C_{1-10}$ alkyl, $C_{1-10}$ alkoxy, haloalkoxy, aryl, or heteroaryl groups.

2. A compound which is:
[3-(2-methyl-3-oxo-2,3,-dihydro-1H-isoindol-1-yl)-indol-1-yl]-acetic acid;
{3-[2-(3,5-dimethyl-isoxazol-4-ylmethyl)-3-oxo-2,3-dihydro-1H-isoindol-1-yl]-indol-1-yl}-acetic acid; or
{3-[2-(3,5-dimethyl-isoxazol-4-ylmethyl)-3-oxo-2,3,dihydro-1H-isoindol-1-yl]-2-methyl-indol-1-yl}-acetic acid, or a pharmaceutically acceptable salt, ester or amide thereof, where said ester is derived from a $C_{1-6}$ alcohol and said amide is derived from a $C_{1-6}$ amine.

3. A pharmaceutical composition comprising a compound of claim 1, or a pharmaceutically acceptable salt, ester or amide thereof, and a pharmaceutically acceptable carrier.

4. A method of treating in a mammal, comprising administering to said mammal a therapeutically effective amount of a compound of claim 1, or a pharmaceutically acceptable salt, ester or amide thereof wherein the disorder is selected from asthma, chronic obstructive pulmonary disease, bronchitis, rhinitis, nasal polyposis, sarcoidosis, farmer's lung, fibroid lung, idiopathic interstitial pneumonia, cystic fibrosis, cough, psoriasis, dermatitis, urticaria, cutaneous eosinophilias, food-related allergies, eosinophilia fascitis and hyper IgE syndrome.

5. The method of claim 4, wherein said disorder is asthma, chronic obstructive pulmonary disease, bronchitis, rhinitis, nasal polyposis, sarcoidosis, farmer's lung, fibroid lung, idiopathic interstitial pneumonia, cystic fibrosis, or cough.

6. The method of claim 4, wherein said disorder is psoriasis, dermatitis, urticaria or cutaneous eosinophilias.

7. The method of claim 4, wherein said disorder is food-related allergies.

8. The method of claim 4, wherein said disorder is eosinophilia fascitis, or hyper IgE syndrome.

9. The method of claim 4, further comprising administering an additional therapeutic agent.

10. A kit comprising a compound of claim 1, or a pharmaceutically acceptable salt, ester or amide thereof, and instructions for administering said compound, pharmaceutically acceptable salt, ester or amide thereof, to an animal.

11. The kit of claim 10, further comprising an additional therapeutic agent.

12. A method of preparing a compound having formula XXVIII, comprising a) reducing a compound having formula XXV to form a compound having formula XXVI;

XXV

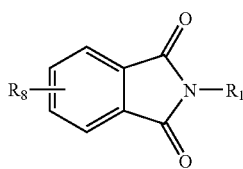

XXVI

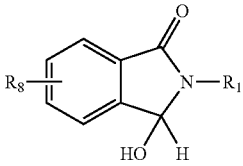

b) condensing a compound having formula XXVI with an indole compound VIII to form a compound having formula XXVII; and

VIII

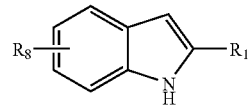

XXVII

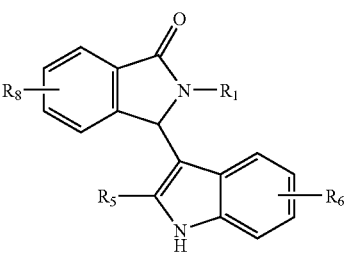

c) condensing a compound having formula XXVII with a halogenated acetic acid alkyl ester followed by deprotecting to form a compound having formula XXVIII;

XXVIII

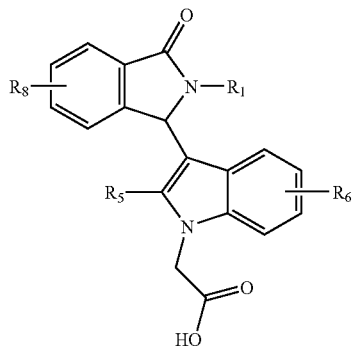

wherein $R_1$ is selected from H, optionally substituted $C_{1-10}$ alkyl, optionally substituted $C_{2-10}$ alkenyl, optionally substituted $C_{2-10}$ alkynyl, optionally substituted $C_{1-10}$ alkylaryl, optionally substituted $C_{1-10}$ alkylheteroaryl, optionally substituted $-C_{1-10}$ alkyl-O-$C_{1-10}$ alkyl, optionally substituted $-C_{1-10}$ alkyl-O-aryl, optionally substituted $-C_{1-10}$ alkyl-O-heteroaryl, optionally substituted aryl, and optionally substituted heteroaryl, where unless otherwise specified, optional substituents are selected from $C_{1-10}$ alkyl, halogen, halo $C_{1-10}$ alkyl, halo $C_{1-10}$ alkoxy, cycloalkyl, hydroxy, cyano, aryl, aryloxy, carbamoyl, aralkyl, heteroaryl, heteroaryloxy, alkoxycarbonyl, amino, acyloxy, arylacyloxy, heterocyclo, heterocycloalkoxy, partially unsaturated heterocyclylalkyl and partially unsaturated heterocyclylalkoxy, and where each optional substituent may be further substituted with one or more $C_{1-6}$ alkyl, halogen, halo $C_{1-10}$ alkyl, $C_{1-10}$ alkoxy, haloalkoxy, aryl, or heteroaryl groups;

$R_5$ is H, $C_{1-10}$ alkyl, perhaloalkyl, $C_{2-10}$ alkenyl, $C_{2-10}$ alkynyl, $C_{1-10}$ alkylaryl, $C_{1-10}$ alkylheteroaryl, aryl, or heteroaryl, wherein said aryl or heteroaryl can be optionally substituted with one or more substituents selected from $C_{1-10}$ alkyl, halogen, $C_{1-10}$ alkoxy, or CN;

$R_6$ is one or more H, halogen, $C_{1-10}$ alkyl, $C_{2-10}$ alkenyl, $C_{2-10}$ alkynyl, CN; $OR_7$, $SR_7$, aryl or heteroaryl groups;

$R_7$ is H, $C_{1-10}$ alkyl, $C_{2-10}$ alkenyl, $C_{2-10}$ alkynyl, aryl, or heteroaryl; and $R_8$ is H, halo, $C_{1-10}$ alkoxy, cyano, $C_{1-10}$ alkyl, $C_{2-10}$ alkenyl, $C_{2-10}$ alkynyl, $C_{1-10}$ alkylaryl, $C_{1-10}$ alkylheteroaryl, $-C_{1-10}$ alkyl-O-$C_{1-10}$ alkyl, $-C_{1-10}$ alkyl-O-aryl, $-C_{1-10}$ alkyl-O-heteroaryl, aryl, or heteroaryl.

13. A method of preparing a compound having formula XXVIII, comprising condensing a compound having formula XXVII with a halogenated acetic acid alkyl ester followed by deprotecting to form a compound having formula XXVIII;

XXVII

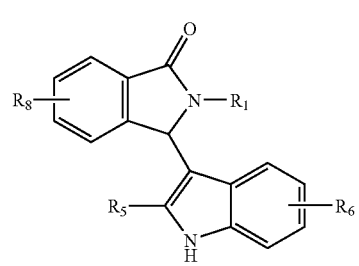

XXVIII

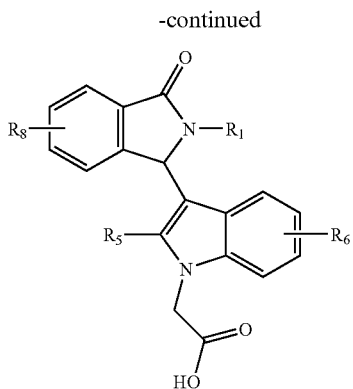

wherein
- $R_1$ is selected from H, optionally substituted $C_{1-10}$ alkyl, optionally substituted $C_{2-10}$ alkenyl, optionally substituted $C_{2-10}$ alkynyl, optionally substituted $C_{1-10}$ alkylaryl, optionally substituted $C_{1-10}$ alkylheteroaryl, optionally substituted -$C_{1-10}$ alkyl-O-$C_{1-10}$ alkyl, optionally substituted -$C_{1-10}$ alkyl-O-aryl, optionally substituted -$C_{1-10}$ alkyl-O-heteroaryl, optionally substituted aryl, and optionally substituted heteroaryl, where unless otherwise specified, optional substituents are selected from $C_{1-10}$ alkyl, halogen, halo $C_{1-10}$ alkyl, halo $C_{1-10}$ alkoxy, cycloalkyl, hydroxy, cyano, aryl, aryloxy, carbamoyl, aralkyl, heteroaryl, heteroaryloxy, alkoxycarbonyl, amino, acyloxy, arylacyloxy, heterocyclo, heterocycloalkoxy, partially unsaturated heterocyclylalkyl and partially unsaturated heterocyclylalkoxy, and where each optional substituent may be further substituted with one or more $C_{1-6}$ alkyl, halogen, halo $C_{1-10}$ alkyl, $C_{1-10}$ alkoxy, haloalkoxy, aryl, or heteroaryl groups;
- $R_5$ is H, $C_{1-10}$ alkyl, perhaloalkyl, $C_{2-10}$ alkenyl, $C_{2-10}$ alkynyl, $C_{1-10}$ alkylaryl, $C_{1-10}$ alkylheteroaryl, aryl, or heteroaryl, wherein said aryl or heteroaryl can be optionally substituted with one or more substituents selected from $C_{1-10}$ alkyl, halogen, $C_{1-10}$ alkoxy, or CN;
- $R_6$ is one or more H, halogen, $C_{1-10}$ alkyl, $C_{2-10}$ alkenyl, $C_{2-10}$ alkynyl, CN, $OR_7$, $SR_7$, aryl or heteroaryl groups;
- $R_7$ is H, $C_{1-10}$ alkyl, $C_{2-10}$ alkenyl, $C_{2-10}$ alkynyl, aryl, or heteroaryl; and
- $R_8$ is H, halo, $C_{1-10}$ alkoxy, cyano, $C_{1-10}$ alkyl, $C_{2-10}$ alkenyl, $C_{2-10}$ alkynyl, $C_{1-10}$ alkylaryl, $C_{1-10}$ alkylheteroaryl, -$C_{1-10}$ alkyl-O-$C_{1-10}$ alkyl, -$C_{1-10}$ alkyl-O-aryl, -$C_{1-10}$ alkyl-O-heteroaryl, aryl, or heteroaryl.

14. The compound of claim 1, or a pharmaceutically acceptable salt, ester or amide thereof, wherein:
- $R_1$ is selected from optionally substituted $C_{1-10}$ alkyl, optionally substituted $C_{2-10}$ alkenyl, optionally substituted $C_{1-10}$ alkylheteroaryl, and optionally substituted $C_{1-10}$ alkylaryl;
- $R_4$ is H or $C_{1-10}$ alkyl;
- $R_5$ is H or $C_{1-10}$ alkyl; and
- $R_6$ is H or $C_{1-10}$ alkyl.

15. The compound of claim 14, or a pharmaceutically acceptable salt, ester or amide thereof, wherein $R_1$ is chosen from methyl and -$CH_2$-(3,5- dimethylisoxazol-4-yl).

16. The compound of claim 14 or a pharmaceutically acceptable salt, ester, or amide thereof, wherein $R_2$ and $R_3$, taken together with the carbon atoms to which they are attached, form a saturated, unsaturated or aromatic 5- or 6-membered ring.

17. The compound of claim 16 or a pharmaceutically acceptable salt, ester, or amide thereof, wherein $R_2$ and $R_3$, taken together with the carbon atoms to which they are attached, form a benzene ring.

18. The compound of claim 14 or a pharmaceutically acceptable salt, ester, or amide thereof, wherein $R_4$ is H.

19. The compound of claim 14 or a pharmaceutically acceptable salt, ester, or amide thereof, wherein $R_5$ is H or methyl.

20. The compound of claim 14 or a pharmaceutically acceptable salt, ester, or amide thereof, wherein $R_6$ is H.

21. The method of claim 4, wherein the mammal is a human, and wherein
- $R_1$ is $C_{1-10}$ alkyl or optionally substituted $C_{1-10}$ alkylheteroaryl;
- $R_2$ and $R_3$, taken together with the carbon atoms to which they are attached, form an optionally substituted saturated, unsaturated or aromatic 5- or 6-membered ring;
- $R_4$ is H;
- $R_5$ is H or $C_{1-10}$ alkyl; and
- $R_6$ is H.

22. The method of claim 21, wherein the disorder is asthma, chronic obstructive pulmonary disease, bronchitis, rhinitis, nasal polyposis, sarcoidosis, farmer's lung, fibroid lung, idiopathic interstitial pneumonia, cystic fibrosis, or cough.

23. The method of claim 22, wherein the disorder is asthma or chronic obstructive pulmonary disease.

* * * * *

UNITED STATES PATENT AND TRADEMARK OFFICE
CERTIFICATE OF CORRECTION

PATENT NO. : 7,601,749 B2
APPLICATION NO. : 12/336274
DATED : October 13, 2009
INVENTOR(S) : Bennani et al.

It is certified that error appears in the above-identified patent and that said Letters Patent is hereby corrected as shown below:

In the claims:

Claim 1, column 110, line 5, "$R_2$ ," should read --$R_2$,--.

Claim 1, column 110, line 25, "$C_{2-10}$ alkyl," should read --$C_{1-10}$ alkyl,--.

Claim 1, column 110, lines 32-33, "heterocycylalkyl" should read --heterocyclylalkyl--.

Claim 2, column 110, lines 44-45, "{3-[2-(3,5-dimethyl-isoxazol-4-ylmethyl)-3-oxo-2,3,dihydro-1H-isoindol-1-yl]-2-methyl-indol-1-yl}-acetic" should read --{3-[2-(3,5-dimethyl-isoxazol-4-ylmethyl)-3-oxo-2,3-dihydro-1H-isoindol-1-yl]-2-methyl-indol-1-yl}-acetic--.

Claim 4, column 110, line 52, "treating in a" should read --treating a--.

Claim 8, column 111, line 4, "lgE" should read --IgE--.

Claim 12, column 111, lines 45-50,

" 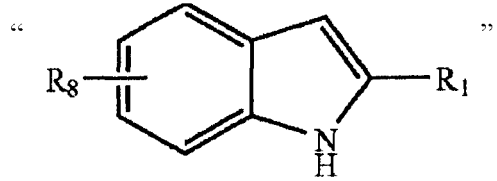 "

should read

_ 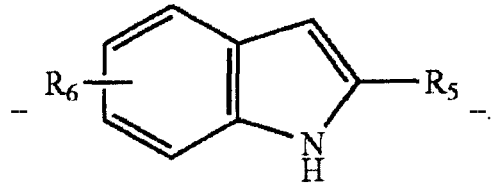 _.

Signed and Sealed this

Eleventh Day of May, 2010

David J. Kappos
*Director of the United States Patent and Trademark Office*

Claim 12, column 112, line 43, "CN; OR$_7$ ," should read --CN, OR$_7$,--.

Claim 12, column 112, line 48, "C $_{1-10}$" should read --C$_{1-10}$--.

Claim 15, column 114, line 14, "-CH$_2$-(3,5- dimethylisoxazol-4-yl)." should read -- -CH$_2$-(3,5-dimethylisoxazol-4-yl).--.